US012564392B2

(12) United States Patent
Johnson et al.

(10) Patent No.:  US 12,564,392 B2
(45) Date of Patent:  Mar. 3, 2026

(54) CONTAINMENT BAG

(71) Applicant: Eximis Surgical Inc., Louisville, CO
(US)

(72) Inventors: Dirk Johnson, Louisville, CO (US);
Kristin D. Johnson, Louisville, CO
(US); William N. Gregg, Superior, CO
(US); Steven C. Rupp, Arvada, CO
(US); Steve Choi, Lafayette, CO (US);
Armando Garcia, Longmont, CO (US);
Hana Creasy, Westminster, CO (US);
Chris Underwood, Broomfield, CO
(US)

(73) Assignee: EXIMIS SURGICAL INC., Louisville,
CO (US)

( * ) Notice: Subject to any disclaimer, the term of this
patent is extended or adjusted under 35
U.S.C. 154(b) by 742 days.

(21) Appl. No.: 17/895,784

(22) Filed: Aug. 25, 2022

(65) Prior Publication Data

US 2023/0085327 A1    Mar. 16, 2023

Related U.S. Application Data

(60) Provisional application No. 63/237,024, filed on Aug.
25, 2021.

(51) Int. Cl.
A61B 17/00        (2006.01)
A61B 17/34        (2006.01)
(52) U.S. Cl.
CPC .... A61B 17/00234 (2013.01); A61B 17/3417
(2013.01); *A61B 2017/00287* (2013.01); *A61B
2017/3456* (2013.01)
(58) Field of Classification Search
CPC ............ A61B 2017/00287; A61B 2017/00234
See application file for complete search history.

(56) References Cited

U.S. PATENT DOCUMENTS

| 4,368,734 A | 1/1983 | Banko |
| 5,050,426 A | 9/1991 | Banko |

(Continued)

FOREIGN PATENT DOCUMENTS

| CN | 1953716 A | 4/2007 |
| CN | 101123924 A | 2/2008 |

(Continued)

OTHER PUBLICATIONS

European Patent Office, "Office Action Regarding Application No.
16 781 594.3", Aug. 30, 2019, p. 5, Published in: EP.

(Continued)

*Primary Examiner* — Katherine H Schwiker
(74) *Attorney, Agent, or Firm* — Rogue.law; Laura
Schneider

(57)        ABSTRACT

A containment bag assembly for extracting a tissue speci-
men comprises a bag having one or more segmenting wires,
an outer tube comprising a proximal and distal end, a
flexible ring configured to form a top opening of the con-
tainment bag, wherein the flexible ring comprises two ring
subassemblies, each having a proximal and distal end, a
flexible member positioned between and coupled to the
distal ends of the two ring subassemblies, wherein, when the
flexible member is in a collapsed position, the two ring
subassemblies are in a collapsed position and the contain-
ment bag is configured to be stored within the outer tube, and
wherein, when the flexible member is in an expanded
position, the two ring subassemblies and the flexible mem-
ber bias the top opening of the containment bag to an open
position to enable placement of the tissue specimen within
the containment bag.

14 Claims, 44 Drawing Sheets

(56) References Cited

U.S. PATENT DOCUMENTS

| | | | |
|---|---|---|---|
| 5,143,082 | A | 9/1992 | Kindberg et al. |
| 5,196,799 | A | 3/1993 | Beard et al. |
| 5,312,416 | A | 5/1994 | Spaeth et al. |
| 5,354,303 | A | 10/1994 | Spaeth et al. |
| 5,524,633 | A | 6/1996 | Heaven et al. |
| 5,569,284 | A | 10/1996 | Young et al. |
| 5,611,803 | A | 3/1997 | Heaven et al. |
| 5,643,283 | A | 7/1997 | Younker |
| 5,735,289 | A | 4/1998 | Pfeffer et al. |
| 5,814,044 | A | 9/1998 | Hooven |
| 5,836,953 | A | 11/1998 | Yoon |
| 5,868,740 | A | 2/1999 | LeVeen et al. |
| 5,968,040 | A | 10/1999 | Swanson et al. |
| 5,971,995 | A | 10/1999 | Rousseau |
| 6,277,083 | B1 | 8/2001 | Eggers et al. |
| 6,280,450 | B1 | 8/2001 | McGuckin |
| 6,383,196 | B1 | 5/2002 | Leslie et al. |
| 6,537,273 | B1 | 3/2003 | Sosiak et al. |
| 6,558,410 | B1 | 5/2003 | Horton, III et al. |
| 6,685,628 | B2 | 2/2004 | Vu |
| 6,740,079 | B1 | 5/2004 | Eggers et al. |
| 6,752,811 | B2 | 6/2004 | Chu et al. |
| 7,004,942 | B2 | 2/2006 | Laird et al. |
| 7,052,501 | B2 | 5/2006 | McGuckin et al. |
| 7,244,255 | B2 | 7/2007 | Daners et al. |
| 7,474,909 | B2 | 1/2009 | Phan et al. |
| 7,753,920 | B2 | 7/2010 | McGuckin et al. |
| 8,192,436 | B2 | 6/2012 | Schmitz et al. |
| 8,377,054 | B2 | 2/2013 | Gilbert |
| 8,386,006 | B2 | 2/2013 | Schouenborg |
| 8,758,349 | B2 | 6/2014 | Germain et al. |
| 8,790,335 | B2 | 7/2014 | Gilbert |
| 8,920,412 | B2 | 12/2014 | Fritz et al. |
| 9,522,034 | B2 | 12/2016 | Johnson et al. |
| 9,649,147 | B2 | 5/2017 | Gilbert et al. |
| 10,603,100 | B2 | 3/2020 | Gilbert et al. |
| 2002/0068943 | A1 | 6/2002 | Chu et al. |
| 2002/0095152 | A1 | 7/2002 | Ciarrocca et al. |
| 2004/0002683 | A1 | 1/2004 | Nicholson et al. |
| 2004/0162554 | A1 | 8/2004 | Lee et al. |
| 2005/0267492 | A1 | 12/2005 | Poncet et al. |
| 2006/0167470 | A1 | 7/2006 | McGuckin |
| 2007/0088370 | A1 | 4/2007 | Kahle et al. |
| 2007/0185511 | A1 | 8/2007 | Minosawa et al. |
| 2008/0027428 | A1 | 1/2008 | Palanker et al. |
| 2008/0221604 | A1 | 9/2008 | Kondoh et al. |
| 2009/0149851 | A1 | 6/2009 | Craig |
| 2009/0149865 | A1 | 6/2009 | Schmitz et al. |
| 2009/0192510 | A1 | 7/2009 | Bahney |
| 2009/0326546 | A1 | 12/2009 | Mohamed et al. |
| 2010/0145329 | A1 | 6/2010 | Bystryak et al. |
| 2010/0152746 | A1 | 6/2010 | Ceniccola et al. |
| 2011/0040314 | A1 | 2/2011 | McGuckin, Jr. et al. |
| 2011/0087212 | A1 | 4/2011 | Aldridge et al. |
| 2011/0087235 | A1 | 4/2011 | Taylor et al. |
| 2011/0184311 | A1 | 7/2011 | Parihar et al. |
| 2011/0184432 | A1 | 7/2011 | Parihar et al. |
| 2011/0184433 | A1 | 7/2011 | Parihar et al. |
| 2011/0184435 | A1 | 7/2011 | Parihar et al. |
| 2012/0083795 | A1 | 4/2012 | Fleming et al. |
| 2012/0083796 | A1 | 4/2012 | Grover et al. |
| 2012/0203241 | A1 | 8/2012 | Williamson, IV |
| 2013/0006239 | A1 | 1/2013 | Pikramenos et al. |
| 2013/0041373 | A1 | 2/2013 | Laufer |
| 2013/0118233 | A1 | 5/2013 | Dzikowicz |
| 2013/0123783 | A1 | 5/2013 | Marczyk |
| 2013/0131445 | A1 | 5/2013 | Zerfas et al. |
| 2014/0052018 | A1 | 2/2014 | Hawkins |
| 2014/0249541 | A1 | 9/2014 | Kahle et al. |
| 2014/0276801 | A1 | 9/2014 | Juergens |
| 2014/0276913 | A1 | 9/2014 | Tah et al. |
| 2014/0288486 | A1 | 9/2014 | Hart et al. |
| 2015/0157397 | A1 | 6/2015 | Sukthankar et al. |
| 2015/0289864 | A1 | 10/2015 | Holsten et al. |
| 2016/0022352 | A1 | 1/2016 | Johnson et al. |
| 2016/0030073 | A1 | 2/2016 | Isakov et al. |
| 2016/0324515 | A1* | 11/2016 | Ravikumar ........ A61B 17/3468 |
| 2017/0079708 | A1 | 3/2017 | Gilbert et al. |
| 2017/0119455 | A1 | 5/2017 | Johnson et al. |
| 2019/0328376 | A1 | 10/2019 | Gill et al. |
| 2019/0336152 | A1 | 11/2019 | Kumar et al. |
| 2020/0113556 | A1* | 4/2020 | Paulus .................. A61B 90/98 |
| 2020/0253639 | A1* | 8/2020 | Kim ...................... A61B 17/29 |
| 2020/0330146 | A1 | 10/2020 | Gilbert et al. |
| 2021/0251683 | A1 | 8/2021 | Johnson et al. |

FOREIGN PATENT DOCUMENTS

| | | |
|---|---|---|
| CN | 201275144 Y | 7/2009 |
| CN | 103347456 A | 10/2013 |
| EP | 0703461 A2 | 3/1996 |
| EP | 1004277 A1 | 5/2000 |
| EP | 2085045 A1 | 8/2009 |
| JP | H10099342 A | 4/1998 |
| JP | 2001517529 A | 10/2001 |
| JP | 2009178555 A | 8/2009 |
| JP | 2013103137 A | 5/2013 |
| WO | 9805286 A1 | 2/1998 |
| WO | 9855037 A1 | 12/1998 |
| WO | 2005122938 A1 | 12/2005 |
| WO | 2010068467 A1 | 6/2010 |
| WO | 2014158880 A1 | 10/2014 |
| WO | 2015084769 A1 | 6/2015 |
| WO | 2017048976 A1 | 3/2017 |

OTHER PUBLICATIONS

Otero, Vanessa, "Response to Office Action Regarding U.S. Appl. No. 15/484,895", Aug. 28, 2019, p. 9, Published in: US.

Peffley, Michael, "Office Action Regarding U.S. Appl. No. 15/484,895", May 30, 2019, p. 30, Published in: US.

Chan, Alan, "Canadian Office Action Re Application No. 2955790", Mar. 9, 2017, p. 6, iublished In: CA.

Ouyang, Bo, "Office Action Re U.S. Appl. No. 14/805,358", Jun. 14, 2016, p. 100, Published in: US.

Ouyang, Bo, "Office Action Re U.S. Appl. No. 14/805,358", Dec. 24, 2015, p. 40, Published in: US.

Schneider, Laura A., "Response to Office Action Re U.S. Appl. No. 14/805,358", Mar. 2, 2016, p. 16, Published in: US.

Schneider, Laura A., "Response to Office Action Re U.S. Appl. No. 14/805,358", Jul. 5, 2016, p. 17, Published in: US.

Vizzini, Damiano, "International Search Report and Written Opinion Re Application No. PCT/US2016/051965", Jan. 11, 2017, p. 14, Published in: EP.

Baharlu, Simin, "International Preliminary Report on Patentability", Mar. 29, 2018, p. 9, Published in: WO.

Olympus America Medical, "Four-Wire Basket", Retrieved from http://medical.olympusamerica.com/products/basket/four-wire-basket, Known to exist as early as Oct. 1, 2015, p. 2, Published in: US.

Applied Medical, "Alexis Contained Extraction System", Retrieved from http://appliedmedical.com/products/Alexis_CES.aspx , Known to exist as early as Oct. 1, 2015, p. 1, Published in: US.

Barbieri, Robert L., "Options for reducing the use of open power morcellation of uterine tumors", Retrieved from http://www.mdedge.com/obgmanagement/article/80652/surgery/options-reducing-use-open-power-morcellation-uterine-tumors, Mar. 26, 2014, p. 5.

Covidien, "Principals of Electrosurgery", Known to exist as early as Sep. 30, 2015, p. 28, Publisher: Covidien AG, Published in: US.

Duck, A .Francis, "Physical Properties of Tissue", 2012, p. 5, Publisher: IPEM, Published in: US.

Covidien, "Specimen Retrieval Products", Retrieved from http://www.covidien.com/surgical/products/hand-instruments-and-ligation/specimen-retrieval-products, Known to exist as early as Oct. 1, 2015, p. 2, Published in: US.

Covidien, "Endo Catch 15mm Specimen Pouch", Retrieved from http://products.covidien.com/pages.aspx?page=PrcxluctDetai l&id=13463&cat= Devices&cat2= M cxlel, Known to exist as early as Oct. 1, 2015, p. 2, Published in: US.

(56)          References Cited

OTHER PUBLICATIONS

Covidien, "Endo Catch Gold", Retrieved from http://products. covidien.com/pages.aspx?page=ProductDetail&id=174186&cat= Devices&cat2=Model, Known to exist as early as Oct. 1, 2015, p. 1, Published in: US.
Ethicon, "Endopouch Specimen Retrieval Bag", Retrieved from http://www.ethicon.com/healthcare-professionals/products/other/lap-hand/specimen-retrieval, Known to exist as early as Oct. 1, 2015, p. 2, Published in: US.
Friedrichs, et al., "A New Dual Current-Mode Controller Improves Power Regulation in Electrosurgical Generators", "Transactions on Biomedical Curcuits and Systems", Feb. 2012, p. 6, Publisher: IEEE, Published in: US.
Hackethal, Veronica, "Morcellation Isolation Bag: Expert Quesitons Technique", "Retrieved from http://medscape.com/viewarticle/ 829476", Aug. 6, 2014, p. 2, Publisher: Medscape.
Heim, Warren P., "How Electrosurgery Really Cuts Tissue", Jan. 8, 2015, p. 3, Publisher: Team Medical, LLC, Published in: US.
Applied Medical, "Inzii Retrieval Systems", Retrieved from http:// www.appliedmedical.com/Products/Inzii.aspx, Known to exist as early as Oct. 1, 2015, p. 1, Published in: US.
Sakov, et al., "A New Laparoscopic Morcellator Using an Actuated Wire Mesh and Bag", "Journal of Medical Devices", Mar. 2014, p. 7, Publisher: ASME, Published in: US.
Young, Lee W., "WO International Search Report and Written Opinion re Application No. PCTUS1541407", Nov. 27, 2015, p. 14, Published in: WO.
Karl Storz, "Urology", Retrieved from https://www.karlstorz.com/ us/en/urology.htm, Known to exist as early as Oct. 1, 2015 , p. 7, Published in: US.
Cook Medical, "LapSac Surgical Tissue Pouch", Retrieved from https://www.cookmedical.com/products/uro_lapsac_webds/, Known to exist as early as Oct. 1, 2015, p. 2, Published in: US.
Lattis Surgical, "Lattis Contained Tissue Extraction (CTE) Device", Retrieved from http://www.lattissurgical.com/lattis-cte-vs.-morcellation. html, Known to exist as early as Oct. 1, 2015, p. 1.
Lina Medical, "LinA Bipolar Loop", Retrieved from http://www. linamed.com/products/lina-loop-range/lina-bipolar-oop/, Known to exist as early as Oct. 1, 2015, p. 6, Published in: US.
Lina Medical, "Lina Gold Loop", Retrieved from http://www. linamed.com/products/lina-loop-range/lina-gold-loop/, Known to exist as early as Oct. 1, 2015, p. 6.
Lina Medical, "Lina Gold Loop HC", Retrieved from http://www. lina-medical.com/products/lina-loop-range/lina-gold-loop-hc/, Known to exist as early as Oct. 1, 2015 , p. 6, Published in: US.
Mechcatie, Elizabeth, "Study finds insufflated collection bag successfully used in power morcellation cases", Retrieved from http:// www.mdedge.com/obgynnews/article/86182/surgery/study-finds-insufflated-collection-bag-successfully-used-power, Aug. 5, 2014, p. 2, Publisher: Ob.Gyn. News.
Tissue Extraction Task Force, "Morcellation During Uterine Tissue Extraction", "AAGL Advancing Minimally Invasive Gynecology Worldwide", p. 15, Publisher: AAGL.
Palanker, et al., "Electrosurgery With Cellular Precision", "Transactions on Biomedical Engineering", Feb. 2008, p. 4, Publisher: IEEE.
Copenheaver, Blaine R., "International Search Report and Written Opinion re Application No. PCT/2014/020649", Mar. 14, 2013, p. 15, Published in: US.
Pearce, John A., "Electrosurgery", "Biomedical Engineering Program", 1986, p. 20, Publisher: University of Texas at Austin, Published in: US.
Olympus America Medical, "Handpiece Morcellators PKS PlasmaSORD", Retrieved from http://medical.olympusamerica.com/ products/handpiece/pks-plasmaord-962000pk, Known to exist as early as Oct. 1, 2015, p. 2, Published in: US.
Olympus America Medical, "Handpiece PK Instruments PKS Bill", Retrieved from http://medical.olympusamerica.com/products/pks-bill-bl0533, Known to exist as early as Oct. 1, 2015, p. 2.

Olympus America Medical, "Loop Ligating Device PolyLoop", Retrieved from http://medical.olympusamerica.com/products/ polyloop, Known to exist as early as Oct. 1, 2015, p. 2, Published in: US.
Cook Medical, "Disposable Hysteroscopic Polyp Snare", Retrieved from https://www.cookmedical.com/products/wh_dhps_webds/, Known to exist as early as Oct. 1, 2015, p. 2, Published in: US.
Gardner, Elizabeth K., "Purdue Technology Used in First Fluorescence-Guided Ovarian Cancer Surgery", Sep. 18, 2011, p. 4, Published in: US.
Olympus America Medical, "Resection in Saline Electrodes", Retrieved from http://medical.olympusamerica.com/products/resection-saline-electrodes, Known to exist as early as Oct. 1, 2015, p. 2, Published in: US.
Olympus America Medical, "SnareMaster", Retrieved from http:// medical.olympusamerica.com/products/snaremaster, Known to exist as early as Oct. 1, 2015, p. 2.
Matos, Taina, "WO International Search Report and Written Opinion re Application No. PCT/US22/041582", Jan. 31, 2023, p. 16, Published in: US.
Megger, "A Stitch in Time the Complete Guide to Electical Insulation Testing", "Retrieved from https://www.instrumart.com/assets/ Megger-insulationtester.pdf", Jun. 8, 2016, p. 67.
The International Bureau of WIPO, "International Preliminary Report on Patentability", dated Feb. 27, 2024.
Intellectual Property India, "Examination Report Under Sections 12 and 13 of the Patents Act, 1970 and the Patents Rules, 2003 Regarding Patent Application No. 201727006187", Oct. 8, 2020, p. 6, Published in: IN.
Olympus America Medical, "Stiff Wire Basket", Webpage found at http://medical.olympusamerica.com/products/basket/stiff-wire-basket-fg-402q Inventor(s) aware of prior art on or before Sep. 30, 2015, p. 1, Published in: US.
Non Final Office Action received for U.S. Appl. No. 14/805,358 dated Dec. 24, 2015, 40 pages.
Examiner Interview Summary and OA Appendix received for U.S. Appl. No. 14/805,358 dated Feb. 24, 2016, 19 pages.
Response filed on Mar. 2, 2016 for Non Final Office Action of U.S. Appl. No. 14/805,358, 16 pages.
Final Office Action received for U.S. Appl. No. 14/805,358 dated Jun. 14, 2016, 100 pages.
Response filed on Jul. 5, 2016 for Final Office Action of U.S. Appl. No. 14/805,358, 17 pages.
Examiner Interview Summary and OA Appendix received for U.S. Appl. No. 14/805,358 dated Jul. 11, 2016, 18 pages.
Notice of Allowance received for U.S. Appl. No. 14/805,358 dated Aug. 24, 2016, 24 pages.
Supplemental Notice of Allowance received for U.S. Appl. No. 14/805,358 dated Oct. 17, 2016, 6 pages.
Heck, Falk, "Supplementary International Search Report re Application No. PCT/US2015/041407," Feb. 2, 2017, p. 12; Published in: EP.
Violante, Oscar, "Australian Examination Report re Application No. 2015292768," Jan. 3, 2018, p. 5, Published in: AU.
Chan, Alan, "Canadian Office Action re Application No. 2955790," Apr. 27, 2018, p. 4, Published in: CA.
Takahara, Yusuke, "Office Action re Patent Application No. 2017-525302," Jun. 12, 2018, p. 9, Published in: JP.
Examination Report No. 1 Regarding Standard Patent Application No. 2021202563, Nov. 30, 2021, p. 4, Published in: AU.
IP Australia, "Notice of Acceptance for Patent Application No. 2015292768", Nov. 6, 2018, p. 3, Published in: AU.
INPI, "Preliminary Search Report Regarding Brazilian Patent Application No. BR112017001378-9", Mar. 24, 2020, p. 7, Published in: BR.
Chan, Alan, "Office Action Regarding Canadian Patent Application No. 2,995,790", Dec. 3, 2018, p. 5, Published in: CA.
Borden Ladner Gervais LLP, "Response to Office Action Regarding Canadian Patent Application No. 2955790", Oct. 22, 2018, p. 13, Published in: CA.
Borden Ladner Gervais LLP, "Supplemental Response to Office Action Regarding Canadian Patent Application No. 2955790", Oct. 24, 2018, p. 13, Published in: CA.

(56) References Cited

OTHER PUBLICATIONS

China Patent Office, "Office Action Regarding Chinese Patent Application No. 201580049819.X", Oct. 9, 2018, p. 7, Published in: CN.

Neugeboren, Craig, "Concise Explanation of the Relevance of Non-English Document," Chinese Patent Application No. 201580049819.X, Dec. 5, 2018, p. 2.

CCPIT Patent and Trademark Law Office, "Response to Chinese Office Action Regarding Chinese Application No. 201580049819.X", Apr. 3, 2019, p. 15, Published in: CN.

Seiwa Patent & Law, "Response to Final Office Action Regarding Japanese Patent Application No. 2017-525302", Mar. 11, 2019, p. 7, Published in: JP.

Neugeboren, Craig, "Concise Explanation of the Relevance of Non-English Document," Japanese Patent Application No. 2017-525302, Mar. 18, 2021, p. 2.

* cited by examiner

1100

7302

7304

1200

7402

7404

1011

Proximal end

1021

1041

1081

1061

Distal end

1012

1021-b 1021-a

1041

1061

10428

10428

1044

10417

10416

10417   10416

10428

10428

Film/Perforation Layer

Active Electrode

Wire Channel Layer

Return Electrode (Optional)

Inflation Channel Layer

Film Layer

1044

10442

10441

10443

10445

10446

10444

1060

Base 1069

Bag 1062

Opening 10656

Return 10672

Extension 10676

Extension 10676

Hammock 1044

Wires 10428

Fixture 1051

1053

10673

10674

1057

1080

Opening 10656

Ring 10812

Loops 10811

Wall 10813

Base 1069

1080

Figure 28:
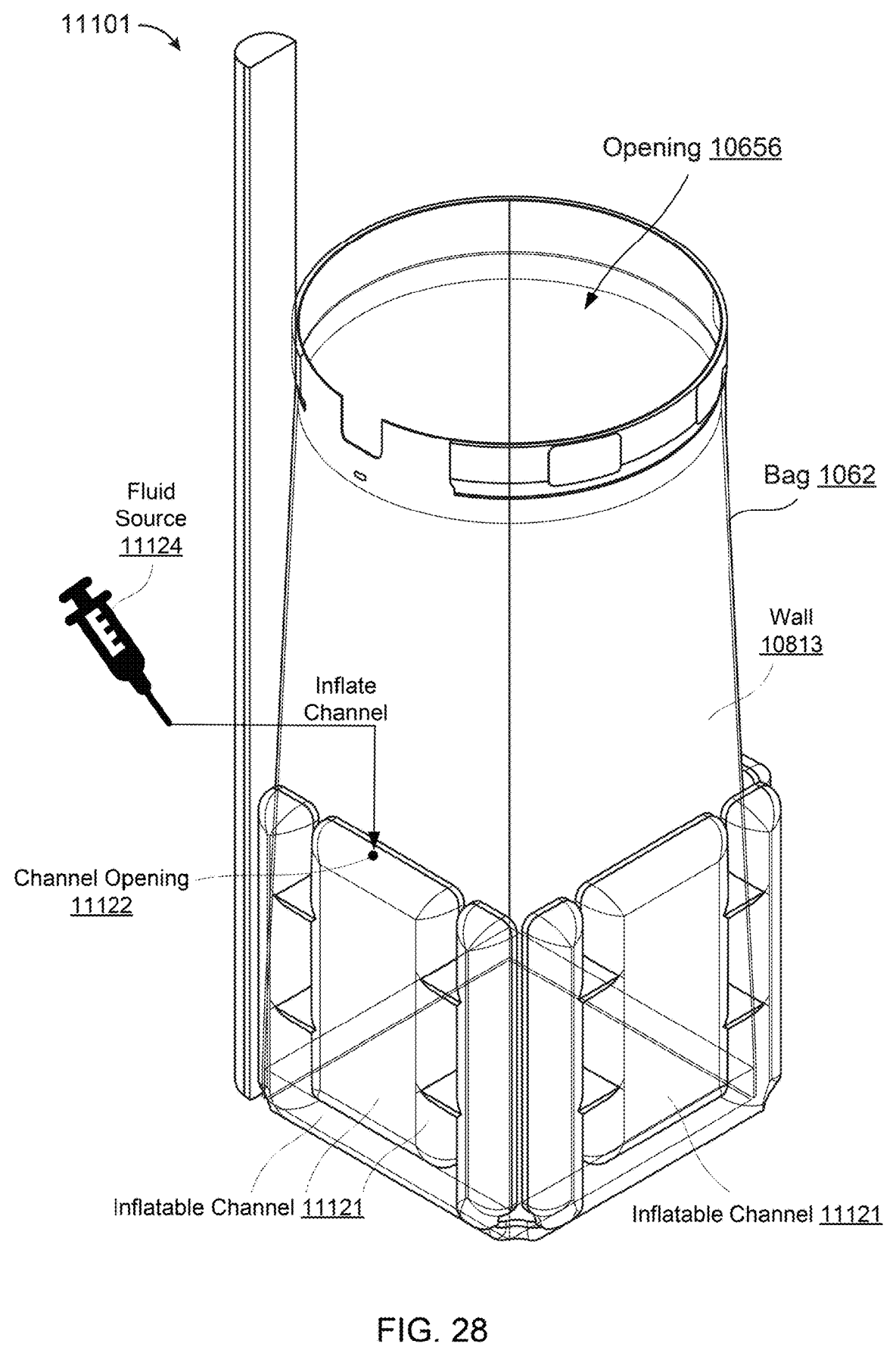

11101

Opening 10656

Bag 1062

Fluid
Source
11124

Wall
10813

Inflate
Channel

Channel Opening
11122

Inflatable Channel 11121          Inflatable Channel 11121

Bag 1062

Inflatable Channel
11121

Inflatable Channel
11121

Inflatable Channel
11121

Inflatable Channel <u>11121</u>

11101

11101

Inflatable Channel 11121

11601

Inflatable Channel 11121

11601

Inflatable Channel 11121

11601

Inflatable Channel 11121

11601

Inflatable Channel 11121

Inflatable Channel 11121

1062-b 1062-a

Perforation Layer 10441
Segmenting Wires 10442
Wire Channel Layer 10443
Return Electrode 10444
Hammock Layer 10446

1044-a

Perforation Layer 10441
Segmenting Wires 10442
Wire Channel Layer 10443
Return Electrode 10444
Hammock Layer 10446
Inflation Channel Layer 10445

1044-b

3800

10445
10447
10443
10444

1021

Wall 10813

Outer bag(s) 10446

Inner Bag 10626

Opening 10656

Tufts 11331

Inflatable Channel(s) 11121

1069

1062-e

11601

11121

11121

11331

CONTAINMENT BAG

PRIORITY AND CROSS REFERENCE TO RELATED APPLICATIONS

The present application for patent claims priority to Provisional Application No. 63/237,024, entitled "Containment Bag," filed Aug. 25, 2021 and assigned to the assignee hereof and hereby expressly incorporated by reference herein.

This application is related to U.S. application Ser. No. 16/381,661, entitled "Tissue Specimen Removal Device, System and Method," filed Apr. 11, 2019, U.S. Pat. No. 9,649,147 issued May 16, 2017 and entitled "Electrosurgical Device and Methods," and U.S. Pat. No. 9,522,034 issued Dec. 20, 2016 and entitled "Large Volume Tissue Reduction and Removal System and Method," the entire disclosures of which are hereby incorporated by reference for all proper purposes, as if fully set forth herein. The present application for patent is also related to U.S. Pat. Nos. 10,925,665; 10,603,100; and 10,873,164 entitled "Large volume Tissue Reduction and Removal System and Method", "Electrosurgical Device and Methods", and "Connector", respectively, assigned to the assignee hereof and hereby expressly incorporated by reference herein.

While various novel features are described herein, they can be used alongside or in conjunction with the inventions and disclosure set forth in the patents mentioned above. Therefore, the relevant text, figures and other disclosure from these prior patents are included in the present disclosure for context, background, and where necessary, incorporation into aspects of the inventions described herein.

FIELD OF THE DISCLOSURE

The present disclosure relates generally to devices, systems, and methods for removal of biological tissue during surgical procedures. In particular, but not by way of limitation, the present disclosure relates to a specimen or containment bag for removing biological tissue during surgical procedures.

BACKGROUND

Current methods for removing large tissue specimens with minimally invasive procedures such as, but not limited to, hysterectomy, nephrectomy, and splenectomy are to use morcellators or to manually reduce the tissue size with RF energy, mechanical cutting or fracture methods. These methods require a considerable amount of time and many sequential steps to complete. An alternative to the morcellator technique is to create a larger incision for the access port so that the tissue specimen can be removed in whole. Unfortunately, this approach leads to more patient pain and longer recovery times.

The description provided in the background section should not be assumed to be prior art merely because it is mentioned in or associated with the background section. The background section may include information that describes one or more aspects of the subject technology.

SUMMARY

The following presents a simplified summary relating to one or more aspects and/or embodiments disclosed herein. As such, the following summary should not be considered an extensive overview relating to all contemplated aspects and/or embodiments, nor should the following summary be regarded to identify key or critical elements relating to all contemplated aspects and/or embodiments or to delineate the scope associated with any particular aspect and/or embodiment. Accordingly, the following summary has the sole purpose to present certain concepts relating to one or more aspects and/or embodiments relating to the mechanisms disclosed herein in a simplified form to precede the detailed description presented below.

An aspect of the present disclosure provides a containment bag assembly for extracting a tissue specimen from a patient, the containment bag assembly comprising: a containment bag comprising one or more segmenting wires; an outer tube comprising a distal end and a proximal end; and a flexible ring, the flexible ring configured to form a top opening of the containment bag. In some implementations, the flexible ring comprises two ring subassemblies, each ring subassembly comprising a proximal end and a distal end; a flexible member positioned between and coupled to the distal ends of the two ring subassemblies, wherein the flexible member is movable between a collapsed position and an expanded position; and wherein, when the flexible member is in the collapsed position, the two ring subassemblies are in a collapsed position and the containment bag is configured to be rolled up and stored within the outer tube, and when the flexible member is in the expanded position, the two ring subassemblies and the flexible member bias the top opening of the containment bag to an open position to enable placement of the tissue specimen within the containment bag.

Another aspect of the disclosure provides a method for manufacturing a containment bag assembly, the method comprising providing a hammock assembly, wherein providing the hammock assembly comprises providing a plurality of film layers; providing a plurality of segmenting wires and a return electrode; applying tension to ends of each of the plurality of segmenting wires; and sealing the plurality of segmenting wires and the return electrode to the plurality of film layers. In some implementations, the method further comprises providing a fixture, wherein the fixture is shaped and sized to hold a containment bag and the hammock assembly; and bonding the hammock assembly to an interior surface of the containment bag, wherein the hammock assembly comprises the plurality of film layers, the plurality of segmenting wires, and the return electrode.

Yet another aspect of the disclosure provides a containment bag for extracting a tissue specimen from a patient, the containment bag comprising a flexible container with a top opening and one or more sidewalls, wherein the flexible container comprises one or more layers, and a flexible ring, the flexible ring configured to form the top opening of the flexible container. In some implementations, the flexible ring comprises two ring subassemblies, each ring subassembly comprising a proximal end and a distal end, and a flexible member positioned between and coupled to the distal ends of the two ring subassemblies, wherein the flexible member is movable between a collapsed position and an expanded position. In some implementations, the containment bag further comprises one or more inflatable channels positioned on at least one sidewall of the one or more sidewalls, wherein each of the one or more inflatable channels comprises an inner layer and an outer layer; and at least one port for inflating the one or more inflatable channels, wherein the at least one port is configured to be coupled to a fluid source.

In some implementations, the flexible member comprises a hinge, the hinge having a leading angle that is less than 90 degrees from a central axis of the outer tube.

In some implementations, each of the two ring subassemblies comprises a spring arm. In some implementations, the two ring subassemblies are parallel or substantially parallel to each other when in the collapsed position.

In some implementations, the two ring subassemblies and the flexible member are configured to be disposed in the collapsed position with the containment bag within the outer tube in a first retracted position.

In some implementations, the two ring subassemblies and the flexible member are configured to be pushed into a second advanced position outside the outer tube, and wherein the flexible ring retains the top opening of the containment bag in the open position.

In some implementations, the flexible ring is configured to slide out of the distal end of the outer tube, push the containment bag out of the distal end, move the flexible member to the expanded position, and retain the top opening of the specimen bag in the open position.

In some implementations, the flexible member comprises a spring bias.

In some implementations, the outer tube comprises a trocar. In some implementations, the flexible member comprises a lead-in feature, the lead-in feature comprises a blunt feature (e.g., a blunt tip), wherein the blunt feature is configured to protrude past the distal end of the outer tube when a distal tip pressure is at or above a threshold and retract back into the lead-in feature of the flexible member when the distal tip pressure is below the threshold.

In some implementations, the containment bag comprises a plurality of layers, including at least one electrically insulative layer for providing an electrosurgical effect between the one or more segmenting wires and a return electrode located in an interior of the containment bag.

In some implementations, each of the at least one electrically insulative layer is composed of a high dielectric constant material selected from a group consisting of a polymer film, polyethylene, Polytetrafluoroethylene (PTFE), Ethylene tetrafluoroethylene (ETFE), Polyethylene terephthalate (PET), polyamide, and polyester.

In some implementations, each of the at least one electrically insulative layer comprises a flexible polymer film having a high dielectric constant coating, the high dielectric constant coating selected from a group consisting of a polymer film, polyethylene, Polytetrafluoroethylene (PTFE), Ethylene tetrafluoroethylene (ETFE), Polyethylene terephthalate (PET), polyamide, and polyester.

In some implementations, the containment bag comprises a plurality of layers separated by one or more fluid gaps to provide insulation between an interior of the containment bag and an exterior of the containment bag.

In some implementations, each of the one or more fluid gaps is filled with air, deionized water, or silicone.

In some implementations, the one or more fluid gaps of the containment bag are configured to be filled after the containment bag is positioned in an interior cavity of the patient.

In some implementations, the containment bag comprises a plurality of layers that are welded together (e.g., via thermal sealing). Alternatively, the plurality of layers of the containment bag are adhered or laminated together using a transparent or substantially transparent adhesive.

In some implementations, the plurality of layers of the containment bag comprise layers of different refractive indices arranged to reduce or minimize light refraction between an interior of the containment and an exterior of the containment bag. In some implementations, the plurality of layers of the containment bag are arranged in one of an ascending order of refractive index or a descending order of refractive index from the interior to the exterior of the containment bag.

In some implementations, the one or more segmenting wires include non-uniform surface features for gripping the tissue specimen prior to segmentation and extraction.

In some implementations of the method, providing the hammock assembly comprises providing a platform for holding the plurality of film layers, the plurality of segmenting wires, and the return electrode in position prior to or during the sealing.

In some implementations, the plurality of film layers include at least a return electrode layer for temporarily holding the return electrode, a channel layer for insulating at least a portion of the return electrode and a portion of each of the plurality of segmenting wires, and a perforation layer for temporarily holding the plurality of segmenting wires.

In some implementations of the method, the sealing comprises sealing the plurality of segmenting wires and the return electrode to the plurality of film layers using heat or directed energy.

In some implementations of the method, the bonding comprises bonding the hammock assembly to the interior surface of the containment bag using adhesives and/or thermal sealing.

In some implementations, the fixture comprises one or more of a mechanical alignment tab, a post, and a grasping feature for holding the hammock assembly, the method further comprising (1) loading the containment bag onto the fixture comprising the hammock assembly, and (2) holding the containment bag and the hammock assembly in position prior to the bonding.

In some implementations of the containment bag, the flexible container comprises a base or bottom that is arranged opposing the top opening. In some implementations of the containment bag, the flexible container comprises a cylindrical or hemispherical cross section. In some implementations of the containment bag, the flexible container comprises a plurality of sidewalls positioned between the top opening and the base or bottom of the flexible container.

In some implementations of the containment bag, at least one inflatable channel of the one or more inflatable channels comprises a tufted design (or one or more tufts). In some implementations of the containment bag, at least one inflatable channel comprises one or more sub compartments that are not in fluid communication with each other. In such cases, each sub compartment of the at least one inflatable channel may have a port for inflating the corresponding sub compartment.

In some implementations of the containment bag, at least one inflatable channel of the plurality of inflatable channels is positioned on each sidewall and the base of the flexible container. That is, an inflatable channel may be positioned on (or affixed to) each sidewall of the plurality of sidewalls of the flexible container and the base/bottom of the flexible container.

In some implementations of the containment bag, the flexible container comprises an inner layer and an outer layer. In some implementations of the containment bag, at least a portion of the outer layer of the flexible container forms a portion of the inner layer of each of the plurality of inflatable channels.

In some implementations of the containment bag, the plurality of inflatable channels cover at least 10% of an external surface area of the flexible container. In other implementations of the containment bag, the plurality of inflatable channels are present on only a single side of the flexible container and are not present on the base of the container or are present only on the base of the flexible container.

In some implementations of the containment bag, the inner and outer layers of the plurality of inflatable channels are formed of a different material, have a different thickness, have a different durometer, a different flexibility or elasticity, or a combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

BRIEF DESCRIPTION OF THE DRAWINGS

FIG. 28 illustrates a perspective view of a specimen bag system comprising a specimen bag and a plurality of inflatable channels positioned around a perimeter of the specimen bag, according to various aspects of the present disclosure;

FIG. 29 illustrates a front view of the specimen bag system in FIG. 28, according to various aspects of the present disclosure;

DETAILED DESCRIPTION

Figure 1:
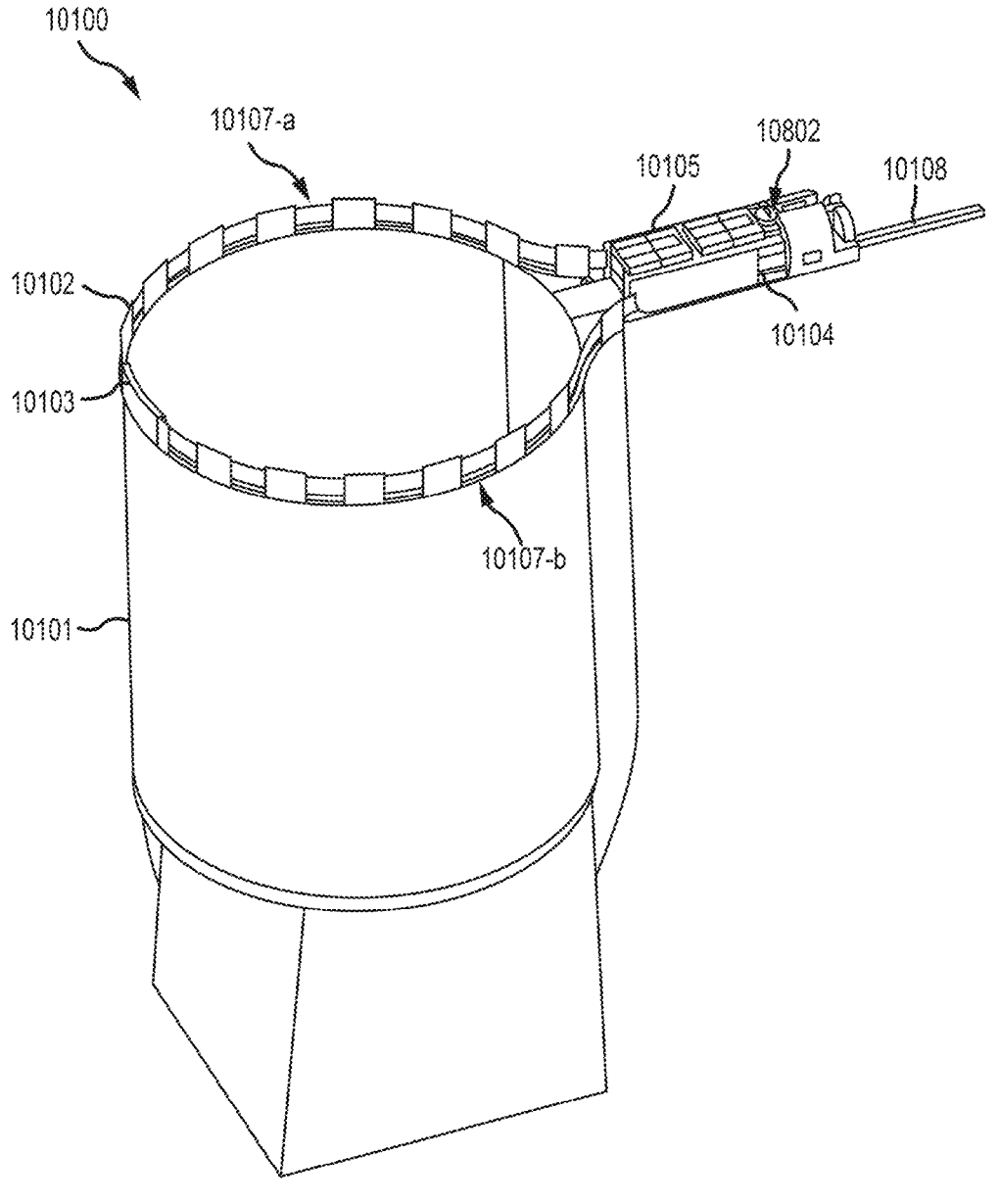
FIG. 1 illustrates an embodiment of a specimen removal bag system with the specimen bag open in accordance with various aspects of the invention.

The present disclosure relates to devices, systems, and methods for removal of biological tissue during surgical procedures. In particular, but not by way of limitation, the present disclosure relates to a specimen or containment bag for removing biological tissue during surgical procedures.

The word "exemplary" is used herein to mean "serving as an example, instance, or illustration." Any embodiment described herein as "exemplary" is not necessarily to be construed as preferred or advantageous over other embodiments.

For the purposes of this disclosure, and when referencing a direction of intended surgery, the terms "front" and "distal" shall refer to a side or direction associated with a direction of intended surgery (i.e., towards the patient body, inside the patient body), while the terms "back", "rear", or "proximal" shall be associated with the intended bracing of the actuator handles (i.e., towards the surgeon or the surgical team). Furthermore, for the purposes of this disclosure, the terms "introducer tube", "insertion tube", and "distal tube" may be used interchangeably and may refer to a tube that is configured to enter the patient cavity through an incision and that is shaped and sized to permit one or more laparoscopic tools to be inserted into the patient incision during a surgical procedure. Furthermore, the term "outer tube" may refer to a tube that is shaped and sized to encase, for instance, a rolled-up containment bag assembly. In some cases, the outer tube is also shaped and sized to receive an inner tube, where the inner tube is used to push the rolled-up containment bag assembly out of the distal end of the outer tube, for instance, to unfurl the rolled-up bag. In some embodiments, the outer tube may be the same or different from the introducer tube. That is, in some cases, the outer tube comprising the rolled-up containment bag also serves as the introducer tube.

The present application for patent is related to U.S. Pat. No. 10,925,665 ('665 patent); U.S. Pat. No. 10,603,100 ('100 patent); and U.S. Pat. No. 10,873,164 ('164 patent) entitled "Large volume Tissue Reduction and Removal System and Method", "Electrosurgical Device and Methods", and "Connector", respectively, assigned to the assignee hereof and hereby expressly incorporated by reference herein. The present application for patent is also related to U.S. Publication No. 2019/0328377 ('377 Publication) entitled "Tissue Specimen Removal Device, System and Method," assigned to the assignee hereof and hereby expressly incorporated by reference herein.

Increasingly, improvements in surgery techniques pertain to reducing the invasiveness of procedures. In particular, surgeons seek to perform "minimally invasive" procedures—meaning that incisions are limited to a particular size—whenever possible. However, many surgeries that can be performed almost entirely via very small incision sites end up requiring a last step that is very difficult to perform via a small incision site. That last step is the removal of excised tissue. Removing large portions of tissue, such as entire uteri, large portions of kidneys, or cancerous tumors, for example, creates a number of logistical challenges. The previous disclosures referenced throughout this present disclosure describe various devices, systems, and methods for segmenting these large pieces of tissue within a specimen bag while still inside the patient. Current approaches allow for the tissue to be segmented into small enough pieces that they can be pulled out one by one through the small incision site.

Several factors can make this process time consuming, difficult, messy, and/or lead to a patient risk. For example, if a portion of the tissue is calcified, currently available cutting devices may take a long time to cut through that portion. In such cases, bringing the tissue close to the top of the specimen bag and cutting it as the tissue is being extracted can take an hour or more, and may require many hands and tools in the area. If the tissue and specimen bag must be manipulated and handled excessively, the opening of the bag may slip back into the incision site. This can be particularly high risk to a patient if the tissue specimen is a cancerous tumor, because such specimens often contain liquid that can spill and spread cancer cells within the patient's body. The present disclosure provides devices, systems, and methods that improve the ease, safety, and efficiency of segmenting a tissue specimen within a specimen bag.

One type of existing specimen bag or containment component system is a flexible material that is rolled or folded by a surgeon, attending surgeon and/or scrub nurse so that it can be inserted through the trocar or incision site and then opened once inside the patient's body. In this type of system, the surgeon first excises the tissue to be removed, and then manipulates the bag opening with laparoscopic tools in order to place the tissue specimen within the bag. After capture of the tissue, the bag opening is raised with laparoscopic graspers and led out of the incision site to be secured externally by the surgeon by hand or with the addition of Kelly clamps or snaps.

Some of these types of specimen bags incorporate a polymer ring that is formed or attached to the top of the bag to keep the bag opening biased to a fully open position. This polymer ring can help hold the exteriorized bag open and in an appropriate place so that it does not fall back into the peritoneum or other surgical site of a patient.

Another common type of specimen bag or containment component system uses a bag that is typically placed within a cannula or lumen for insertion into the peritoneum through a trocar or incision site and the specimen bag advances beyond the cannula to access the opening.

Many specimen bag systems use a mechanical means to bias the bag opening to an extended position to assist the surgeon in placing the tissue specimen within the bag. Such systems may comprise a formed metal ring with a spring bias attached to the top of the specimen bag so that the spring bias opens the top of the specimen bag when it is outside of the cannula. Most of the systems that use a metal ring of this type also incorporate a string or suture material as a draw-string to close the bag opening for exteriorization. In these devices, the string may remain outside of the patient's body and may be pulled to seal the bag. This string closes the opening while the metal ring is retracted back into the cannula leaving the bag free from the cannula and metal rings and also leaving the bag within the incision site after the cannula and metal ring are withdrawn. Then, the surgeon can use the string to pull the bag opening through the incision site. Other systems use a string or suture material as a drawstring that closes the bag opening and while doing so, tears the bag away from the metal ring, leaving the bag free from the metal rings and cannula. The string is then used to retrieve the bag opening through the incision site.

In one non-limiting example, a metal ring subassembly comprised of two halves of a metal ring may be utilized to aid in the closing of the formed metal ring attached to the top of the specimen bag, further described below in relation to FIGS. 1, 18, and 19. In some embodiments, the distal interface point between the two metal ring halves may be connected by a flexible member (e.g., flexible member 1041). In some circumstances, this flexible member allows the spring biased metal ring to be compressed into a nearly flat configuration such that the two halves of the spring biased metal ring are parallel or substantially parallel to each other. According to aspects of this disclosure, this flexible member 1041 may be created in a variety of methods that may facilitate in retention of the distal ends of the spring biased metal rings (also referred to as spring arms, such as spring arms 1021 in FIG. 18). Some non-limiting examples of manufacturing techniques utilized for the flexible member may include manufacturing the flexible member from a flexible film (i.e., heat shrink), using a machined subassembly with an incorporated flexible hinge at the distal ring tip, or using an injection molded living hinge feature (i.e., an integral hinge made from the same material as the two pieces it connects) which allows the metal ring assembly to hinge freely at this distal tip over the life of the product. In some cases, for instance, with the metal ring subassembly (e.g., spring arms 1021) in the compressed state, the containment bag subassembly may be configured to be rolled into a smaller diameter configuration which may facilitate placement through a patient incision. In some embodiments, this compressed and/or rolled containment bag assembly may be loaded into an outer tube (e.g., a thin-walled outer tube), an introducer tube, a cannula assembly, or a trocar, which may aid in one or more of: product shipment, bag management during loading and/or deployment through a patient incision.

As previously described, the currently available specimen retrieval pouches are designed to contain tissue while a surgeon loads and subsequently exteriorizes the specimen bag. The Tissue Specimen Removal system described in the patents mentioned and incorporated above utilize tissue segmentation devices comprising wires, a return electrode, and other components. The Tissue Specimen Removal system of the present disclosure may integrate various tissue segmentation device components—for example, segmenting wires and a return electrode—and further include one or more "connectors." The term "tissue segmentation device components," or simply "segmenting components," may refer to any type of cutting device that is configured to physically cut tissue. Often, these segmenting components comprise individual wires or wire loops, which cut tissue by being drawn through it by mechanical force, or with the assistance of RF energy, or with a combination of the two. However, any segmenting components described herein may include those referenced in each of the patents incorporated above, any referenced throughout this disclosure, or any other types of tissue cutting device known or yet to be created. In many embodiments, these segmenting components may be integrated into the specimen bag of the present disclosure prior to being deployed inside a patient. Examples of such specimen bags having integrated segmenting components (e.g., segmenting wire loops) are described later in this disclosure. It should be noted that, the specimen bag may or may not comprise a return electrode (e.g., integrated in the bag). Furthermore, when RF energy is utilized for specimen division, it may be applied in a bipolar or monopolar fashion. If bipolar, no return electrode may be needed.

The term "connectors" may refer either to a connector housing comprising one or more connector pins, or to individual connector pins themselves. The "connector pins" may be referred to as "connector portions." These connectors attach to, at one end, segmenting components within the specimen bag. The connectors are configured to allow later connection of a separate portion of a segmentation device. For ease of reference and differentiation between tissue segmentation device components, and this separate, connectable portion, the latter may be referred to herein as "connectable (tissue segmentation) equipment" or "a piece of connectable equipment." For example, the connectable equipment may be a tensioning mechanism assembly configured to tension the segmenting components (cutting devices or segmenting wires) against the tissue specimen in preparation for drawing them through the tissue. The connectable equipment, in embodiments, may apply the required force and radio frequency (RF) energy to the segmentation components and carry the return current back to the RF generator. As such, a specimen bag of the present disclosure, which integrates connectors, segmentation wires, and a return electrode may have additional components not required for passive specimen retrieval pouch applications, as the dividing of tissue in those instances is done by the surgeon using separate tools not integrated with or connected to the bag.

In devices of the present disclosure, which comprise specimen removal bags that may be connected with connectable tissue segmentation equipment, the components associated with the connectors are not required for the loading of the tissue, nor are they required during exteriorization. The devices and systems of the present disclosure includes these connectors because it is highly advantageous to integrate the one or more mechanisms for connection of tissue segmentation equipment (i.e., the connectors) into a tissue specimen collection bag itself. In particular, when collected tissue specimens need to be segmented while retained inside a specimen bag, it can be advantageous to a surgeon to be able to connect the segmenting components (e.g., segmentation wires or other cutting devices) quickly and easily to connectable tissue segmenting equipment (e.g., a tensioning device). Being able to activate and use the segmenting components quickly can save valuable time in critical moments after tissue mobilization. In some embodiments, the segmenting components comprise a plurality of wire loops or segmenting wires integrated with the bag. Having the ends of these segmenting wires managed and out of the way, but then readily accessible once needed, is highly desirable. This can reduce the time spent retrieving additional instruments and reduce risks associated with setting equipment down and picking it up multiple times. Therefore, the integrated connector system of the present disclosure provides several conveniences and advantages.

Figure 18:
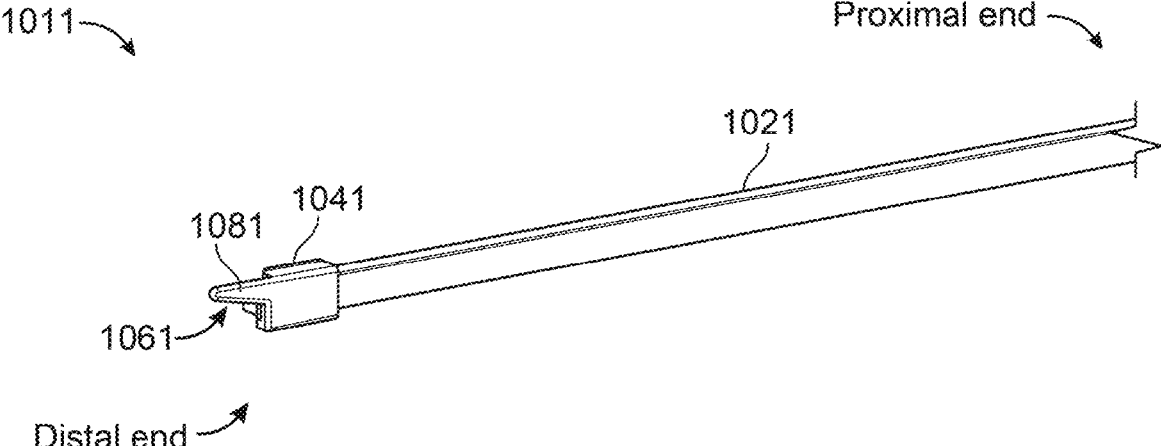
FIG. 18 illustrates an example of a spring arm system in a collapsed position, where the spring arm system may be used for controlling the opening and closing of a specimen bag, according to various aspects of the present disclosure.

FIG. 18 illustrates an example of a spring arm assembly 1011 of a containment bag assembly, where the spring arm assembly 1011 can be used to deploy a rolled-up containment bag (not shown) in a patient incision, according to various aspects of the disclosure. In some cases, the spring arm assembly 1011 and the rolled-up containment bag assembly are shaped and sized to fit within an outer tube or a trocar assembly. Once the outer tube or trocar assembly is inserted into the patient incision, the spring arm assembly 1011 can be moved to an expanded position and the rolled-up containment bag assembly can be unfurled, in which case the spring arm assembly 1011 forms the top opening for the specimen bag. FIG. 18 illustrates the spring army assembly 1011 in its collapsed position, while FIG. 19 illustrates the spring arm assembly in an expanded position. Additionally, FIG. 1 depicts a spring arm assembly and a specimen bag extending downward from the spring arm assembly, where the specimen bag is in a ready position to receive a tissue specimen.

In some cases, a rolled-up containment bag assembly may be pushed through the distal end of an outer tube or trocar for expanding the containment bag opening so it can receive a tissue specimen. In some cases, the outer tube or trocar is shaped and sized to receive an inner tube, where the inner tube is utilized to push the rolled-up bag out of the distal end of the outer tube. As noted above, the spring arm assembly 1011 helps form a rigid or substantially rigid top opening of the specimen bag, which allows the specimen bag to be kept open when in the patient incision. The spring arm assembly 1011 comprises a plurality of spring arms 1021, a flexible member 1041 for coupling the spring arms 1021 at their distal end, and a lead-in feature 1081 at a distal end 1061 of the flexible member 1041, where the lead-in feature 1081 is configured to protrude distally from the rolled containment bag assembly and past an outer tube or trocar. In some cases, the lead-in feature 1081 may comprise a spring-loaded retractable blade, a blunt lead-in feature, and/or a hinge, to name a few. This retractable blade (i.e., lead-in feature 1081) may be configured to protrude under distal tip pressure, for instance, the pressure used to press the rolled-up containment bag assembly against the patient skin. In some aspects, this blade (e.g., blade portion of lead-in feature 1081) may aid in creating a patient incision concurrently with the placement of the rolled containment bag subassembly. In some cases, once pressure on the distal tip is relieved, the distal blade may be configured to retract back into the lead-in feature 1081 on the flexible member 1041. In some embodiments, the containment bag assembly may be configured to be deployed, loaded with a tissue specimen, and retracted back through the trocar assembly and/or outer tube. In some cases, the outer tube of the trocar may be configured to be removed prior to exteriorization of the containment bag opening.

Figure 19:
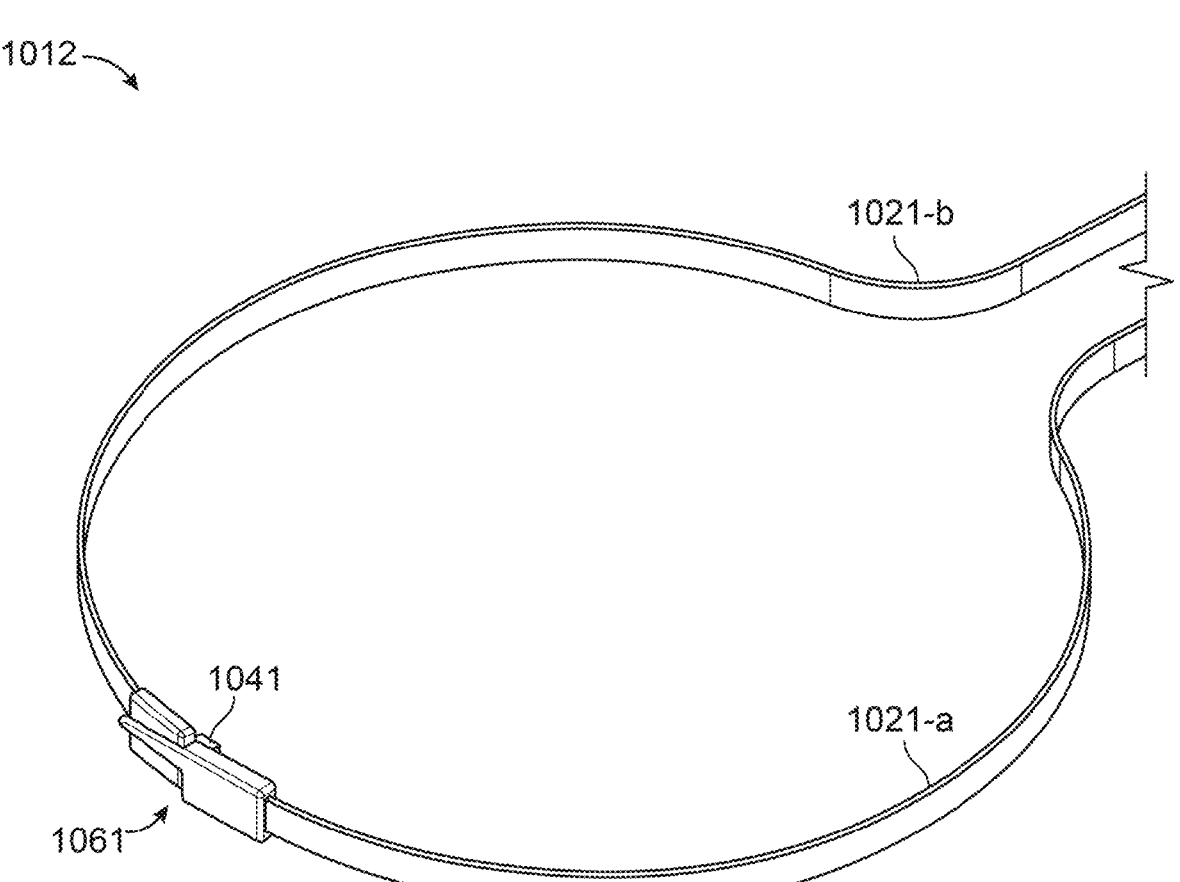
FIG. 19 illustrates the spring arm system of FIG. 18 in an expanded position, according to various aspects of the present disclosure.

FIG. 19 illustrates a detailed view 1012 of a top portion of a containment bag assembly in its expanded position, according to various aspects of the disclosure. FIG. 19 illustrates one or more aspects of FIG. 18 and shows the spring arms 1021 and flexible member 1041 of the spring arm assembly 1011 previously described in relation to FIG. 18. In this example, the spring arms 1021 curve outward from the outer tube or trocar, which expands the top opening of the containment bag (shown in FIG. 1). In some cases, the containment bag assembly comprises a containment bag (not shown) and a plurality of spring arms 1021 (e.g., spring arms 1021-*a*, 1021-*b*), where the spring arms 1021 form a top opening of the specimen/containment bag. As seen, the spring arms 1021-*a*, 1021-*b* are coupled at their distal ends 1061 with a flexible member 1041. The flexible member 1041 may be similar or substantially similar to the flexible member 1041 previously described in relation to FIG. 18. In some cases, the spring arms 1021 (e.g., spring arms 1021-*a*, 1021-*b*) are configured to extend out of the distal end of an outer tube when in the expanded position. In some embodiments, the spring arms 1021 are securely held at their proximal end (shown in FIG. 1).

In some embodiments, a leading angle (e.g., <90 degrees) from the outer tube central axis may be added to the outer tube. In one non-limiting example, the flexible member 1041 comprises a lead-in feature 1081 (also referred to as a blade 1081 or a hinge 1081) with a leading angle that is less than 90 degrees from the outer tube central axis. This leading angle facilitates in the initial placement of the outer tube through the potentially misaligned layers of the patient incision. In some other cases, a small lead-in feature on the flexible member may be created, where the lead-in feature is designed to protrude distally from the rolled containment bag subassembly (or spring arm assembly 1011 of the containment bag subassembly) and past the outer tube. In some examples, this lead-in feature may also facilitate the initial placement of the outer tube through the patient incision. For instance, as seen in FIG. 19, the flexible member 1041 comprises a spring bias (i.e., lead-in distal hinge 1081) for opening the top of the specimen bag and expanding the spring arms 1021 as it is pushed past the distal end of the outer tube.

In some circumstances, a containment bag procedure may prioritize small incision size. According to aspects of this disclosure, a detachable spring assembly may serve to reduce the diameter of the rolled-up containment/specimen bag, and thus incision size, as compared to currently used techniques. As discussed above, the opening of the containment bag may incorporate expanding spring arms 1021 that allow the opening of the bag to be held open throughout the procedure. In some embodiments, once the containment bag has been loaded with the tissue specimen and its opening exteriorized, the spring arms 1021 may be positioned outside of the patient incision. In one non-limiting example, this can be accomplished by adding small holes around the top of the containment bag so that hook like features can be used to connect the bag opening to the spring arms 1021. Other applicable techniques for attaching the spring arms 1021 outside the patient incision are contemplated in different embodiments, and the examples listed herein are not intended to be limiting.

Deploying Instrument (DI) as the Trocar

In many laparoscopic procedures a surgeon may wish to place surgical instruments (e.g., segmenting wires, grasper, scissors, etc.) through a patient incision using a trocar. In some circumstances, trocars allow for a tight pneumatic seal of the patient incision while surgical instruments are passed freely through the trocar central shaft. In some cases, trocars also comprise an auxiliary port to allow for patient cavity insufflation using carbon dioxide ($CO_2$) gas. In one embodiment of a rolled bag subassembly to be placed in an outer tube—the outer tube can be replaced with a subassembly of components which function like a trocar. As noted above, in some embodiments, the trocar outer tube may be configured to be removed prior to containment bag opening exteriorization.

In another embodiment, the containment bag opening may be configured to remain inside the patient incision or cavity. For instance, in one non-limiting example, the bag opening may be retracted back to the distal tip of the trocar after the containment bag is opened and loaded inside the patient cavity. In some instances, a pneumatic sealing and/or connection feature is used to retain the specimen bag opening (e.g., formed by the spring arms 1021 in FIG. 19) at a location just outside or inside the distal tip of the trocar. In some examples, the trocar is configured to be removed and the containment bag opening is configured to be exteriorized after the tissue specimen is segmented and prior to tissue segment removal.

In some cases, tissue specimen removal systems may be configured to reduce a large volume tissue specimen in size so that smaller pieces can be removed through an access port in the patient during minimally invasive surgery. In some cases, tissue specimen removal systems may employ a device, for instance, for introducing and deploying a specimen bag to capture and contain the tissue specimen during the procedure. Tissue specimen removal systems may also employ one or more RF electrosurgical generators. In some examples, the device may be adapted to segment the tissue specimen through RF energy-charged wires, where the RF energy is received from one or more RF electrosurgical generators (or simply, generators), described in further detail below. In some cases, the generator(s) may be set at the nominal power setting needed for tissue segmentation. The range of power settings may be determined based on the exposure size, or surface area between the tissue specimen and RF cutting wire. In one non-limiting example, the RF power used for tissue segmentation may be in the range of 60 to 400 Watts. In some instances, the RF energy or power is applied in a bipolar fashion, which helps prevent the current from being delivered to adjacent tissue structures. Containment of the tissue specimen in an insulative specimen/containment bag may serve to add additional electrical isolation of the tissue specimen from the rest of the patient. In some embodiments, the RF generator may provide adjustments of amplitude or duty cycle of the output current, based at least in part on the current delivery and impedance observed during initiation and sustainment of the cut.

In some circumstances, the containment bag provides an electrosurgical effect between the wires (active electrodes) and the return electrode located in the inside surface of the bag, the distal end of the segmentation tube (i.e., introducer/insertion tube) or other intermediate locations within the bag, etc. As the specimen bag is suspended in the peritoneum during segmentation, leakage currents may be observed outside of the specimen bag (e.g., in tissue in contact with the bag), which may create alternative site tissue heating if the leakage currents exceed a threshold. In addition, as the electrosurgical output contains a high voltage, a dielectric breakdown of the bag can also result in tissue damage where a breakdown or arc event occurs.

In some embodiments, the possibility of breakdown or alternate leakage current paths may be eliminated or reduced by using one or more of (1) a layer of material that surrounds the tissue, and (2) active and return electrodes comprising a dielectric withstand that is above a threshold voltage (e.g., the maximum voltage observed during the segmentation process). This dielectric withstand protects against dielectric breakdown and reduces the amount of leakage current by changing the capacitive coupling between the energized bag components and ground. As can be appreciated by those familiar with international safety standards, such as IEC 60601-1 or IEC 60601-2-2, this dielectric withstand requirement may exceed the maximum voltage by an additional margin required by the segmentation system per its insulation diagram, commonly 1 kV or more above this maximum observed voltage. Additionally, or alternatively, this dielectric withstand may be selected to not only exceed the maximum voltage observed in the segmentation process but to also exceed the maximum voltage generated by electrosurgery that may occur outside of the bag in which the bag may be exposed, such as, but not limited to, spray coagulation used at other patient incision sites. In some aspects, such a design serves to reduce the likelihood of a breakdown in the bag that would otherwise be undetected by the user (e.g., surgeon) or the segmentation system.

In some embodiments, this dielectric withstand may be created using a bag material having a high dielectric constant (e.g., above a threshold, where the threshold is 2.0) which serves to create an electrical insulation around the entire contents or substantial portions of the specimen/containment bag. Some non-limiting examples of the bag material may include polymer films made of materials with known high dielectric constants like polyethylene, PTFE, ETFE, PET, polyimide, polyester, or any other high dielectric constant film. It should be noted that more than one layer of the same or a different high dielectric constant material may be utilized in some embodiments. For instance, while some of the polymer films described above provide adequate dielectric withstand, they may have mechanical properties that are not desirable (e.g., when used as a single layer), such as lack of flexibility, lack of stretchability, lack of ability to be rolled into a small lumen for deployment, and/or low abrasion or tearing resistance. In such cases, these tradeoffs may be offset by using multiple layers (i.e., of the same or a different material). Such a design may serve to reduce the dielectric withstand requirements of an individual layer by distributing the dielectric withstand over the multiple layers to achieve the total dielectric withstand needed, while at the same time, allowing more flexibility with respect to using a single layer. One non-limiting example of such a bag comprising electrical insulation properties is described below in relation to FIGS. 28-36.

In some other cases, a high dielectric withstand coating on a flexible polymer film may be used to create this dielectric withstand. The high dielectric withstand coating may be composed using similar materials described above, such as, but not limited to, polyethylene, Polytetrafluoroethylene (PTFE), Ethylene tetrafluoroethylene (ETFE), Polyethylene terephthalate (PET), polyamide, and polyester. Additionally, or alternatively, the high dielectric withstand coating may be used in conjunction with the substrate material (e.g., flexible polymer film) to provide the combined desired dielectric properties.

In yet other cases, high dielectric material films, coatings, and/or solids may only be applied to areas of substrate films where potential patient or user contact can result in a site burn (e.g., at the same or an alternate incision site). In some aspects, such selective application of high dielectric materials to substrate films may serve to reduce manufacturing cost, simplify the manufacturing process, etc. In some cases, the areas of the substrate films to which the high dielectric materials are applied may be determined based on the travel of the energized components (e.g., active electrodes, segmenting wires carrying RF energy, to name two non-limiting examples) within the bag during use. For instance, in one non-limiting example, high dielectric materials may be utilized on the bottom and lower sides of the specimen bag where segmenting wires may travel, at or near the return electrode, and/or where the surgeon holds the bag during use, but not the intermediate portion where the wires will not travel and/or where the return electrode will not be located.

Figure 13:
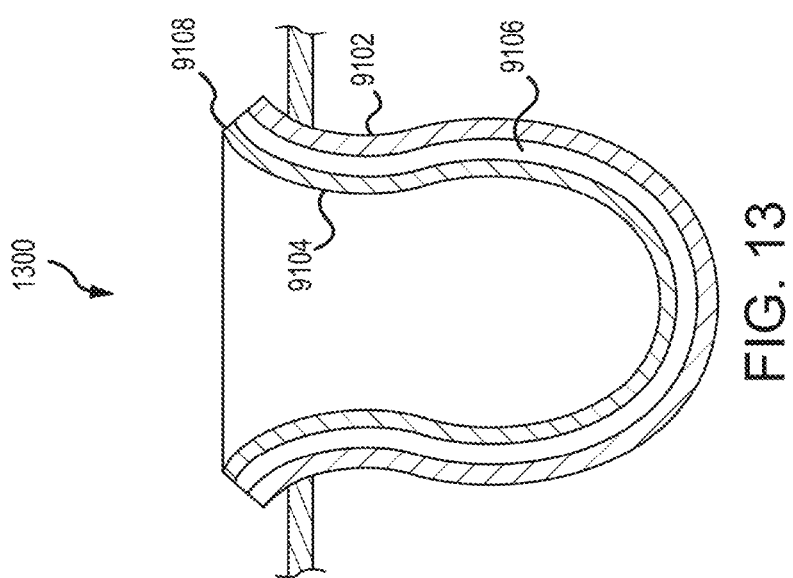
FIG. 13 is a cross-section view of some components of a bag assembly with leak detection, according to various aspects of the present disclosure.

In still other cases, an additional method to provide insulation may comprise providing an air gap between film layers of the specimen bag, as described in relation to FIG. 13. Additionally, or alternatively, insulation may be provided using one or more channels (e.g., inflation channels), as described in relation to FIGS. 28-36, 38A-38I, and/or 41A-41B. In such cases, the air gap or spacing (e.g., intermediate space 9106) may acts like an insulator, for instance, between the interior layer which may be intimate to the RF energy and the outer layer which may be in contact with the patient. In some embodiments, this air gap (i.e., intermediate space 9106) may be created naturally with features of the bag to provide a known separation. Alternatively, this gap may be created with a positive pressure by inflating the area between the film layers with a fluid, air, or another gas. In some examples, the area may be filled with a liquid solution, such as deionized water, or a material that flows, such as a silicone that increases the dielectric properties and provides the required dielectric withstand. In some cases, the air or fluids may be applied after the bag is positioned (i.e., for ease of manipulation) and prior to the application of RF energy. In some cases, these materials may be aspirated after the use of RF energy, which may serve to ease removal of the specimen/containment bag after use.

Electrode Wire Grasping Features

In some cases, for instance, for actuator systems which use electrode wires in combination with mechanical tension, the ability of the wire to initially grasp the surface of the tissue specimen may aid in tissue segmentation, or prevent the wire from slipping around the tissue before cutting. In such cases, a lower initial pretension force (i.e., prior to actual segmentation) may be used to assist the segmenting/cutting wire in grasping the surface of the tissue specimen. According to aspects of this disclosure, surface treatments or features may be added to electrode/cutting wires, such as wires 10428 in FIG. 23, to encourage grip between the wire(s) and the tissue specimen. In some other cases, barbs and/or other non-uniform surface features may be provided to enhance the grip between wires and tissue specimens.

Additionally, or alternatively, a coagulation or low amplitude cutting waveform may be utilized to encourage a wire to stick to (or grip) the surface of the interfacing tissue through desiccation between the tissue and wire interface. In some cases, a coagulation waveform may be used, initially, for each of the electrode wires (e.g., electrode wires 10428). In other cases, coagulation waveforms may be used for only a portion of the electrode wires. In yet other cases, coagulation waveforms may be used in conjunction with the surface treatments/features described above to help the wires grip the tissue specimen. Alternatively, the wire channels holding and attaching the wires to the bag may be semi-detachable such that the wire perforation channel (shown as perforation layer 10441 in FIG. 21B) is attached to the bag but allowed to pull away from the bag in areas along the length of the wires. This helps hold the wires in place on the tissue until segmentation is initiated (e.g., mechanically or via application of RF energy).

Containment Bag Return Electrode and Wire Pattern Assembly Hammock

For a containment bag which incorporates several internal components for subsequent tissue division, a method to manufacture subassemblies of these internal components is provided, which may serve to streamline manufacturing by reducing assembly times and potential scrap costs, to name two non-limiting examples. Furthermore, a method for manufacturing a containment bag incorporating a pattern of pre-placed wires (e.g., active electrodes, segmenting wires) and/or additional return electrode(s) is discussed. Specifically, aspects of this disclosure relate to a method for manufacturing a subassembly (e.g., wire subassembly 1044 in FIGS. 21A and 21B) comprising a pattern of pre-placed electrode wires and/or return electrodes and adding this subassembly to a standalone bag. In some examples, this wire subassembly 1044 may also be referred to as hammock assembly 1044 since this subassembly may be configured to be placed on, or just above, the floor of a specimen bag 1062 (i.e., like a hammock hanging between two trees). In some embodiments, the hammock assembly 1044 comprises a plurality of film layers, such as, but not limited to, a return electrode layer 10444, a wire channel layer 10443 to selectively insulate at least a portion of the return electrode layer 10444, one or more active electrode wires 10442 (or active electrode wires 10428 in FIG. 21A), and/or a perforation layer 10441. In some cases, the film/perforation layer 10441 may be used to temporarily hold the pattern of wires (e.g., active electrode wires 10442) into their respective positions before sealing the hammock assembly 1044 to the interior surface of the bag 1062.

Flat Seal with Return and Wires in Place

Figure 20:
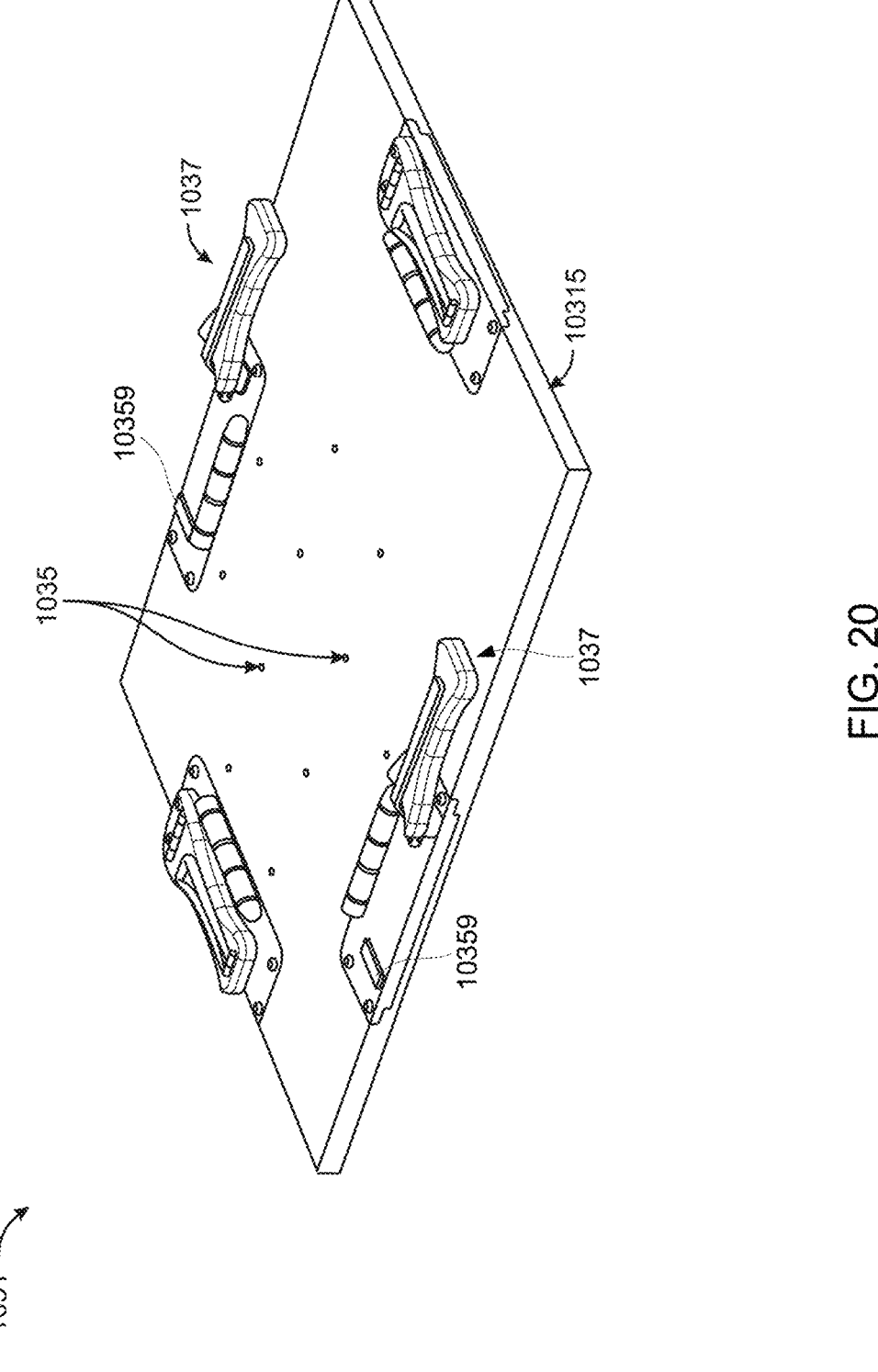
FIG. 20 illustrates an example of a hammock assembly sealing fixture for manufacturing a specimen bag system, according to various aspects of the present disclosure.

According to aspects of this disclosure, a method for manufacturing the hammock assembly is provided. FIG. 20 illustrates an example of a sealing fixture 1031 that may be used for sealing a wire/hammock assembly (e.g., wire or hammock assembly 1044) to a specimen bag (e.g., specimen bag 1062), in accordance with one or more implementations. In some cases, the hammock assembly may comprise a platform 10315 configured to hold a plurality of layers (e.g., layers 10417, 10416 in FIG. 21A; layers 10441, 10442, 10443, 10444, 10445, and/or 10446 in FIG. 21B) in position using at least one mechanical means. In one non-limiting example, the plurality of layers may be held in place using a platform post/film layer hole configuration. In this case, the wires 10428 (also shown as active electrode wires 10442 in FIG. 21B) may be held under tension by one or more features in the platform 10315, which may allow the wires 10428 to rest in their desired locations. In some embodiments, the wire ends may be held under tension with the help of one or more magnetic strips 10359 on a clamshell lid 1037, for instance. Other types of lids besides clamshell lids (e.g., clamshell lid 1037 in FIG. 20) are contemplated in different embodiments, and the examples listed herein are not intended to be limiting. In some cases, once all or a majority of the layers (e.g., channel layer 10417, return layer 10416 in FIG. 21A) are held in place, they may be sealed together thereby welding at least a portion of the layers together at controlled points. In one non-limiting example, the layers may be sealed together using heat or directed energy, although other sealing means (e.g., adhesives) known in the art are contemplated in different embodiments. In some embodiments, a channel layer (e.g., inflation channel layer 10445) on the other side of the hammock may be attached separately or simultaneously.

Figures 21A, 21B:
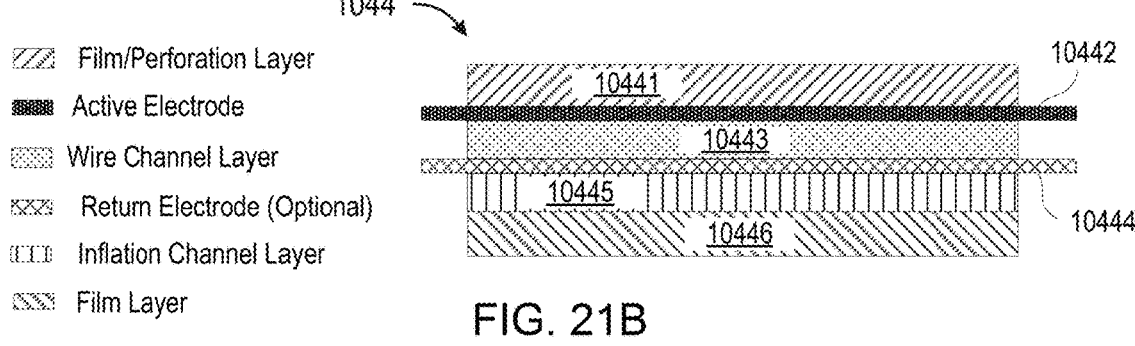
FIG. 21A is an example of a sealed hammock showing one or more wire electrodes, according to various aspects of the present disclosure.
FIG. 21B illustrates an example of a hammock assembly comprising a plurality of layers, according to various aspects of the disclosure.

FIG. 21A illustrates an example of a hammock assembly 1044 comprising a plurality of film layers (e.g., channel layer 10417, return layer 10416) and one or more wire electrodes 10428, according to various aspects of the disclosure. Once sealed, the one or more wire electrodes 10428 may be positioned within channels, where the channels are formed by the addition of a film/perforation layer (e.g., perforation layer 10441 in FIG. 21B) over the wires 10428. As described above, a sealing fixture (e.g., fixture 1031 in FIG. 20) may be utilized to position the plurality of film layers and wire electrodes. Once in position, heat or directed energy is applied to seal the various film layers and the wire electrodes together to form the hammock assembly 1044. The wire electrodes 10428 may comprise one or more active electrodes, shown as active electrodes 10442 in FIG. 21B. An optional return electrode 10444 may be utilized, for example, when RF energy is applied in a monopolar fashion. In some other cases, one of the wire electrodes 10428 may comprise a return electrode, in which the return electrode 10444 in FIG. 21B may be optional. In some embodiments, in a bipolar configuration, the wire electrodes 10428 may comprise one or more active and return electrodes, such that the return electrode (e.g., return electrode 10444) on the hammock assembly 1044 may not be needed. Similarly, in an alternate embodiment, the return electrode may not be needed if the segmenting wires only use mechanical energy to segment tissue. Once sealed, this wire hammock assembly 1044 acts as a monolithic structure that can be connected to the one or more interior layers of a specimen/containment bag, as further described in relation to FIGS. 23 and 24.

In some examples, aspects of this disclosure facilitate in assembling a containment bag having a plurality of wires (e.g., active electrodes 10442), where the plurality of wires are arranged in a pre-placed pattern. In some cases, the geometrical pattern of wires in the hammock assembly 1044 can be designed to approximate a 3D tissue resting inside of a manufactured flat 2D bag. Alternatively, a 3D bag can be constructed to anticipate the shape that a bag will take with the insertion of a tissue specimen. In some circumstances, a 3D bag construction may behave more predictably than its 2D counterpart with the tradeoff being a higher manufacturing cost. In some cases, aspects of this disclosure relate to a method for sealing a flat 2D bag into a simulated 3D bag shape, as described below.

Figure 22:
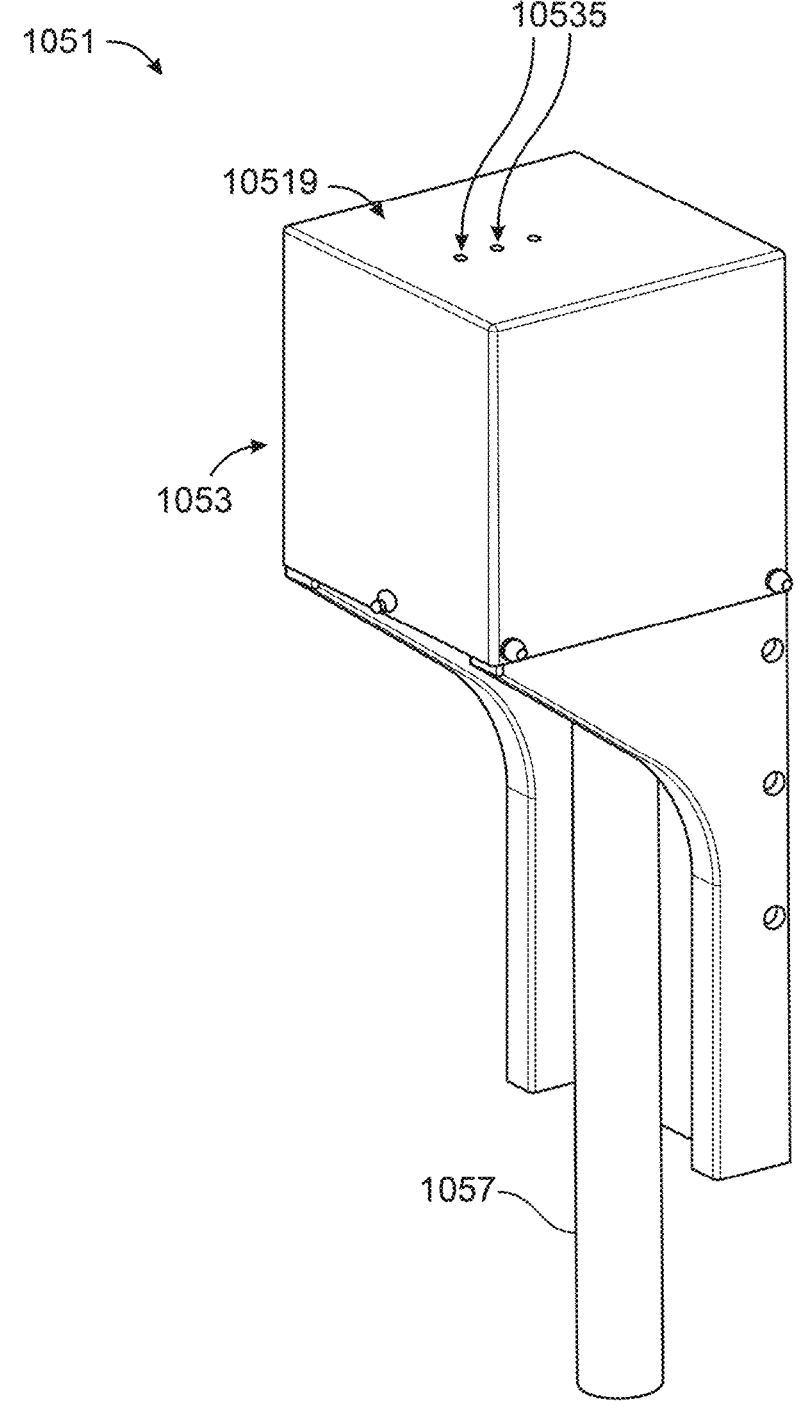
FIG. 22 illustrates one example of a fixture that may be used for manufacturing a specimen bag system, according to various aspects of the present disclosure.

Turning now to FIG. 22, which illustrates an example of a fixture 1051 used to manufacture a specimen bag assembly, according to various aspects of the present disclosure. In this example, the process begins with a specimen bag (e.g., specimen bag 1062 in FIG. 23) and the fixture 1051. Here, the fixture 1051 is generally square shaped (e.g., square shape 1053) or lollipop shaped (e.g., if the fixture comprises the post 1057 extending downward from the square shaped portion 1053), although this is in no way intended to be limiting. In other words, different types of fixtures having different shapes are contemplated in different embodiments and FIG. 22 illustrates one such example of a fixture that may be utilized for manufacturing a specimen bag assembly. While not necessary, the specimen bag (e.g., specimen bag 1062 in FIG. 23) may comprise a bottom (e.g., flat bottom, base) and an opening, where the opening is positioned opposite the bottom. In some aspects, the shape of the fixture 1051 may be based in part on the shape of the specimen bag. In this case, a generally square shaped fixture is utilized since it provides substantially flat surfaces for sealing and welding during manufacturing. The use of a square shaped fixture allows the base of the specimen bag to remain flush or substantially flush with a top face 10519 of the fixture 1051, which provides structural integrity when the wire/hammock assembly (e.g., hammock assembly 1044) is sealed to the interior of the bag. In some cases, the top face 10519 of the fixture 1051 may be shaped and sized to allow the bottom of the specimen bag to remain substantially flat (i.e., with minimal crimping, drooping, etc.) when the bag is pulled over the fixture 1051. It should be noted that, other shapes of fixtures and specimen bags are contemplated in different embodiments, and the examples listed herein are not intended to be limiting. For example, the fixture and/or specimen bag may comprise a cylindrical cross-section in some embodiments. Alternatively, the fixture and/or specimen bag may comprise a hemispherical cross-section in some embodiments. For instance, the fixture may resemble a hemisphere (or inverted bowl) and the specimen bag may also resemble a hemisphere with no defined base or flat bottom. In some cases, the specimen bag comprises an opening, a bottom arranged opposite the opening, and at least one sidewall positioned between the opening and the bottom.

As seen, the fixture 1051 comprises a top end and a bottom end, where the top end comprises the top face 10519 and a square shaped portion 1053 extending downward from the top face 10519. Further, the fixture 1051 comprises a post 1057 that extends downward from the square shaped portion 1053 towards the bottom end of the fixture 1051. In some examples, the fixture 1051 includes a plurality of holes 10535 along its top face 10519. The holes may allow captured air (if any) to vent, which facilitates a more intimate placement of the hammock assembly 1044 on the fixture 1051.

Figure 23:
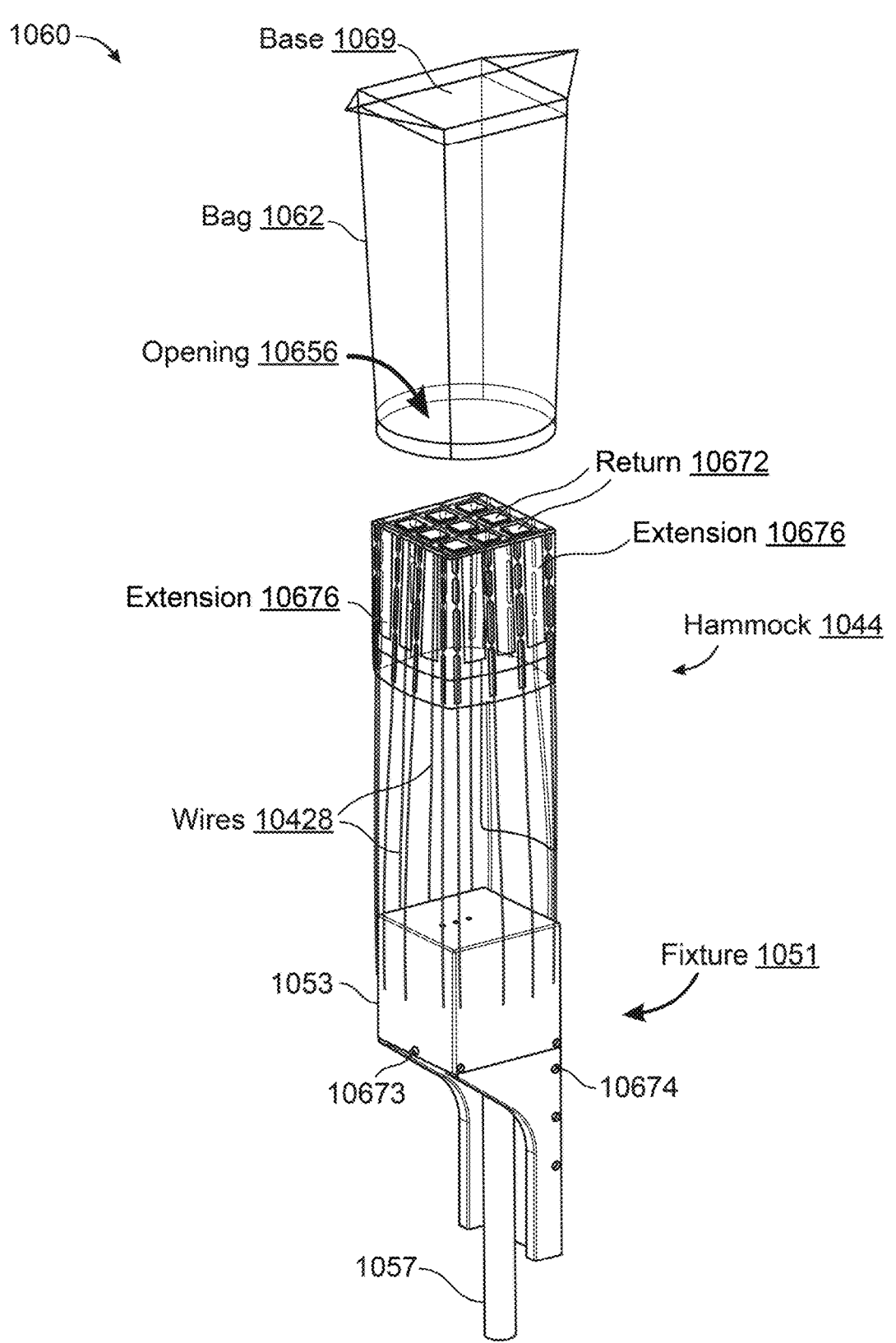
FIG. 23 illustrates an exploded view of a specimen bag system showing a fixture, a hammock assembly comprising a plurality of wire electrodes, and a specimen bag, according to various aspects of the present disclosure.

FIG. 23 illustrates an example of a process flow 1060 directed to manufacturing a specimen bag assembly, in accordance with one or more implementations. Broadly, manufacturing the specimen bag assembly comprises positioning a fixture 1051 (e.g., by holding the post 1057 at the bottom end of the fixture, or securing the post 1057 in a receiving hole, to name two non-limiting examples), positioning a hammock assembly 1044 onto a top face of the fixture, pulling a specimen/containment bag 1062 (or an inner bag layer of a multi-layer specimen bag) over the hammock assembly and the fixture 1051 such that at least a portion of the hammock assembly is positioned between the base 1069 of the bag 1062 and the top face of the fixture, sealing the hammock assembly to an interior layer or surface of the specimen bag 1062, and removing the fixture 1051.

In some examples, a hammock assembly 1044 is bonded to an interior of the specimen/containment bag 1062. In some cases, sealing the hammock assembly to the interior layer or surface of the bag 1062 comprises sealing the hammock assembly to one or more of the bottom of the interior layer (or bottom of the bag) and at least one sidewall of the interior layer (or bag). In some cases, specimen/containment bag 1062 in FIGS. 23 and/or 24 may comprise the specimen bag, or alternatively, an inner layer of a multi-layer specimen bag.

The hammock assembly 1044 depicted in FIG. 23 may be similar or substantially similar to the hammock assembly 1044 described above in relation to FIGS. 21A and/or 21B. As seen, the hammock assembly 1044 conforms to the generally square shaped portion 1053 of the fixture 1051. More specifically, but without limitation, the hammock assembly 1044 takes on a 3D shape when it is placed over the fixture 1051. Once pulled down over the fixture 1051, the hammock assembly 1044 comprises at least (1) a base, where the base further includes the return 10672, and (2) a plurality of extensions 10676. As seen, the wire electrodes 10428 (e.g., active electrode wires) of the hammock assembly 1044 extend down the sides of the square shaped portion 1053. In some cases, the hammock assembly 1044 further comprises a return electrode 10672 having a plurality of extensions 10676. These extensions 10676 are located between the active electrode channels comprising the wires 10428 and are electrically connected (e.g., by a ring, such as ring 3423 in FIG. 9) at or near a distal portion of the hammock assembly 1044. That is, these extensions 10676 located between the active electrode channels are extensions of the return electrode 10672.

In some cases, at least a portion of the wire electrodes 10428 may be positioned between various film layers of the hammock assembly 1044, for instance, near the base or along the sides of the hammock. Furthermore, at least a portion of the wire electrodes (e.g., active electrodes) may be exposed enabling them to contact the tissue specimen to be segmented. In some embodiments, the hammock assembly 1044 also comprises perforations or windows 10759 (shown in FIG. 24) for securing the active electrodes/wires 10428. These perforations or windows 10759 may be similar or substantially similar to the perforations 2701 described in relation to FIG. 4 below. For example, the windows 10759 may be designed to control the release of the active electrodes/wires during the pretension step or may be designed to partially release the active electrodes/wires 10428 at select locations and to release the electrodes/wires at the remaining locations during the travel of the wires 10428 during cutting. Control of the release of the electrode(s)/wire(s) during pre-tensioning may be achieved by selection of the perforation per length configuration, combined with the thickness T and elasticity of the film (e.g., thickness and elasticity of the film/perforation layer 10441 in FIG. 21B) containing the perforations/windows 10759, along with the thickness and rigidity of the material in which the perforation layer is attached.

Figure 24:
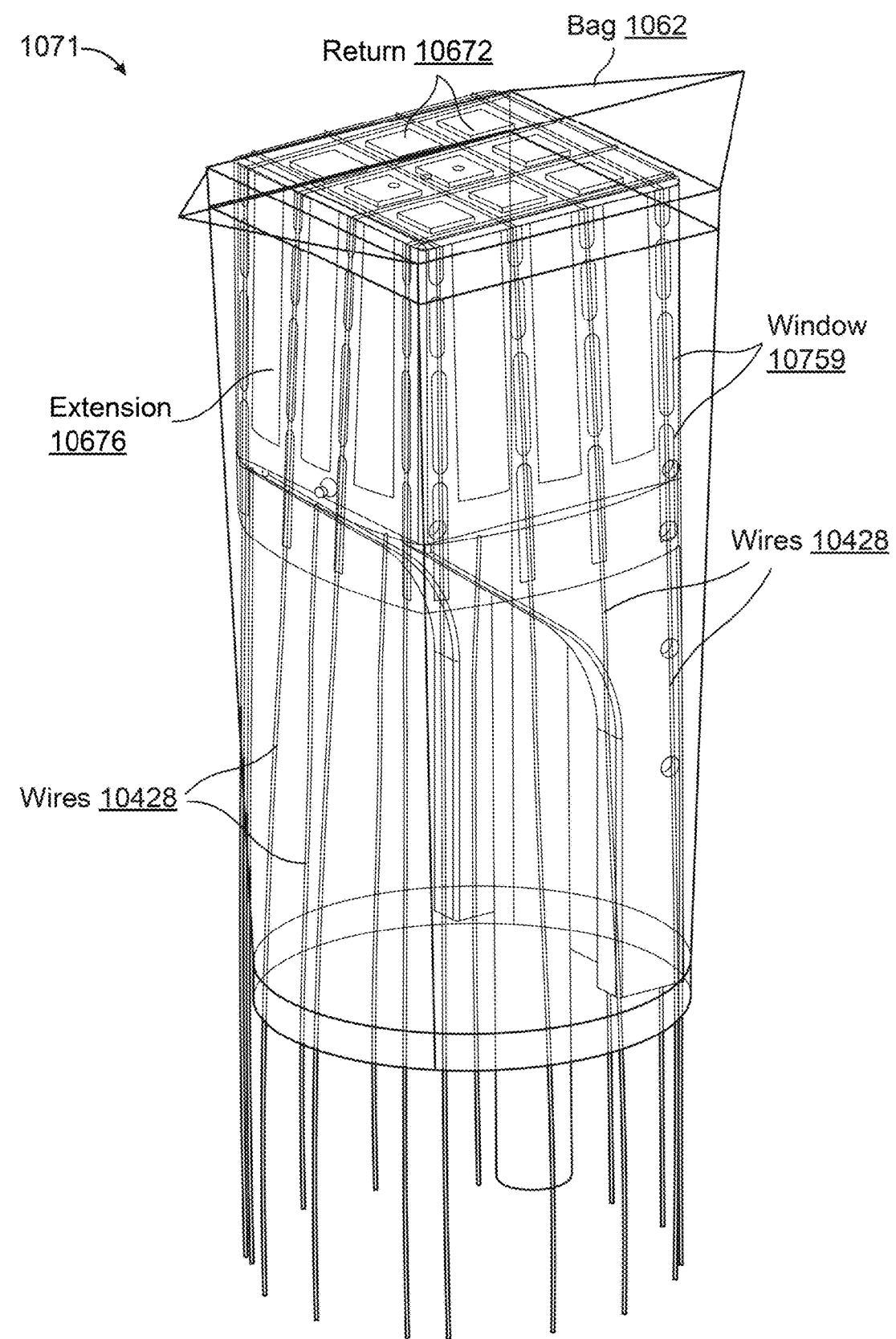
FIG. 24 illustrates a perspective view of a manufactured specimen bag system mounted on the fixture in FIGS. 22 and/or 23, according to various aspects of the present disclosure.

The fixture 1051 also includes one or more receiving holes 10674 and/or protrusions 10673 at or near a bottom end of the square shaped portion 1053 which may be used to help hold the hammock assembly 1044 and its wire electrodes 10428 in place during sealing. Once the hammock assembly 1044 is seated on the top face of the fixture, the specimen bag 1062 is positioned over the fixture as shown in FIG. 24. In some embodiments, the specimen bag 1062 (or inner layer of the specimen bag) comprises a top opening 10656 and a bottom or base 1069, where the top opening 10656 is shaped and sized to receive the fixture 1051 and the hammock assembly 1044 and the base 1069 is shaped and sized to lay flat (or substantially flat) on the top face of the fixture 1051. Once the specimen bag is pulled from the top end to the bottom end of the fixture 1051, heat or thermal energy is applied to seal the hammock assembly 1044 to the interior face of the bag 1062, as shown in FIG. 24. As noted above, the base or bottom 1069 need not be flat, in some embodiments. As used herein, the base 1069 is defined as the side of the bag opposite the direction that the segmenting wires pull through the bag, or as shown in FIG. 24, the side of the bag opposite the bag opening.

FIG. 24 illustrates an example of a specimen bag assembly 1071 comprising a specimen bag 1062 and a hammock assembly (e.g., hammock assembly 1044 in FIG. 23), in accordance with one or more implementations. In this case, the hammock assembly 1044 comprising the plurality of wire electrodes 10428 is sealed/welded to the interior face of the bag 1062, as described above in relation to FIG. 23. The specimen bag 1062 may comprise a plurality of layers, where the plurality of layers are separated by a space (e.g., an air or fluid gap), or alternatively, adhered together. FIG. 13 illustrates an example of a specimen bag comprising a plurality of layers separated by an air or fluid gap, in accordance with one or more implementations.

In some cases, the plurality of layers of the specimen bag 1062 may be formed of the same or a different material, have the same or different thicknesses, the same or different refractive indices, etc. In some cases, the specimen bag 1062 is pulled onto the fixture 1051 upon which it takes the shape of a flat-bottomed 3D bag. In some examples, a hammock assembly 1044 is bonded to an interior of the specimen/containment bag 1062. In such cases, after bonding the hammock assembly 1044 to the interior surface of the specimen bag 1062, the hammock assembly 1044 also takes on a 3D bag shape, as shown in FIGS. 23 and 24. In some cases, the hammock assembly 1044 is bonded to the inside of the specimen/containment bag 1062 using thermal sealing, or alternatively, via adhesives. Other bonding techniques known in the art are contemplated in different embodiments, and the examples listed herein are not intended to be limiting. In some examples, once the combined bag assembly is removed from the fixture 1051, the specimen bag assembly (e.g., specimen bag assembly 1071 in FIG. 24) is configured to maintain the shape and structure of a fully constructed 3D specimen bag. In other words, after removal from the fixture 1051, the specimen bag assembly may be designed to not collapse in on itself. In some cases, mechanical alignment tabs, posts (e.g., post 1057), receiving holes 10674, protrusions 10673, or other applicable grasping features may be used to hold the underlying hammock assembly 1044 while the specimen/containment bag 1062 is loaded onto the fixture 1051 and bonded into place.

As described in further detail below, multiple bag layers may be employed for increased protection for liquid containment and, in the case of RF energy being used inside the containment bag, thermal and electrical insulation.

Figures 37A, 37B:
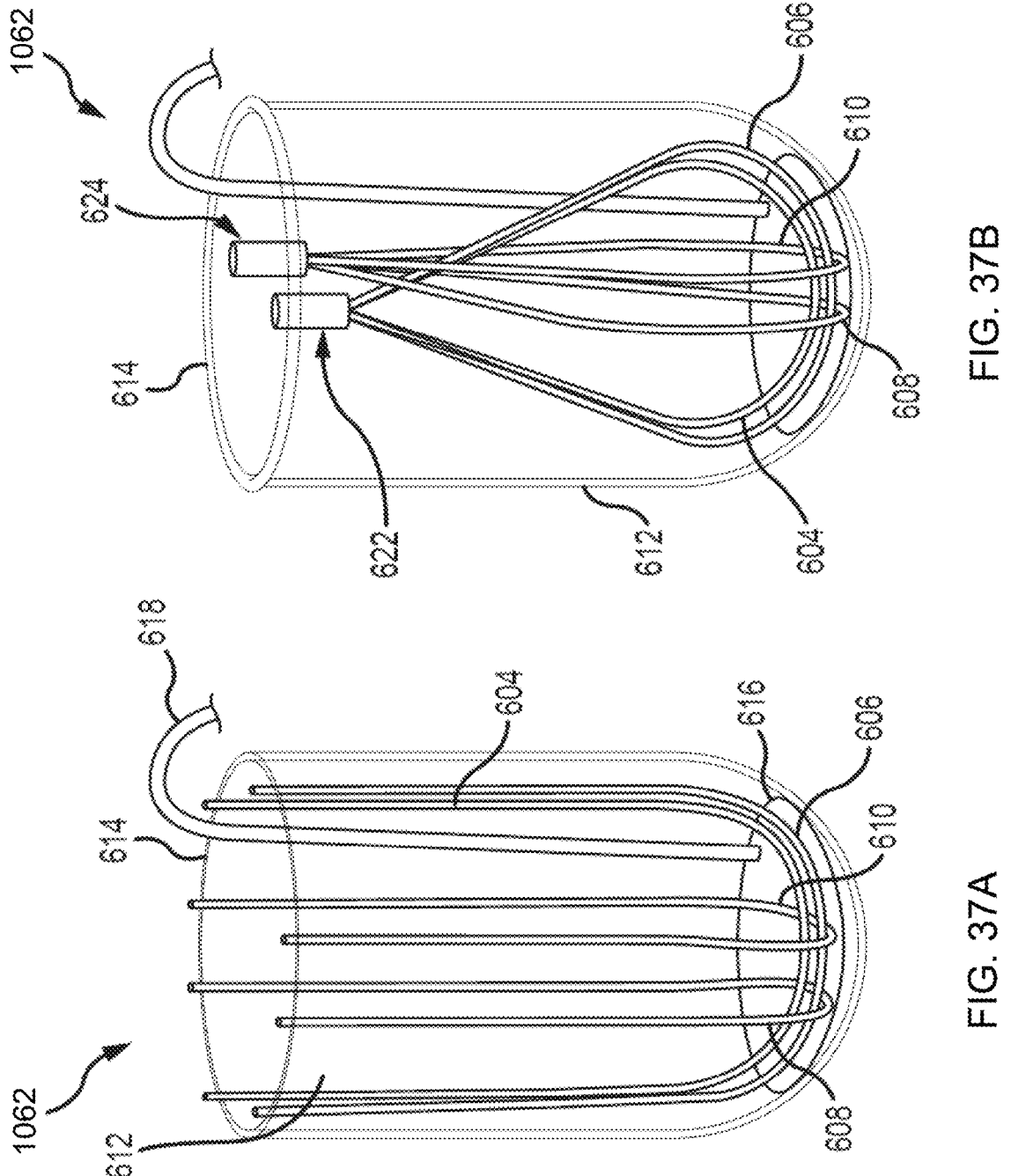
FIGS. 37A and 37B illustrate an example of a specimen bag system comprising a plurality of electrode wires, according to various aspects of the disclosure.
Figure 37C:
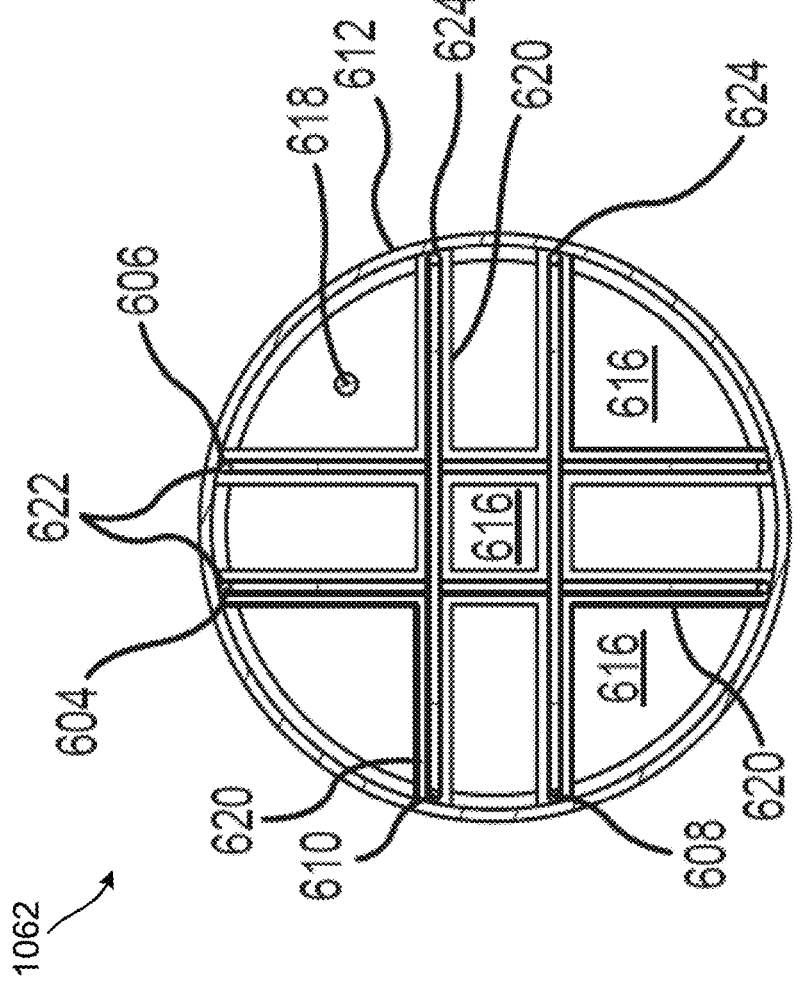
FIG. 37C illustrates a bottom view of the specimen bag system in FIGS. 37A and/or 37B, according to various aspects of the present disclosure.

FIGS. 37A-37C illustrate an example of a specimen bag 1062, in accordance with one or more implementations. In some cases, the specimen or containment bag 1062 may include a container 612 with an entry/opening 614 that is biased to open upon deployment into the patient cavity, for instance, by way of the spring arm assembly described in relation to FIGS. 18 and 19. In other cases, the entry or opening 614 is inflatable to an open configuration to allow a tissue specimen to be placed into the specimen bag 1062. In some cases, the specimen bag 1062 may have an outer or first layer, such as a container 612 made of a plastic, polyvinyl, nylon, polyurethane, or any other bio-compatible insulating material suitable for use in a live patient. Coupled to or as a second layer in the container 612 may be a return electrode 616. In some cases, the return electrode 616 and the one or more active electrodes 604, 606, 608, and/or 610 may be examples of the return and active electrodes of the hammock assembly described above in relation to FIGS. 21A, 21B, and/or 23. In some examples, the electrodes may be crimped together into a first electrode set 622 having first and second electrodes 604, 606 and a second electrode set having third and fourth electrodes 608, 610. In some examples, the first and second electrode sets 622, 624 may be coupled to pull assemblies (not shown). As seen in FIG. 37A, the electrodes 604, 606, 608, 610 may be temporarily attached to the container 612 such that application of a proximal force causes the electrodes to detach from the container 612. Means for attachment may include, but are not limited to, heat staking, stitching, glue adhesive, or other fastening means. In other cases, the electrodes are temporarily attached below a film/perforation layer, as previously described in relation to FIGS. 24 and 25. Further, the electrodes may detach mechanically (e.g., by pulling), electrically (e.g., when a threshold amount of current or RF energy is passed through the electrodes they heat up, thereby degrading the film/perforation layer), or a combination thereof.

The return electrode 616 may be a copper foil or mesh, or any other highly conductive material suitable for use in a live patient, coupled to a return cable 618 for transmitting energy from the patient. The return cable 618, while illustrated as being inside the container 612, may be coupled to the return electrode 616 in any manner suitable for an efficient and safe transfer of energy, such as, being within the layers of the container 612 that are distal of the opening 614, or sitting partially on the outside of the container 612 to keep the return cable 618 out of the way during specimen loading. The return cable 618 may be attached to the return electrode 616 by soldering the return cable 618 to the return electrode 616, mechanical contact applied by layering the return cable 618 and the return electrode 616 together during manufacturing of the specimen bag 1062, adhering the return cable 618 to the return electrode 616 using conducting epoxy or similar materials, and/or by forming the return electrode 616 and return cable 618 from a single continuous foil or mesh.

In some cases, a protective insulating material, such as a barrier 620, may be provided in an interior of the return electrode 616 or as a third layer. The barrier 620 may be positioned between the electrode(s) 604, 606, 608, 610 and the return electrode 616. Those skilled in the art will recognize that, for specimen segmentation to occur, the tissue specimen must be in contact with both the return electrode 616 and the active electrode(s) 604, 606, 608, and/or 610, and that the return electrode 616 cannot contact the active electrode(s) 604, 606, 608, and/or 610 directly. The barrier 620 is therefore an insulating layer between return electrode and the active electrodes and may be made of any material suitable for providing an insulating effect.

Those skilled in the art will also appreciate that the number of layers of the bag construction may be as few as one, two, or three, with components described above being attached to the interior surface of that layer or container 612 and may be greater than three, depending on the embodiment, and that components of the specimen bag 1062 illustrated in the figures (e.g., FIGS. 37A-37C) should be sized and suitably flexible so as to compress within an insertion tool prior to expansion within the patient cavity.

As described below, a multi-layer bag having a vacuum or an air (or another fluid) filled intermediate space may be employed in some embodiments. In some circumstances, one potential risk of temporarily attaching wires to the specimen bag is that the bag may rupture during detachment of the wires. The use of multiple bag layers may help ensure that the bag remains intact upon release of the holding features. While not necessary, in some examples, the holding features are attached to the innermost layer of the bag, with one or more additional layers on the outside of the bag to ensure the bag remains intact and impermeable to fluids.

FIG. 13 is a cross-section view of some components of a bag assembly 1300 with leak detection, according to various aspects of the disclosure. In some cases, a specimen bag (e.g., specimen bag 1062) may comprise a plurality of layers 9102, 9104 separated by a space 9106. Pressure in the space 9106 between the layers 9102, 9104 (with or without channels) may be used to inflate the outer bag layer 9102. If a breach occurs in the outer bag layer 9102, the loss of pressure can be visually detected by looking for a decrease in inflated bag size or pressure. Alternatively, a pressure gauge may be used to detect a pressure drop (e.g., at or above a threshold) within the inflated area(s). In some examples, a vacuum may be applied to the space 9106 between bag layers 9102, 9104. The vacuum may serve two purposes: (1) a vacuum may provide a visual indication of a breach if the outer bag layer 9104 no longer appears to be pulled towards the inner layer 9104; and (2) if a breach occurs in the outer bag layer 9104, the vacuum will draw air into the space between the bag layers 9102, 9104 thereby minimizing the potential for other materials or fluids to escape the hole (in particular if the hole is small). That is, a vacuum in the space 9106 between layers 9102, 9104 may tend to bias an inward flow of fluid, whereas a pressure in the space 9106 would tend to, in the event of a breach, release fluid out and potentially into the patient.

In some circumstances, when a plurality of bag films are constructed together, visualization of the objects and activities contained within the bag can be a challenge. Aspects of this disclosure relate to enhancing the visibility through a containment bag (e.g., specimen bag 1062) having a plurality of layers (i.e., a plurality of bag films). In one non-limiting example, a light source may be inserted inside the containment bag (e.g., specimen/containment bag 1062) to enhance visibility. This can be an independent product that is inserted through the bag opening, or a light source that is part of the actuator that is being used for tissue specimen division. In the latter embodiment, the light source may be a near distal tip light source that is incorporated into the introducer tube, outer tube, or trocar, or alternatively, a light source that originates higher up in the actuator and shines a beam of light centrally through the introducer tube to illuminate the tube and/or acts as a spotlight that shines on the bag contents through the distal end of the introducer tube. In another example, the light source may be positioned on or near the first, second electrode sets 622, 624. In yet other cases, the light source may be configured to extend (proximally) from the flexible member 1041 of the spring arm assembly illustrated in FIG. 19. In either case, the light may be used to help the user or surgeon position the introducer tube (i.e., part of the segmentation instrument) such that it is or near a top of the tissue specimen.

In some other cases, the surface finish on each bag layer or bag film may be designed to minimize any reflectance that may occur and impact visibility for a camera using a light source that is placed outside the specimen/containment bag. In yet other cases, some or all of the plurality of layers may be adhered together in order to reduce any refracting that may occur due to layers that are separated in space. For instances, layers, or portions of layers of the specimen bag

1062, may be laminated together to remove the space between the containment bag layers. Additionally, or alternatively, a transparent adhesive may be used to physically adhere portions of the bag layers together to give a visualization 'window' where a user can easily peer into the containment bag 1062. It should be noted that the examples listed above are not intended to be limiting, and other techniques for making the bag layers or bag films appear "more transparent" are contemplated in different embodiments. For instance, in some cases, the different bag layers may be composed of different materials. In one non-limiting example, the innermost bag layer may be composed of a first material having higher strength and lower transparency, while the subsequent bag layers may be composed of a second material having lower strength and substantially higher transparency. In another non-limiting example, the innermost bag layers may be made of a first material having lower strength and higher transparency, while the outermost bag layer may be composed of a second material having higher strength and lower transparency. In some other cases, the bag layers may be formed using materials having different refractive indices. Further, the bag layers may be arranged and positioned based on their respective refractive indices, for instance, in an ascending order or a descending order of their refractive index.

As described below in relation to FIGS. 5 and/or 17, aprons (e.g., apron 2885) may be employed within the specimen bag (e.g., specimen bag 1062) to keep the wires out of the way during tissue loading and/or isolate a second set of wires (e.g., return electrodes 10444 in FIG. 21B; second set of wires 608, 610 in FIG. 37B) from a first set of wires (e.g., active electrodes 10442 in FIG. 21B; first set of wires 604, 606 in FIG. 37B). In some cases, the aprons may also be used to isolate active electrode wires from each other, such as, but not limited to, active electrode wires 604, 606, 608, and 610 in FIG. 37B. In some cases, a second apron may run along the full inner perimeter of the bag or partially around the bag. The advantage to a larger second apron is to ensure that the first set of wires remain separate from the second set of wires.

In some examples, a connector (e.g., connector carrier 10105 in FIG. 1) is used to hold the connector pins that connect the cutting wires (i.e., segmenting wires) to the receptacles in the segmenting equipment. In order to aid in building the bags, the connector may have openings or slots along the holes that hold the connector pins. This allows the connector pins to be placed in the connector after the active electrode and/or return electrode wires have already been attached to the connector pins. Without the side entry connector, the wire assembly requires the wires to be fed through the connector and then attached to the pin. Minimal space may make this step problematic.

Inflation Channels

In some embodiments, inflation channels may be utilized between the outer and inner layers, or alternatively, on the outer layer only, of the containment bag for added protection to the patient, thermal or electrical insulation, and/or aiding in bag opening, to name a few non-limiting examples. Broadly, inflation channels may serve some or all of the following purposes: (1) thermal protection, (2) bag expansion to hold the bag open under insufflation or to aid in bag opening, (3) creating rigid bag areas, (4) leak detection, (5) holding the specimen, (6) holding pneumoperitoneum around the incision, and (7) ensuring the return is in contact with the specimen. In order to fulfill one or more of these purposes, the inflation channels may be separately created out of two films and then attached to one or more bag layers;

or alternatively, one or more of the bag layers may be utilized to construct the inflation channels. In some cases, the inflation channels 11121 may be created through a process such as welding, laser cutting or welding, or another applicable process. If not welded to a bag layer, the inflation channels may be attached using pressure sensitive adhesive, another adhesive or glue, or similar means. In some embodiments, the inflation channels may be in fluid communication with each other. Alternatively, one or more of the inflation channels may not be in fluid communication with the other inflation channels.

In some cases, a multi-layer bag with an inflatable and/or sealable volume between the inner and outer layers may be utilized to create the inflation channels (also referred to as inflatable channels, such as inflatable channels 11121 in FIG. 28). This volume may be directly accessed by a fitting (e.g., a port or channel opening, such as channel opening 11122 in FIG. 28) that would either be attached to the body of the bag 1062 or to an extension of the bag 1062, where the extension of the bag 1062 is configured to extend outside of the patient during use. In some embodiments, this fitting, such as a port, may be configured to receive a syringe (e.g., shown as fluid source 11124 in FIG. 28) for inflation of the channels 11121. In other cases, the port may be coupled to an external air or inflation source or gas cylinder to inflate the bag 1062. In some embodiments, the fitting may also be used in conjunction with a valve. The pressure could be adjusted with the built-in valve or with a separate valve/manifold that is located outside of the patient. Inflation of the bag can also serve as (1) an additional protection in case of elevated tissue temperatures caused as a result of the RF cutting effect and/or (2) as an electrical insulation/isolation layer. In some circumstances, tissue in the vicinity (e.g., tissue or tissue structures contacting the outside of the bag) of a tissue specimen being segmented may become hot during the segmentation procedure. To mitigate such risk, an insulating layer of air may be captured by way of the inflatable channels 11121 on the exterior of the specimen bag 1062. This helps prevent adjacent tissue or surrounding structures from overheating due to the thermal energy generated by the RF cutting. The inflatable channels 11121 described below in relation to at least FIG. 28 may implement one or more aspects of the inflated (or inflatable) cells 3132 shown in FIG. 7.

Furthermore, as described in relation to FIG. 13 below, a multi-cell layer between the outer bag layer and the inner bag layer may include a number of interior spaces that serve to reduce the volume of fluid that may potentially leak in the event the inner layer is compromised. For example, a number of walls coupling the inner layer and the outer layer may form a number of smaller fixed volumes of air, fluid, gel, or other leak mitigation or leak management means described herein within the space between the inner and outer layers of the bag. The layers 9102, 9104 may be coupled to or fused to one another using any means known in the art, such as at a joint 9108.

Figure 29:
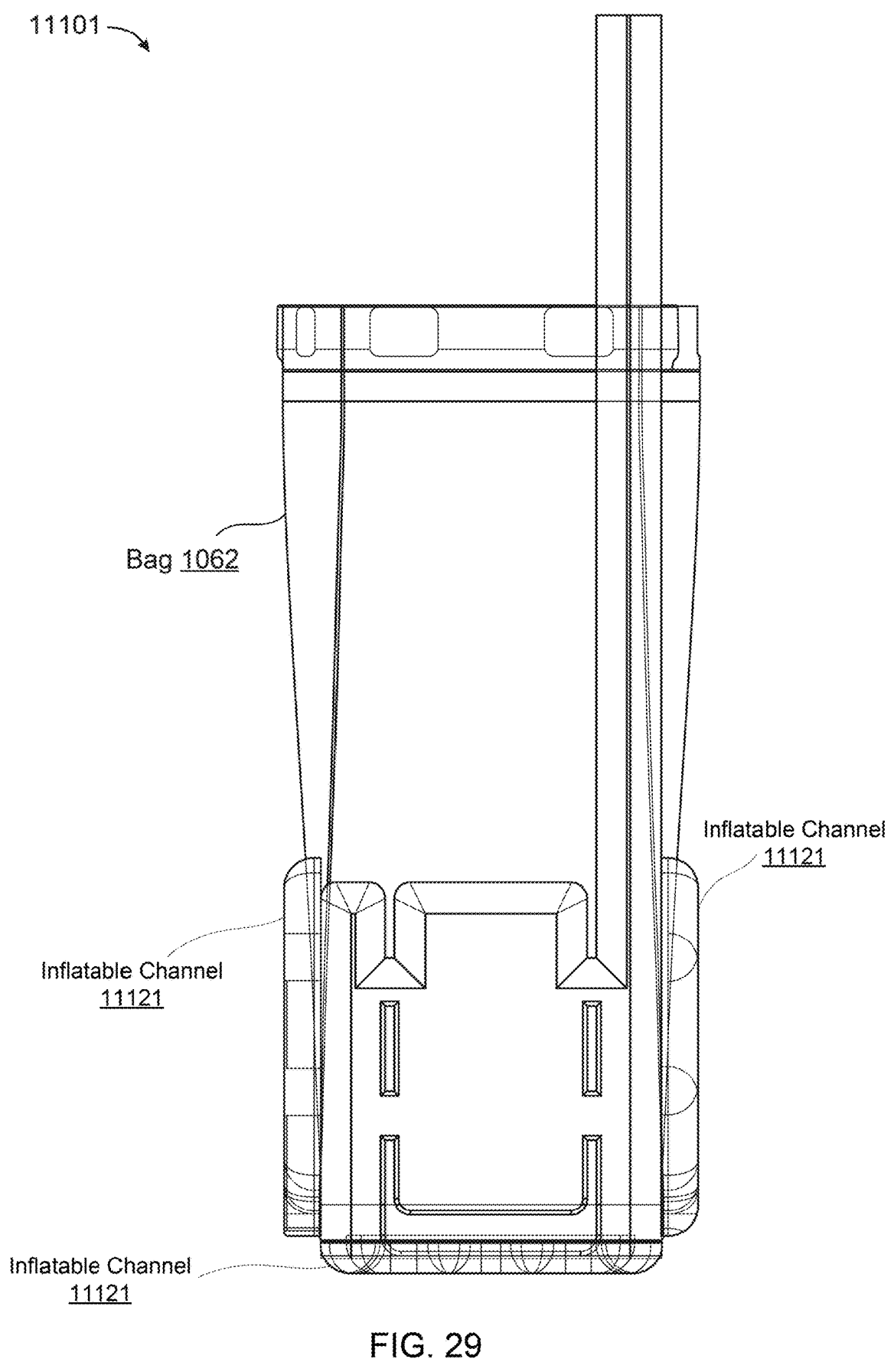
Figure 30:
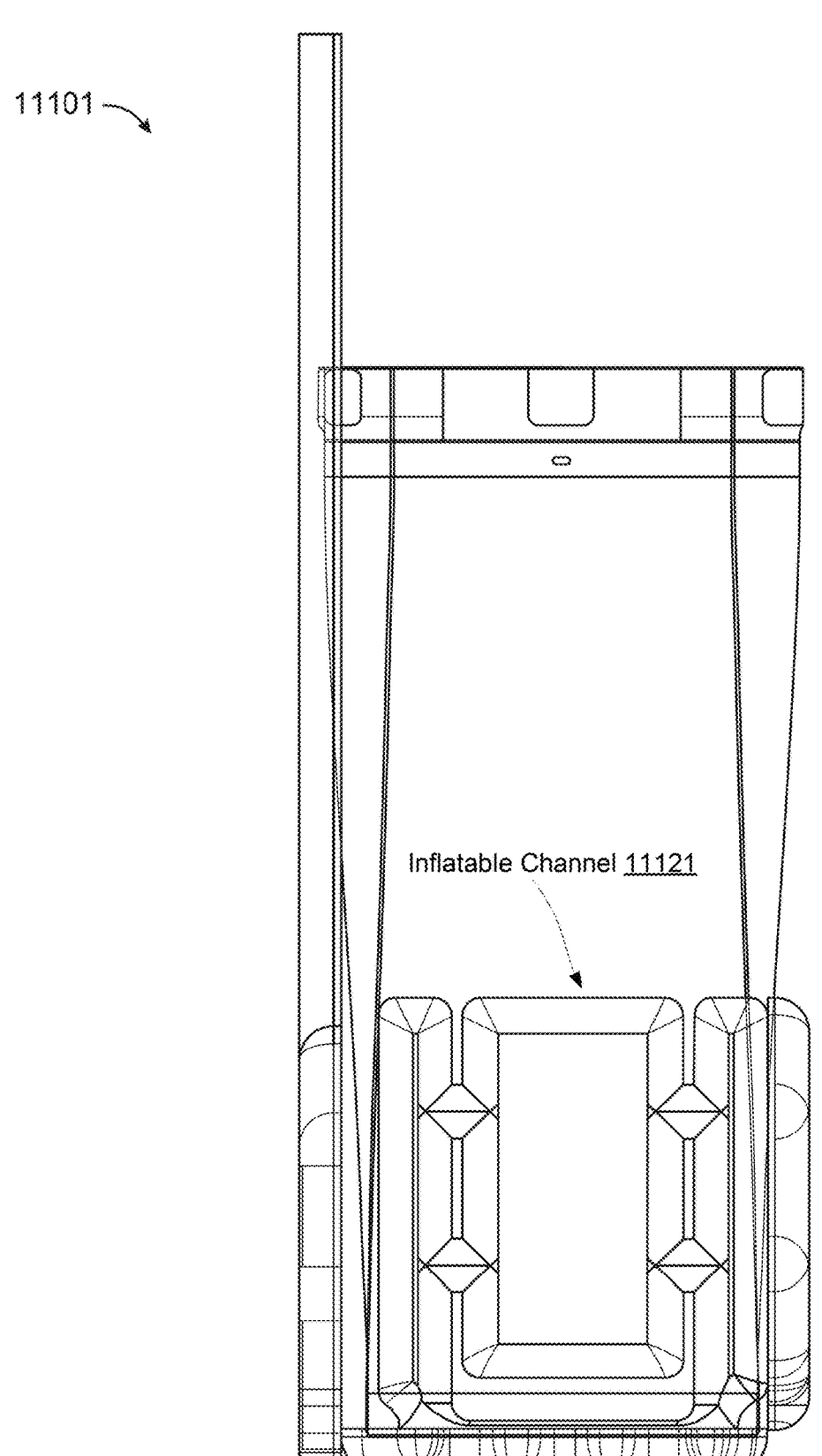
FIG. 30 illustrates a side view of the specimen bag system in FIG. 28, according to various aspects of the present disclosure.
Figure 31:
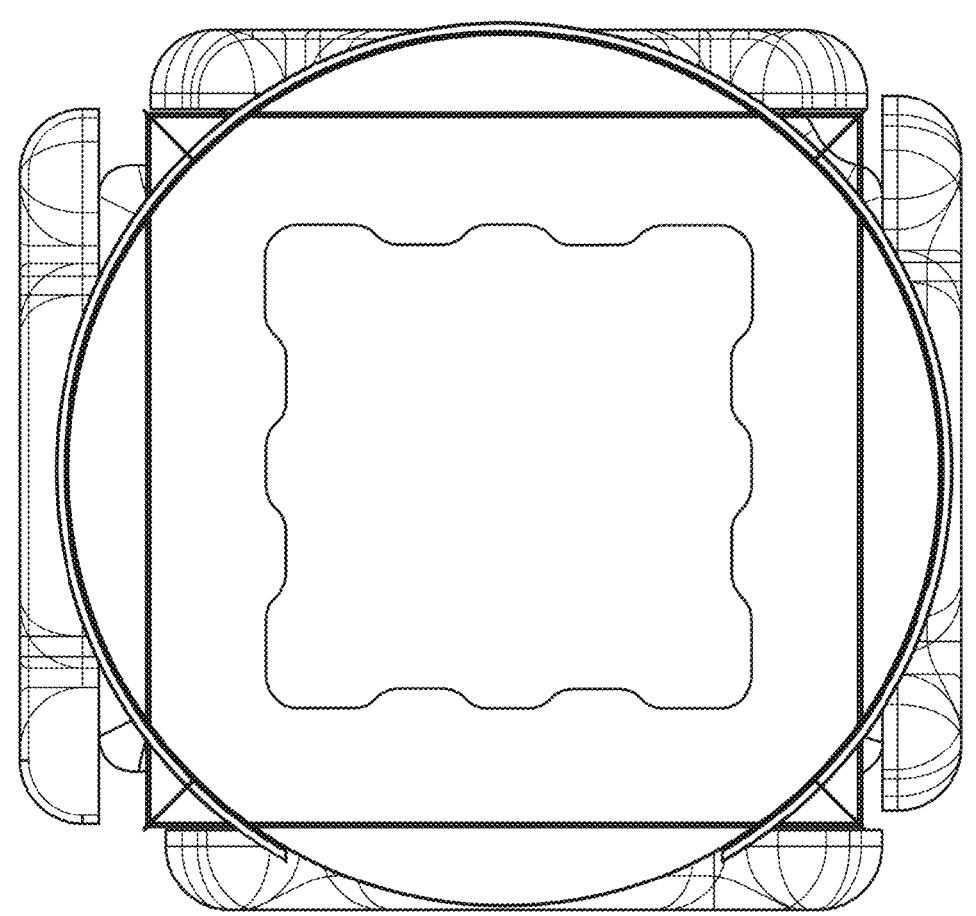
FIG. 31 illustrates a top view of the specimen bag system in FIG. 28, according to various aspects of the present disclosure.
Figure 32:
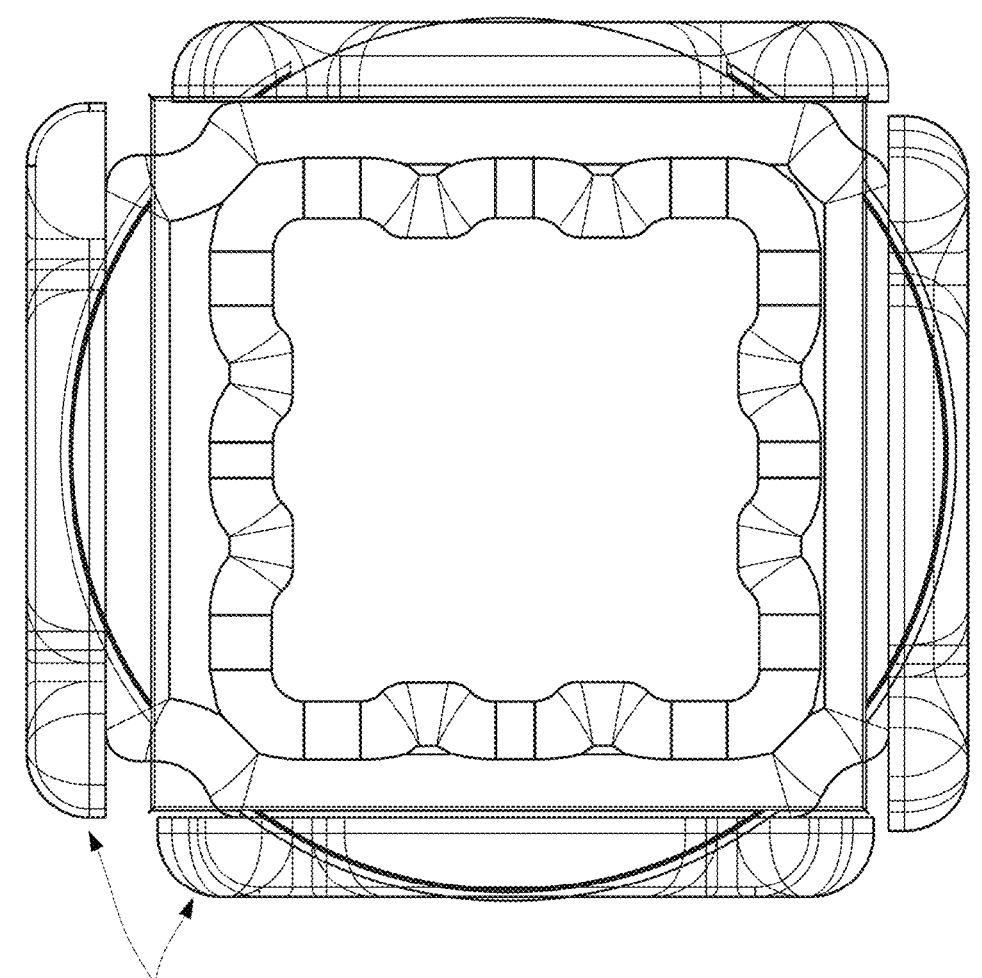
FIG. 32 illustrates a bottom view of the specimen bag system in FIG. 28, according to various aspects of the present disclosure.
Figure 33:
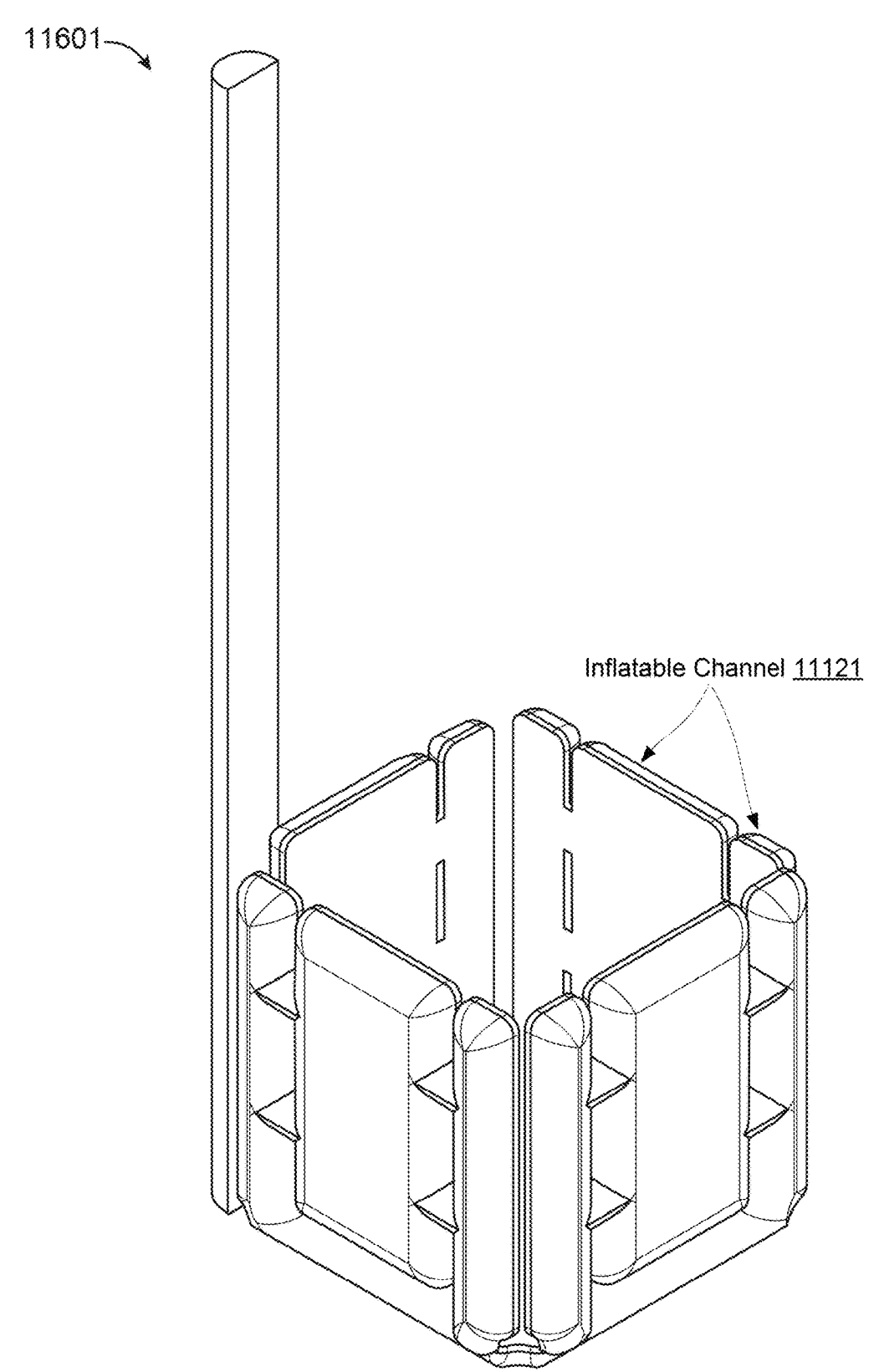
FIG. 33 illustrates a perspective view of the inflatable channels of the specimen bag system in FIG. 28, according to various aspects of the present disclosure.
Figure 34:
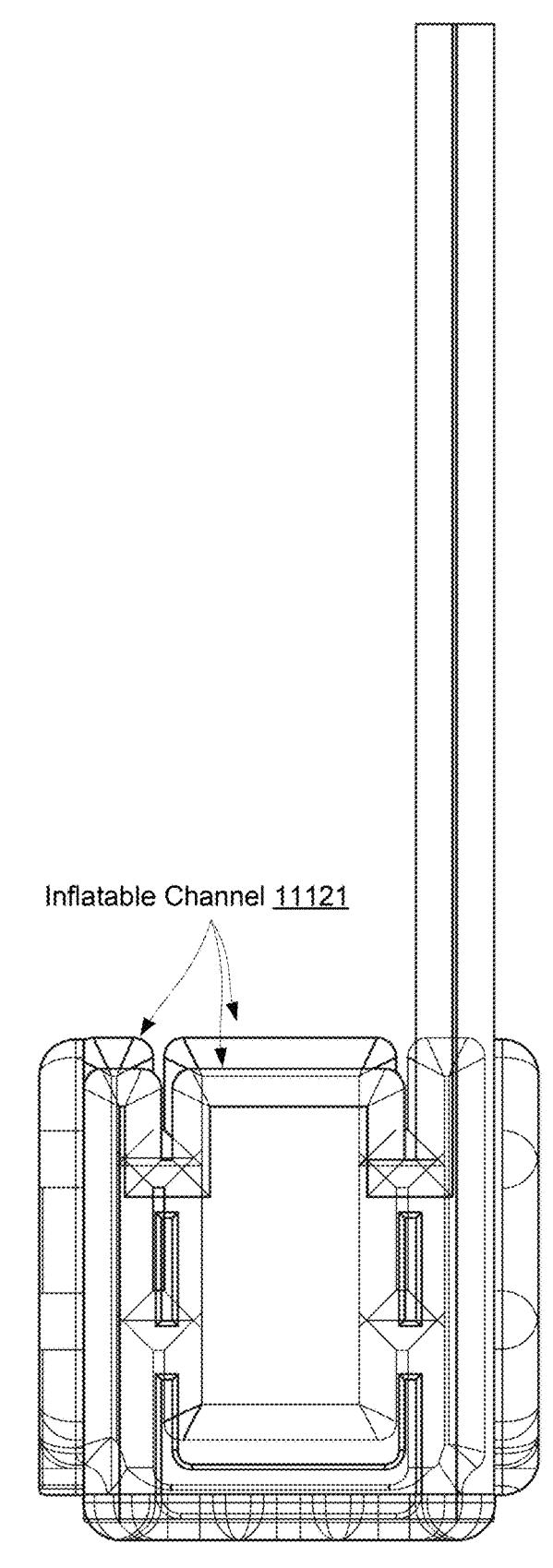
FIG. 34 illustrates a front view of the inflatable channels in FIG. 33, according to various aspects of the present disclosure.
Figure 35:
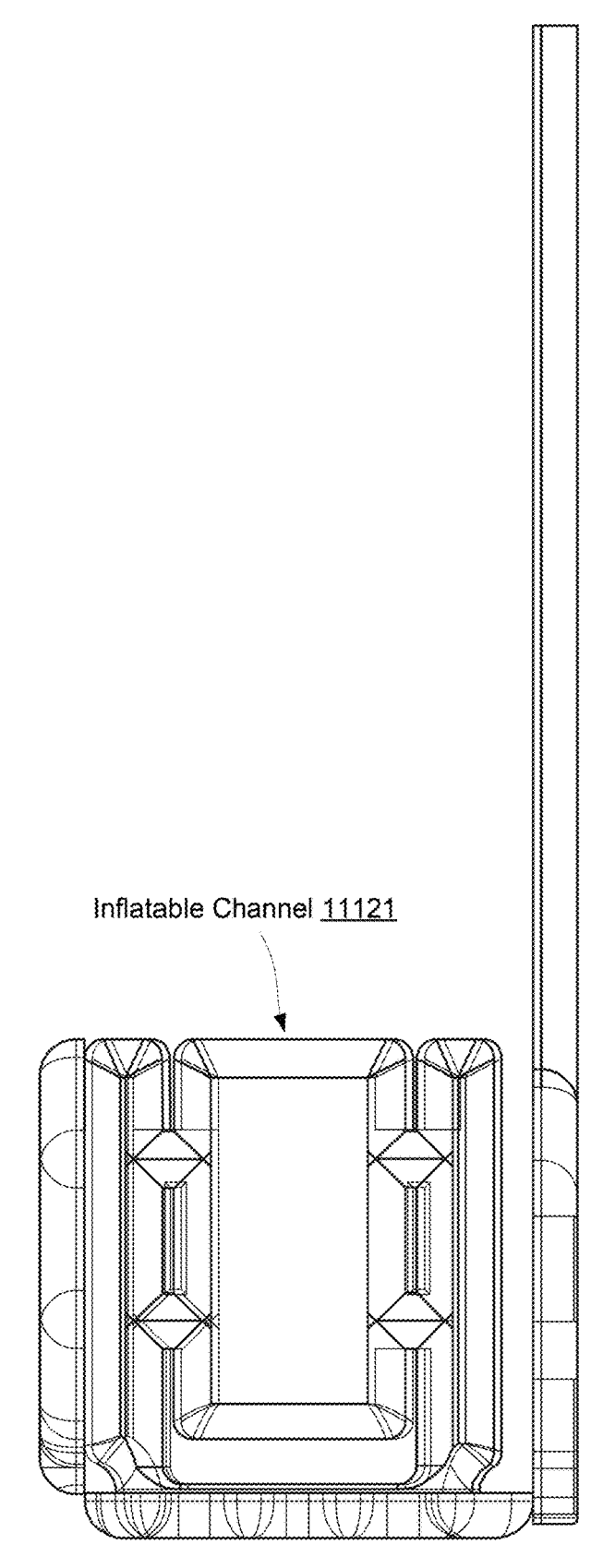
FIG. 35 illustrates a side view of the inflatable channels in FIG. 33, according to various aspects of the present disclosure.
Figure 36:
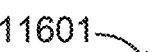
FIG. 36 illustrates a bottom view of the inflatable channels in FIG. 33, according to various aspects of the present disclosure.
Figure 36:
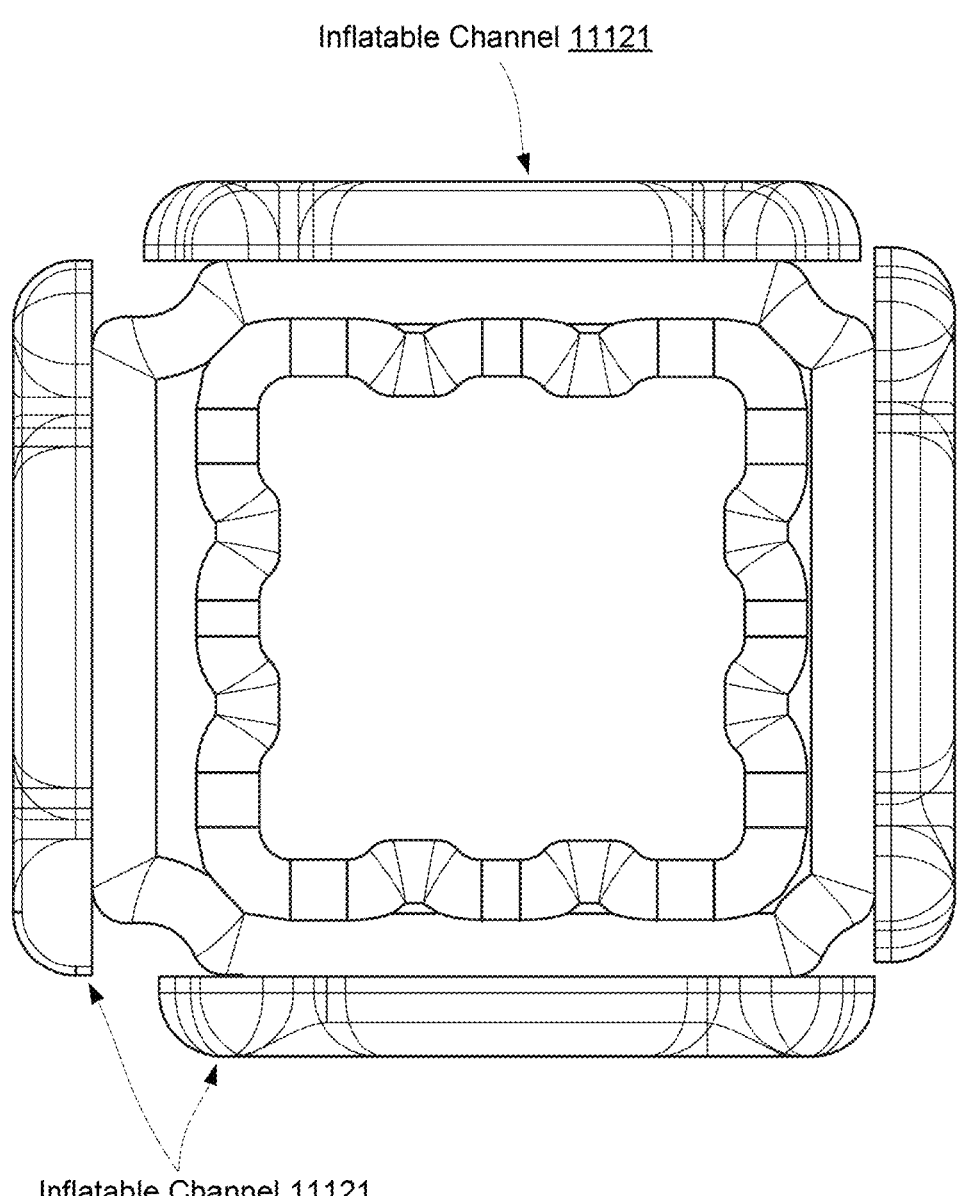

In some cases, the effect of the inflation channels 11121 on the interior space within the bag 1062 may be minimized or reduced to lessen the likelihood of the inflation channels 11121 impinging on the segmenting means (e.g., cutting wires) and/or taking up working space within the interior of the bag. To do this, the inflation channels may be positioned along, or designed to coincide with, the side walls and/or base of the specimen bag, as shown in FIGS. 28-30. Alternatively, the inflation channels 11121 may be positioned at or near the bag return (shown as return electrode 616 in FIG. 37C). In some other cases, inflation channels may be formed using two films of different thicknesses or durometers. In such cases, the thinner or lower durometer film may expand preferentially (i.e., more easily) as compared to the thicker film. For example, one film may be made from the inner bag layer with a thicker film and a thinner or lower durometer layer attached to or welded to the inner bag layer. Upon inflation, the thinner outer film of the inflation channel may expand outward while minimizing the amount that the thicker inner film expands inward.

Figure 25:
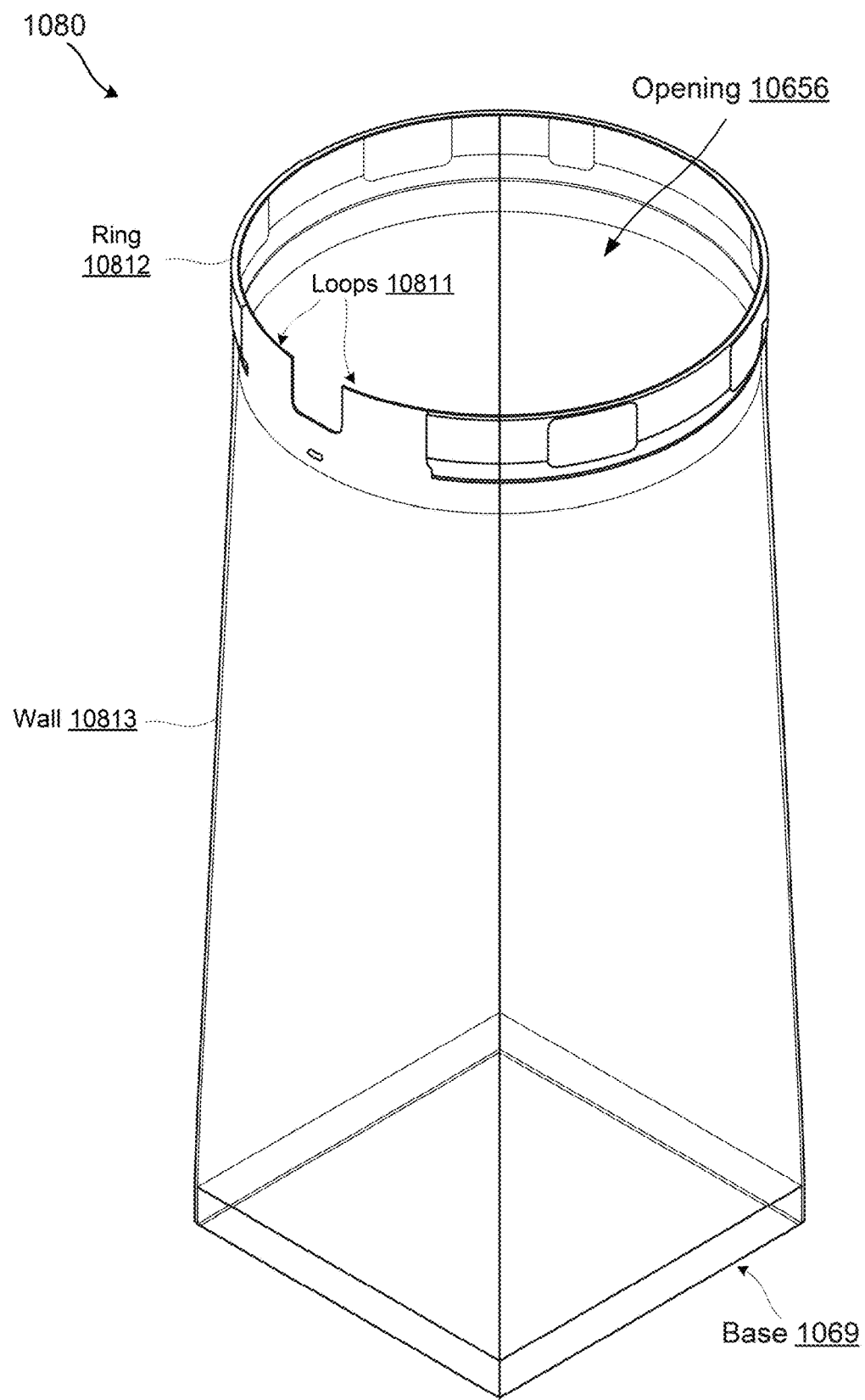
FIG. 25 illustrates a perspective view of a specimen bag comprising a plurality of film layers, according to various aspects of the present disclosure.

In some embodiments, one or more structural additions may be added to portions of the bag, such as, but not limited to, the bag edges (e.g., base 1069, sidewalls 10813 in FIG. 25). In some embodiments, a mattress-like or tufted design may be utilized for the inflatable channels 11121, as shown and described in relation to FIGS. 41A-B. The tufted design (e.g., resembling a pillow or mattress, shown as tufts 11331 in FIGS. 41A and 41B) may be configured to expand and distribute the pressure from the inflation channels 11121 across a larger surface area. In some cases, one or more inflation tubes may be attached to the opening(s) of the inflation channels 11121 for inflating the channels. The user (e.g., surgeon) may inflate the channels through the tube/channel entrance, such as channel opening 11122, using a syringe, pump, or another applicable air/fluid source 11124. In some cases, a narrow channel opening (e.g., <1 cm or 0.39 inches) may be utilized, which may help pressurize the channel opening(s) 11122 and fill or substantially fill the channel layer(s) of the specimen bag. Additionally, or alternatively, the width of the channel may be tapered (e.g., narrower near the mouth of the channel and wider towards the opposing end of the channel). In some embodiments, an inflation tube may be attached to the channel films using an adhesive, solvent, weld, clamp, etc. In one non-limiting example, the inflation tube may comprise a "luer" taper on its opposing end (i.e., the end not in connection with the channel) for connecting to a gas, air, or another applicable fluid source.

To keep the inflation tube out of the way during bag rolling and/or placement in the deployment instrument (DI), the inflation tube may be placed on the distal end of the bag (e.g., at or near the spring arms, or near a proximal end of the spring arms). If placed at the proximal end of the spring arms, the inflation tubing may be positioned within the space between the spring arms, or alternatively, may be run parallel to, or attached to, the return electrode. In some examples, the return cable (or return electrode) and inflation tubing may run under the carrier (e.g., connector carrier 10105) and into the inner tube (e.g., inner tube handle).

Turning now to FIGS. 28-32, which illustrate different views of a specimen bag assembly 11101 comprising a specimen bag 1062 and a plurality of inflatable channels 11121 positioned along a base and one or more sidewalls of the specimen bag, according to various aspects of the disclosure. As seen, the specimen bag 1062 comprises a top opening 10656 (e.g., formed by a plurality of spring arms or a ring 10812), one or more sidewalls 10813, and a base (e.g., shown as base 1069 in FIG. 25). In this example, the specimen bag 1062 is tapered from the circular top opening 10656 to the square/rectangular base, however this is no way intended to be limiting. In some cases, the specimen bag 1062 comprises multiple layers (e.g., a first interior layer, a second layer, a third layer, etc.). An optional gap (e.g., air gap) may be provided between the adjacent layers of the specimen bag 1062. In one non-limiting example, the specimen bag 1062 comprises three layers, an inner layer, an outer layer, and a middle layer. Further, an air gap (or another fluid gap) may be provided between each layer.

Alternatively, the inner and middle layers may be adhered together, and an air gap may be provided between the outer layer and the middle layer.

FIGS. 28-32 also depict the inflatable channels 11121 formed along at a portion of the specimen bag 1062. In some cases, one or more inflatable channels 11121 are formed along each sidewall 10813 of the specimen bag 1062. In this example, the inflatable channels 11121 extend upward from the base of the specimen bag to slightly under half the height of the sidewalls 10813. In other cases, the inflatable channels 11121 may extend along the entire (or a majority) of the height of the sidewalls 10813. It should be noted that, the examples described herein are not intended to be limiting and different inflatable channel structures are contemplated in different embodiments. The specimen bag 1062 also includes one or more inflatable channels on its underside (i.e., adjacent the base), more clearly seen in FIGS. 29-30.

As an alternative to channels in the bag, one or more rigid members may be attached to the bag, where the one or more rigid members may assist in opening the bag once the bag is deployed from the DI. In some examples, the one or more rigid members may be formed from nitinol wires, elastic spring members, and/or expandable multi-layer plastic ridges, to name a few non-limiting examples. In some cases, the multi-layer ridges formed from plastic (or another applicable material) may be configured to expand as a result of fluid contact through fluid absorption, or alternatively, without fluid contact due to memory, to name two non-limiting examples.

Bag Inflation

Inflation within the inner bag and/or between one or more of the bag layers may be used in addition to, or in lieu of, the channels 11121 on the exterior surface of the bag 1062. In some cases, inflation may be done prior to (or during) segmentation and/or may be sustained during segmentation. In some cases, a seal may be created between the segmentation instrument (also referred to as segmenting equipment) and the bag, which helps maintain inflation inside the inner bag during segmentation. In some examples, a user or surgeon may hold the bag and segmentation instrument together. Alternatively, a clamp or tie, or another mechanical means, may be used to seal the bag to the segmenting equipment. In some cases, the sealing may also help minimize loss of air pressure. In addition to a high flow and/or pressurized air source, the segmentation instrument may also be sealed in order to minimize air pressure loss, in some embodiments. The segmentation instrument may be sealed using a variety of approaches. For example, in some embodiments, one or more gaskets, ultrasonic welds, adhesives, and/or O-rings may be used to seal the instrument shells or spring trays. In other cases, the surgeon may utilize the tissue to block or effectively seal the distal end of the introducer tube by creating a larger and/or flatter contact area. In yet other cases, a ball (e.g., Teflon or silicone ball) may be positioned in the introducer tube to minimize loss of air. As can be appreciated, the use of a ball may assist in reducing or minimize air loss but may still allow the segmenting wires to wrap around/past the ball in the introducer tube so that they can enter the interior of the specimen bag. In some embodiments, a hydrogel may be utilized in the tension tray where the wires pull through the segmenting instrument to further minimize air loss through the tray.

In some embodiments, a separate shell or bag may be placed around the segmenting equipment. This separate shell or bag may be checked for leaks prior to placement around the segmenting equipment. The clamshell may serve as an accessory to the segmenting equipment and may be shaped and sized to fit over the segmenting equipment after the introducer tube is extended into the patient to seal the gaps (if any). In some cases, this clamshell may comprise one or more O-rings for sealing off the cable and/or for providing a seal between the introducer tube and shell.

To provide air pressure to the bag (or to pressurize the air in the bag), an air source may be attached to the segmenting equipment, in some examples. In some other cases, the air source may be directly coupled to the bag or placed directly into the bag. It should be noted that, different techniques for pressurizing the air in the specimen bag are contemplated in different embodiments and the examples listed herein are not intended to be limiting.

Figure 26:
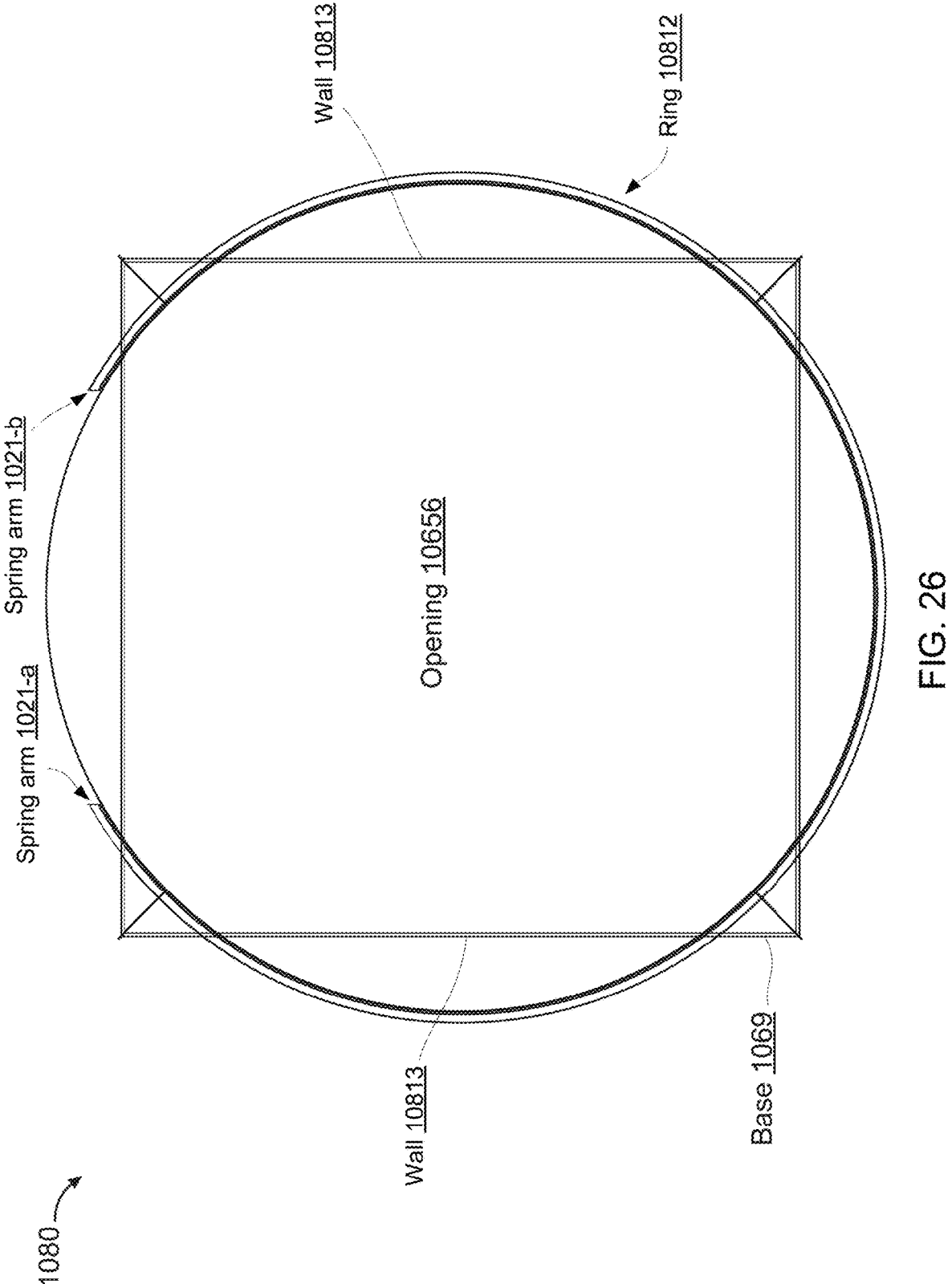
FIG. 26 illustrates a top view of the specimen bag in FIG. 25, according to various aspects of the present disclosure.
Figure 27:
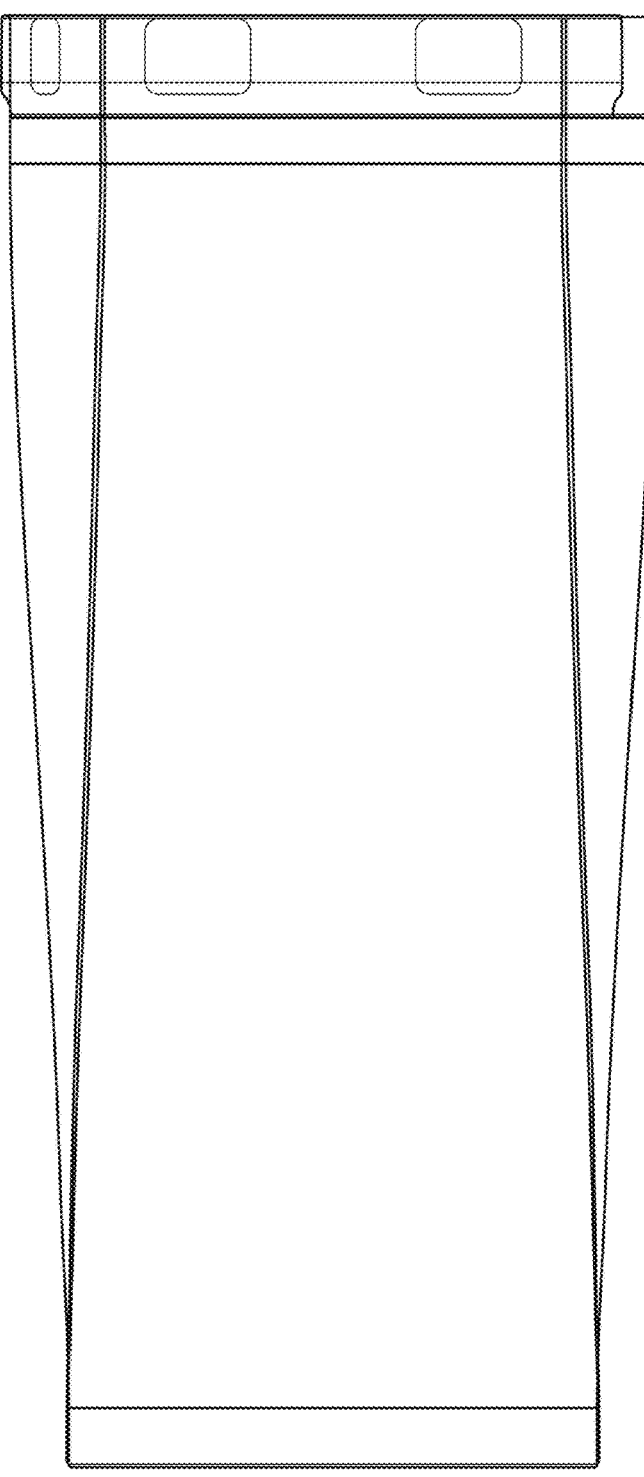
FIG. 27 illustrates a side view of the specimen bag in FIG. 25, according to various aspects of the present disclosure.

FIGS. 25-27 illustrate various view of a specimen bag 1080 according to various aspects of the disclosure. The specimen bag 1080 may implement one or more aspects of the specimen bag(s) disclosed herein, including at least specimen bag 1062 described in relation to FIGS. 23 and 24. The specimen bag 1080 includes an opening 10656 at its top end, where the opening 10656 may be formed by a ring (shown in FIG. 1) or expansion of a plurality of spring arms (e.g., spring arms 1021-a, 1021-b in FIG. 19). In some cases, the plurality of spring arms 1021-a, 1021-b form a ring 10812 around the top opening of the specimen bag. The specimen bag 1080 further includes a plurality of exterior sidewalls 10813 and a base 1069. In some cases, the specimen bag 1080 comprises a plurality of bag layers or film layers, where the plurality of layers are separated by one or more air/fluid gaps, for instance, to enhance thermal insulation. In other cases, the plurality of bag layers are laminated or adhered together, for instance, to enhance thermal insulation, enhance structural integrity of the specimen bag, or a combination thereof. In the example shown, the specimen bag 1080 comprises one or more flexible loops 10811 for attaching the ring 10812 to the specimen bag. In some cases, the specimen bag 1080 may be similar or substantially similar to the specimen bag 10101 described in relation to FIG. 1. The flexible loops 10811 can be bunched up together (i.e., when initially rolled up in the outer tube or cannula assembly, or when the flexible ring 10812 is drawn back into the outer tube), or they can be spread apart when the flexible ring 10812 is advanced, holding the top of the bag open.

FIGS. 33-36 illustrate various views of an inflatable channel system 11601 configured for use with any of the specimen bags disclosed herein, including at least specimen bags 1080, 1062, and/or 10101. The inflatable channel system 11601 comprises a plurality of inflatable channels 11121, where the inflatable channels 11121 are similar or substantially similar to the ones described in relation to at least FIGS. 28, 38A-38I, and/or 41A-41B.

FIGS. 38A-38I illustrate various configurations of hammocks, specimen bags, channels, and/or channel layers, according to various aspects of the disclosure. In some embodiments, inflation channels may be attached to a hammock assembly, and the hammock assembly may be attached to a bag layer (e.g., an exterior surface of an inner bag layer, an interior surface of an outer bag layer, to name two non-limiting examples), further described below in relation to FIGS. 38A and/or 38B. In some other cases, a hammock assembly comprising one or more channels may be provided and affixed to an exterior surface of an inner bag layer or an interior surface of an outer bag layer, further described in relation to FIG. 38E. In yet other cases, a hammock assembly comprising one or more channels may be provided, where at least one of the one or more channels may be positioned on an exterior surface of the outer bag layer, further described in relation to FIG. 38F. In some embodiments, a specimen bag having an inner bag layer, at least one inflation channel layer, and one or more outer bag layers may be provided, where the at least one inflation channel layer may be positioned on the exterior surface of the inner bag layer, further described below in relation to FIGS. 38G and 38H. In some embodiments, a specimen bag comprising a bag layer with attached inflation channels on the exterior of the bag layer may be provided, further described in relation to FIG. 38I. In such cases, the specimen bag may or may not comprise one or more additional outer bag layers.

Figure 38B:
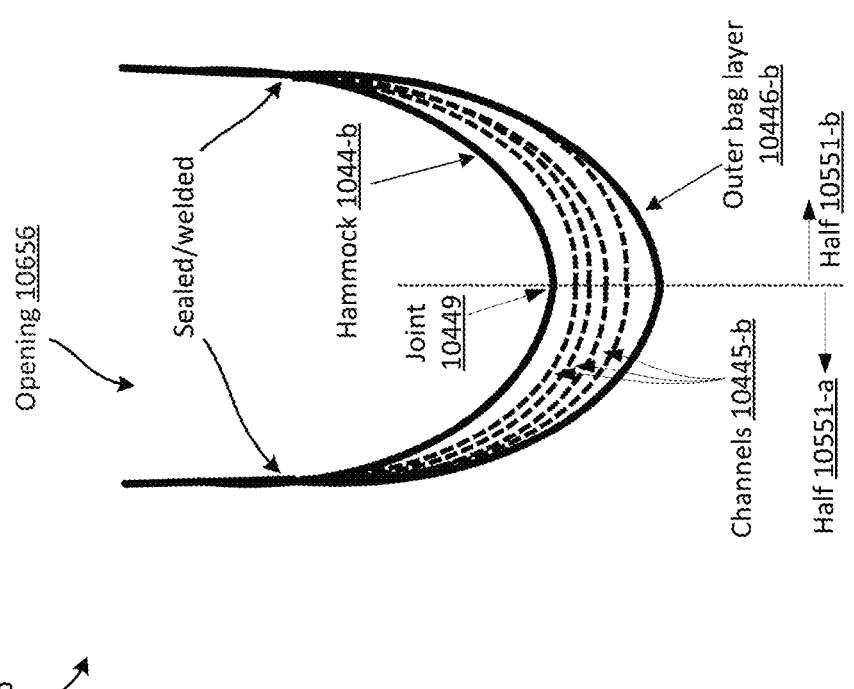
FIG. 38B illustrates an example of a hammock assembly having a clamshell design, according to various aspects of the disclosure.
Figure 38A:
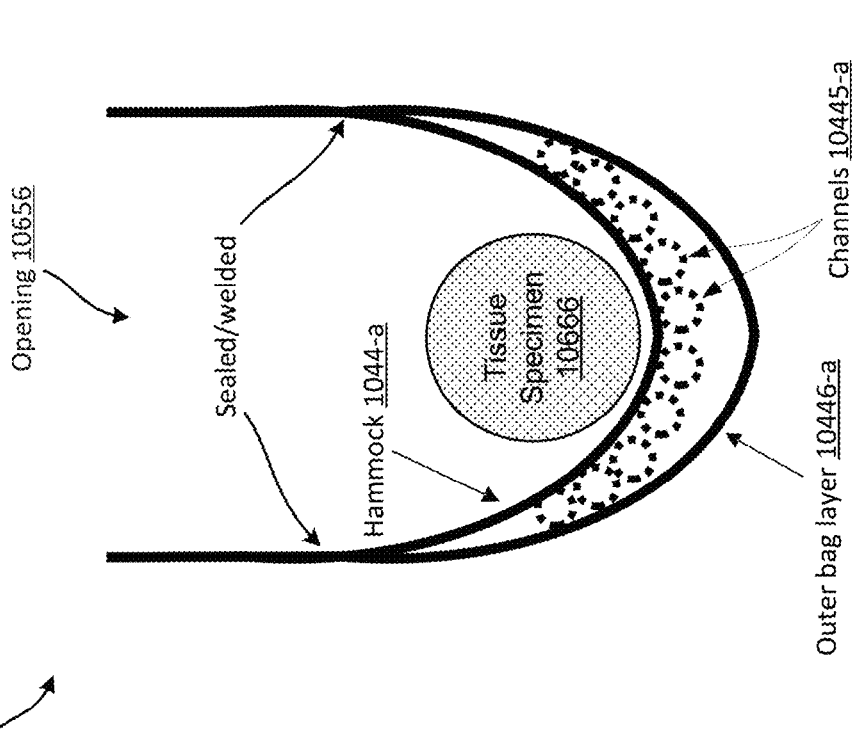
FIG. 38A illustrates an example of a hammock assembly comprising a plurality of channels for containing wire electrodes, according to various aspects of the disclosure.

FIG. 38A illustrates an example of a specimen bag 1062-a comprising an inner bag layer or hammock 1044-a on which the tissue specimen 10666 rests, an outer bag layer 10446-a, and a plurality of channels 10444-a, according to various aspects of the disclosure. Here, each channel of the plurality of channels 10444-a is shaped and sized to receive one or more segmenting electrodes or wires (not shown). As seen, the plurality of channels 10444-a are formed in a space/volume between the hammock 1044-a and the outer bag layer 10446-a. In some cases, the channels 10444-a may be examples of inflation channels and may be attached to the hammock 1044-a. Further, the hammock 1044-a may be attached to the outer bag layer 10446-a as shown in FIG. 38A. In some cases, the outer bag layer 10446-a comprises a base or bottom (i.e., a side opposite the opening 10656 of the bag 1062) and one or more sides (or sidewalls). In some cases, an inflation channel layer comprising the plurality of inflation channels 10444-a may be positioned on an opposite side of the hammock 1044-a from where the tissue specimen 10666 sits. As previously noted, the inflation channels 10444-a may serve multiple functions, including, but not limited to, serving as a thermal barrier, aiding in loading/placing the tissue specimen 10666 in the bag 1062-a, and/or ensuring that the hammock 1044-a is fully opened, and the segmenting wires are free to move prior to or during segmentation. Depending on their purpose, the inflation channels 10444-a may be inflated prior to or after the tissue specimen 10666 has been loaded in the specimen bag 1062-a.

In this example, the bag 1062-a does not have a specific flat section or base (e.g., like base 1069 in FIG. 23). In some embodiments, the hammock 1044-a and/or the outer bag layer 10446-a are formed of a flexible film or layer, which allows the bag 1062-a to conform to different shapes, thus improving maneuverability when in the patient cavity. In some cases, the hammock and the outer bag layer 10446-a are shaped and sized such that the hammock 1044-a and the outer bag layer 10446-a can be sealed at their proximal ends while leaving a gap/space between the two for the wire channels 10444-a.

FIG. 38B illustrates an example of a specimen bag 1062-b comprising an inner bag layer or hammock 1044-b, an outer bag layer 10446-b, and a plurality of channels 10444-b (e.g., inflation channels), according to various aspects of the disclosure. In this example, the specimen bag 1062-b comprises a clamshell design, where the outer bag layer 10446-b is created by welding together two halves 10551-a, 10551-b of a clamshell. Specifically, the first half 10551-a and the second half 10551-b of the outer bag layer 10446-b are welded around the perimeter of the bag 1062-b except at the opening. In some examples, each of the first and the second half 10551 of the clamshell comprises a flexible film. In some cases, the inner layer/hammock 1044-b and/or the intermediate layers of the specimen bag 1062-b defining the channels 10444-b may also have a clamshell design comprising two films welded together at a joint 10449. Further, the proximal ends of first halves 10551-*a* of each of the outer bag layer, the hammock, and the intermediate layers may be sealed/welded as shown in FIG. 38B. Similarly, the proximal ends of second halves 10551-*b* of each of the outer bag layer, the hammock, and the intermediate layers may also be sealed/welded as shown in FIG. 38B.

It should be noted that, the specimen bag 1062-*a* described in relation to FIG. 38A may also comprise a clamshell design in some embodiments. For example, each of the outer bag layer 10446-*a* and the hammock 1044-*a* may comprise a first and a second half that are welded together at a joint (shown as joint 10449 in FIG. 38B). Further, the proximal ends of the first and second halves of the outer bag layer 10446-*a* and the hammock 1044-*a* may also be sealed/welded as shown in FIG. 38A.

In some cases, the outer layer 10446 and/or the hammock assembly 1044 of the specimen bag(s) 1062 described in relation to FIGS. 38A-38B may be made of a plastic, polyvinyl, nylon, polyurethane, or any other bio-compatible insulating material suitable for use in a live patient.

Figures 38C, 38D:
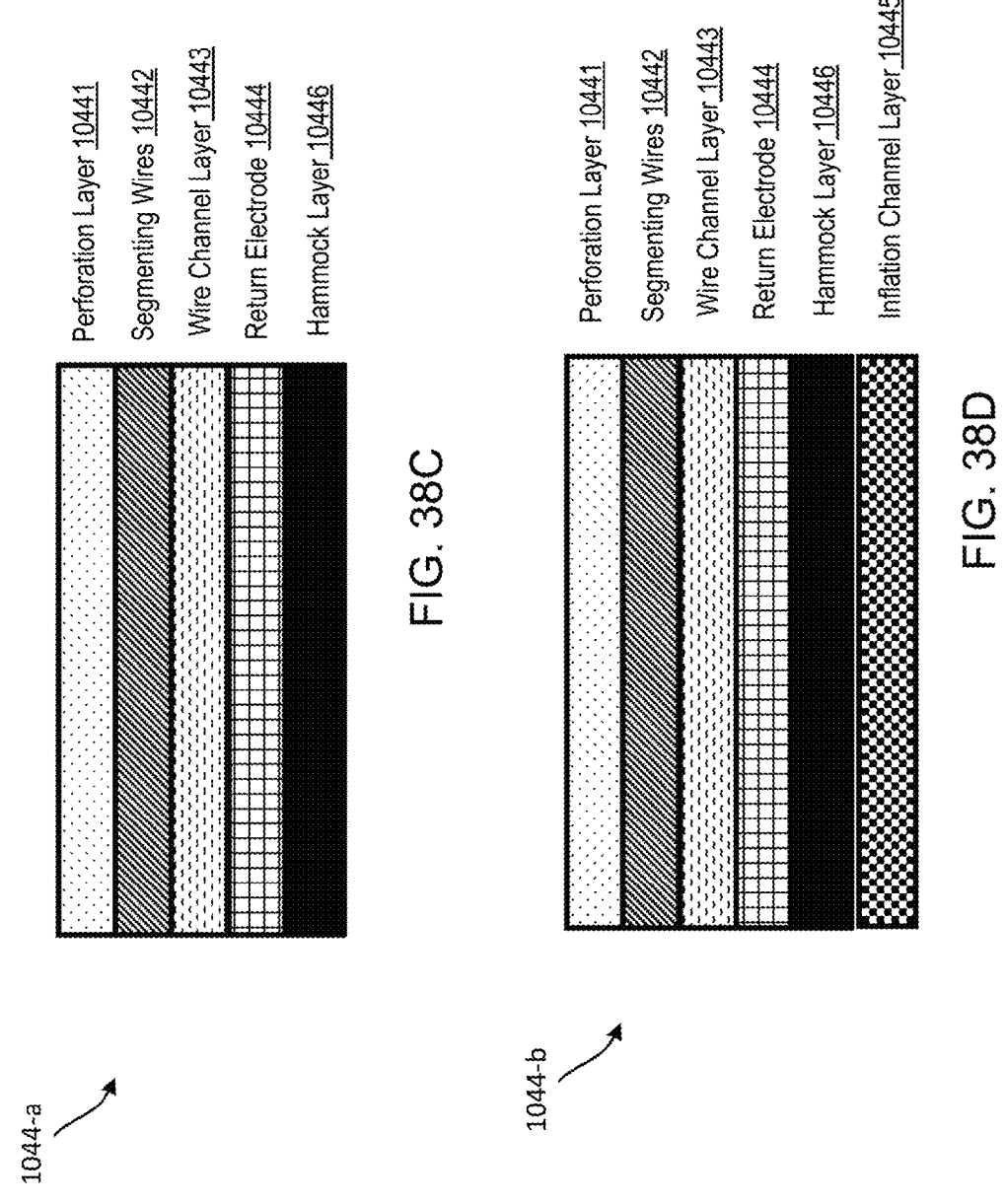
FIG. 38C illustrates an example of a hammock assembly comprising a plurality of layers, according to various aspects of the disclosure.
FIG. 38D illustrates an example of a hammock assembly comprising a plurality of layers, according to various aspects of the disclosure.

FIGS. 38C and 38D depict two alternate cross-sectional views of the layers of a hammock assembly, in accordance with one or more implementations. FIG. 38C shows a cross-section view of the layers that may be incorporated with a hammock 1044-*a* when RF energized wires are used for the cutting procedure, according to various aspects of the disclosure. In this example, the hammock 1044-*a* comprises (as seen from the interior to the exterior of a specimen bag comprising the hammock) a perforation layer 10441, segmenting wires 10442, a wire channel layer 10443, a return electrode layer 10444, and a hammock layer 10446. The peroration layer 10441 in conjunction with the wire channel layer 10443 may help hold the segmenting wires 10442 in place prior to segmentation. In some embodiments, the return electrode layer 10444 may be incorporated onto an interior surface of the hammock layer 10446, for instance, by printing a conductive material (e.g., metal) on the hammock layer 10446. In other cases, the return electrode layer 10444 may be a separate conductive layer attached on the hammock layer 10446. In some cases, the hammock layer 10446 comprises the external facing layer of the hammock 1044-*a*.

FIG. 38D depicts a hammock 1044-*b* comprising an additional inflation channel layer 10445 affixed to an external surface of the hammock layer 10446, in accordance with one or more implementations. In some cases, the hammock 1044-*b* implements one or more aspects of the hammock 1044-*a* described above in relation to FIG. 38C but includes an inflation channel layer 10445 attached on an opposite side of the hammock layer 10446.

In some other cases, the inflation channel layer may be formed along the perimeter of the hammock layer. Furthermore, as noted above, for segmenting wires utilizing a bipolar RF cutting approach or mechanical cutting approach (i.e., no RF energy is applied to the segmenting wires), the return electrode layer 10444 may be optional. In some embodiments, during manufacturing, the various layers depicted and described in relation to FIGS. 38C and/or 38D may be positioned on top of each other and sealed via thermal sealing or welding to form the hammock assembly 1044 (e.g., hammock 1044-*a*, hammock 1044-*b*). The hammock 1044 is then attached to the outer bag layer (e.g., interior surface of the outer bag layer) using one or more of an adhesive, pressure sensitive adhesive, or welding.

Figures 38E, 38F:
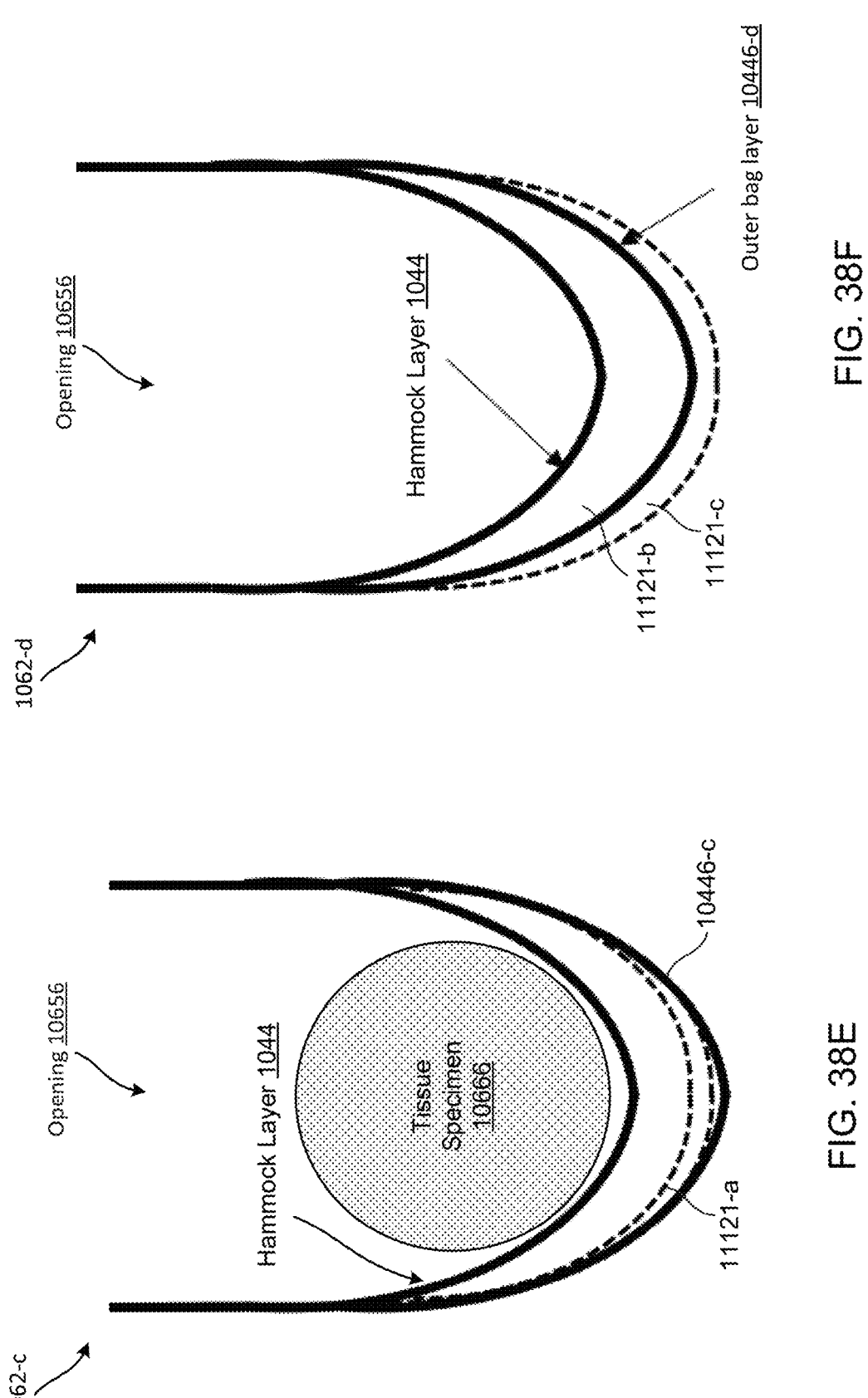
FIG. 38E illustrates an example of a specimen bag comprising a hammock assembly and one or more inflatable channels affixed to an exterior of the hammock assembly, according to various aspects of the disclosure.
FIG. 38F illustrates an example of a specimen bag comprising a hammock assembly and at least one inflatable channel affixed to an exterior of an outer bag layer of the specimen bag, according to various aspects of the disclosure.

FIGS. 38E and 38F depict two alternate inflation channel implementations where the inflation channel(s) are attached to either the interior of the outer bag layer (FIG. 38E) or the exterior of the outer bag layer (FIG. 38F), according to various aspects of the disclosure.

FIG. 38E illustrates a specimen bag 1062-*c* comprising a hammock assembly 1044, a tissue specimen 10666, an outer bag layer 10446-*c*, and one or more inflation channels 11121-*a* positioned in a space between the hammock assembly 1044 and the outer bag layer 10446-*c*.

FIG. 38F illustrates a specimen bag 1062-*d* comprising a hammock assembly 1044, an outer bag layer 10446-*d*, and at least one inflation channel 11121-*c* affixed to the exterior surface of the outer bag layer 10446-*d*. In some cases, the specimen bag 1062-*d* may also include one or more inflation channels 11121-*b*, for instance, positioned between the hammock assembly 1044 and the outer bag layer 10446-*d*.

In some cases, the inflation channel variants described in relation to FIGS. 38E and/or 38F may help with leak detection and/or ease the manufacturing process, to name two non-limiting examples.

Figure 38H:
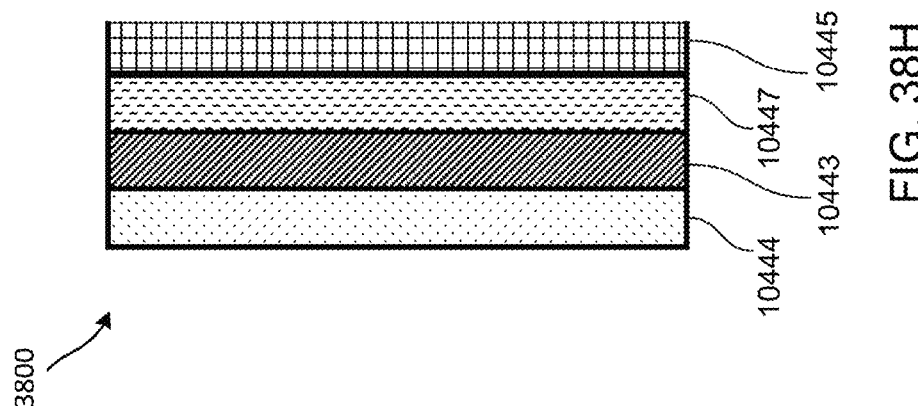
FIG. 38H illustrates a cross-sectional view showing the plurality of layers of the inner bag in FIG. 38G, according to various aspects of the disclosure.
Figure 38G:
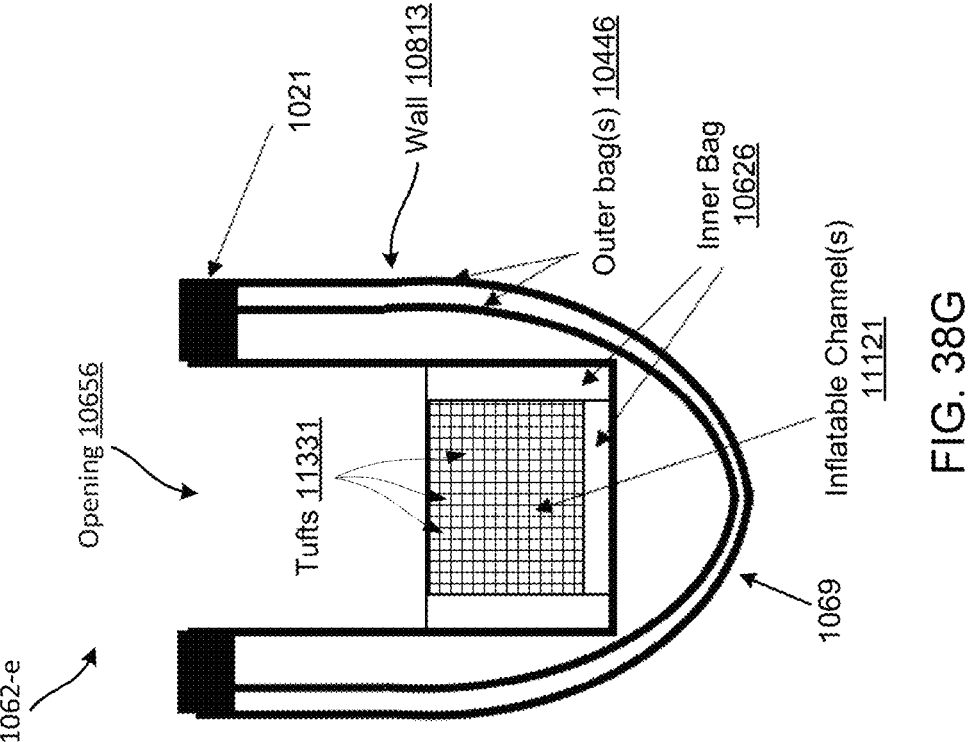
FIG. 38G illustrates an example of a specimen bag having an inner bag, one or more outer bags, and one or more inflatable channels, according to various aspects of the disclosure.

FIG. 38G shows a specimen bag 1062-*e* having an inner bag 10626, one or more outer bag(s) 10446, and inflatable channel(s) 11121 having one or more tufts 11331, according to various aspects of the disclosure. In some cases, spring arms 1021 (e.g., shown as spring arms 1021-*a*, 1021-*b* in the figures above) may be utilized to keep the top opening 10656 of the bag 1062-*e* open during a surgical procedure (e.g., during loading of a tissue specimen). In some cases, the inner bag 10626 may be formed of a flexible material and may have a bottom/base 1069 and one or more sidewalls 10813 that help hold the tissue specimen during segmentation. In some cases, the bag 1062-*e* comprises a plurality of segmenting wires (not shown) that are configured to reduce/slice the tissue specimen into smaller segments for removal through a patient incision. Attached to the exterior of the inner bag 10626 is an inflation channel layer (e.g., inflatable channel 11121 having tufts 11331). In some examples, the inflation channel may be formed from a single layer of film welded onto the inner bag 10626. Alternatively, the inflation channel may be created using two film layers and separately attached to the exterior of the inner bag 10626, for instance, through welding, adhesives, pressure sensitive adhesives, or similar alternatives known in the art. FIG. 38G also shows one or more two-dimensional (2D) outer bag(s) 10446. In some cases, the outer bag(s) 10446 are initially constructed in a 2D construct, like a "clamshell", that when opened create a 3D bag. Such a design may help ease manufacturing, including reducing manufacturing costs, in some cases.

FIG. 38H illustrates a cross-sectional view of a bag wall 3800, according to various aspects of the disclosure. In some examples, the cross-sectional view shown in FIG. 38H depicts the various layers of the bag 1062-*e* described above in relation to FIG. 38G. As seen, the bag wall 3800 comprises a plurality of layers, including a return electrode 10444, a first channel layer 10443 (also referred to as bag film layer 10443), an inflation channel layer 10445, and a gap layer 10447 comprising air (or another fluid) between the inflation channel layer 10445 and the bag film layer 10443. In some cases, the bag film layer 10443 is the same as or substantially similar to the inner bag 10626 in FIG. 38G. As noted above, the inflation channel layer 10445 may be attached to the inner bag (or bag film layer 10443). In some embodiments, the gap 10447 between the layers 10443, 10445 is filled with air or another fluid, which serves to provide thermal and/or electrical insulation between the interior and the exterior of the specimen bag 1062-*e*.

Figure 38I:
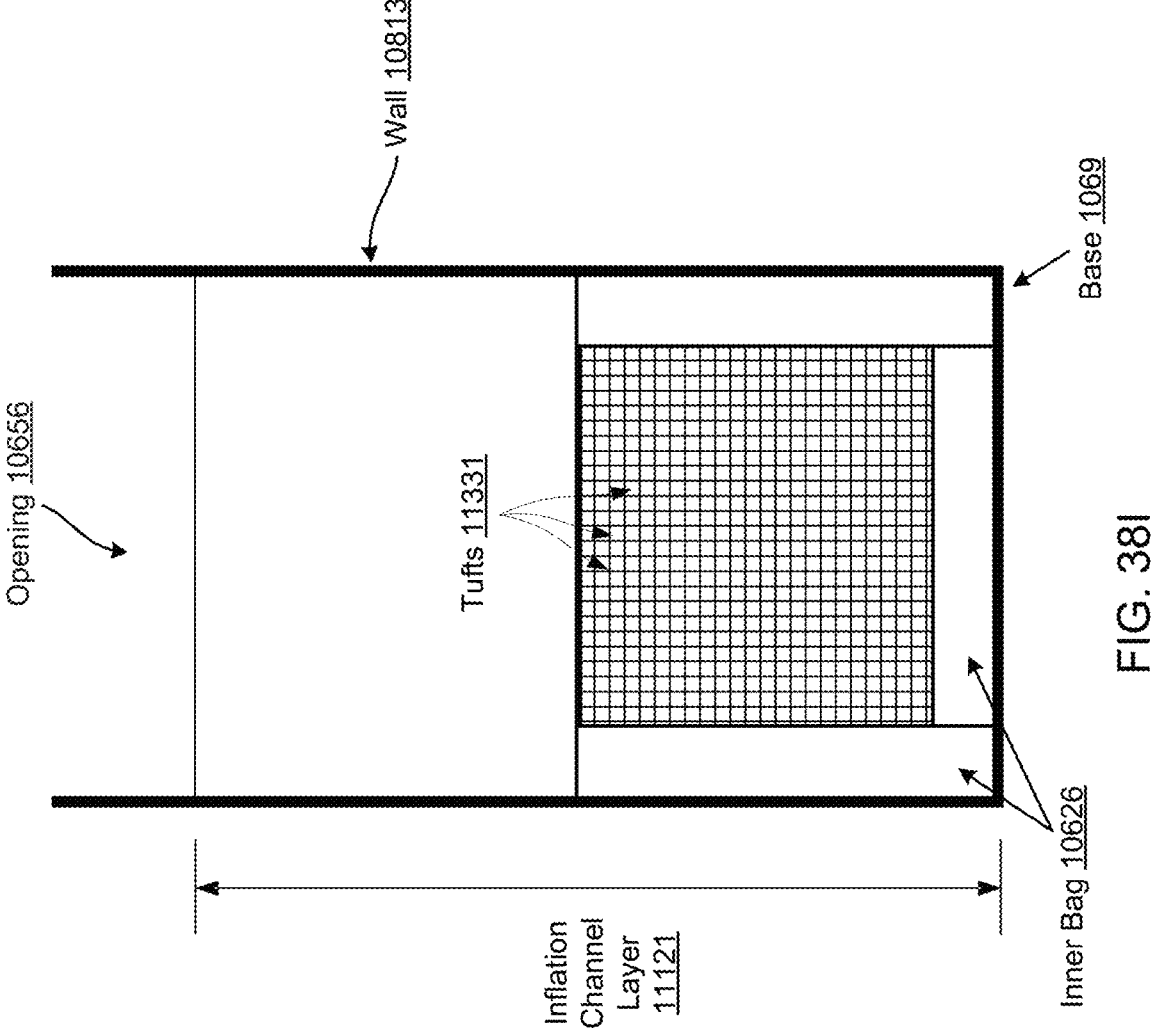
FIG. 38I illustrates an example of a specimen bag having an inflation channel layer, according to various aspects of the disclosure.
Figure 38I:

FIG. 38I illustrates an example of a specimen bag 1062-*f*, according to various aspects of the disclosure. In this example, the specimen bag 1062-*f* includes an inner bag 10626 having an opening 10656, a base 1069 opposite the opening 10656, and one or more sidewalls 10813 between the base and the opening. The inner bag 10626 is shaped and sized to hold a tissue specimen (e.g., shown as tissue specimen 10666 in FIGS. 38A and 38E) during a segmentation procedure. An inflation channel layer, which may be similar or substantially similar to the inflatable channel 11121 in FIG. 38G, is attached on the exterior surface of the inner bag 10626. In some cases, the inflation channel layer (or inflatable channel 11121) may be formed from a single layer of film welded onto the inner bag 10626 layer, where the inflation channel layer extends to or near the top opening of the inner bag 10626. This creates a redundant containment layer that could be used with or without one or more additional bag layers (e.g., outer bag layers).

Figure 41A:
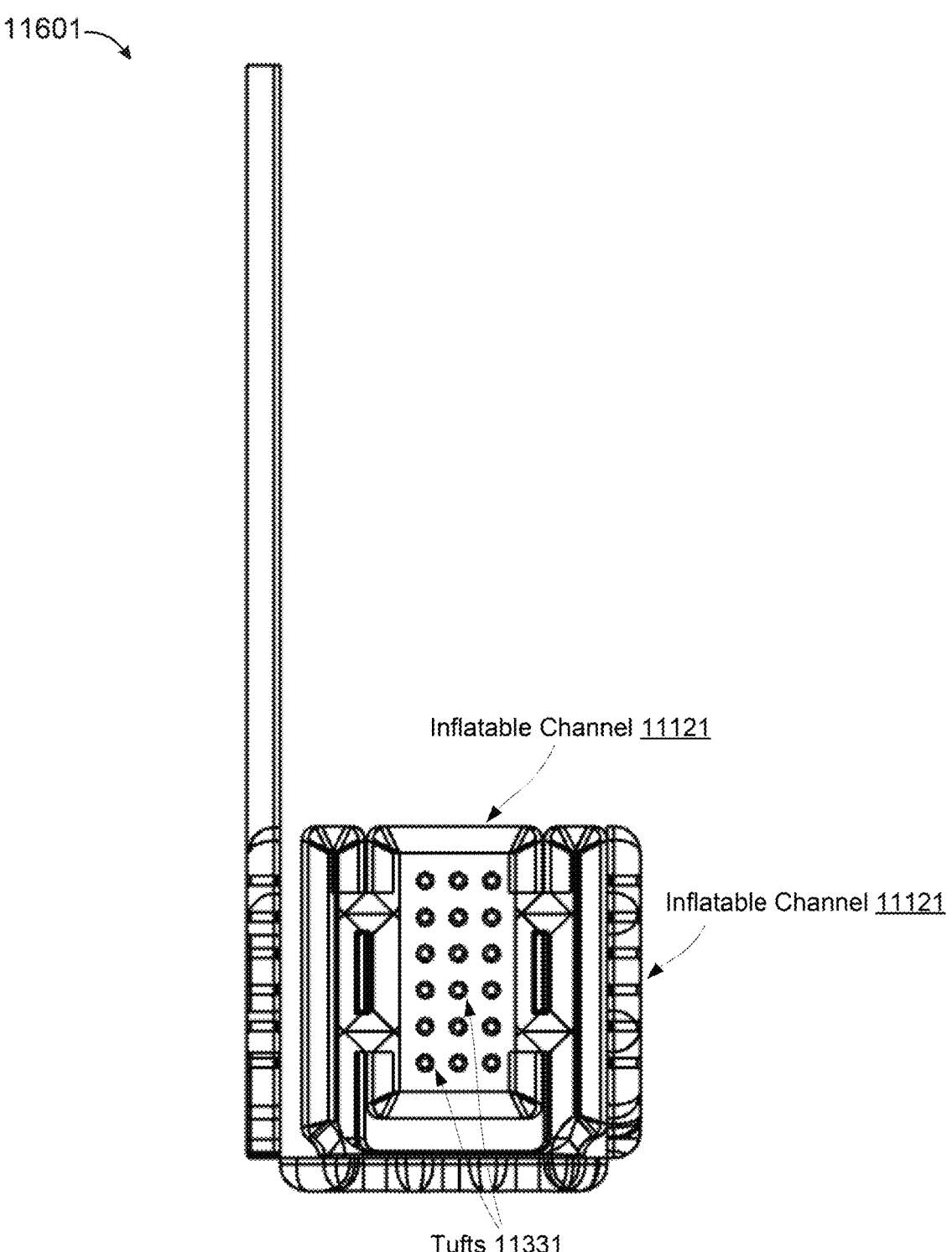
FIG. 41A illustrates a side view of the inflatable channels of the specimen bag system in FIG. 28 showing a plurality of interruptions or tufts, according to various aspects of the present disclosure.
Figure 41B:
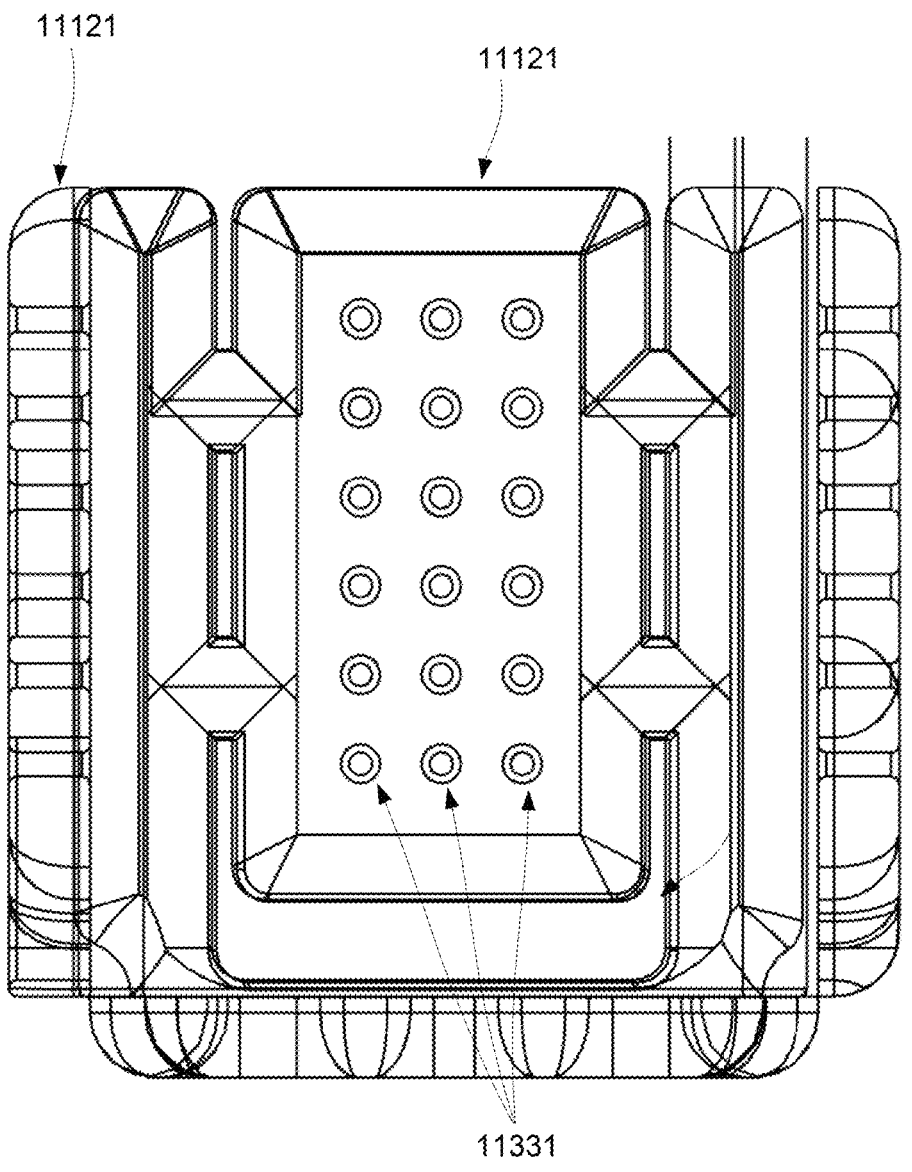
FIG. 41B illustrates a detailed view of the tufts in FIG. 41A, according to various aspects of the disclosure.

FIGS. 41A and 41B illustrate various views of an inflatable channel system 11601 configured for use with any of the specimen bags disclosed herein, including at least specimen bags 1080, 1062, and/or 10101. The inflatable channel system 11601 comprises a plurality of inflatable channels 11121, where the inflatable channels 11121 are similar or substantially similar to the inflatable channels described in relation to FIGS. 28-36 and/or 38A-38I. As noted above, in some embodiments, the inflatable channel(s) 11121 may utilize a tufted design, shown by the tufts 11331. As seen in FIGS. 41A and 41B, the inflatable channels 11121 may comprise a plurality of interruptions (e.g., circular interruptions), such as the tufts 11331, much like a mattress or pillow. In some cases, the tufts 11331 may be optional or may have a different shape (e.g., square) than the one depicted in FIGS. 41A and 41B.

The present disclosure provides devices, systems, and methods for tissue specimen removal utilizing a specimen bag and an integrated connector carrier. FIG. 1 illustrates an example of a specimen bag and connector carrier assembly 10100, according to various aspects of the disclosure. Because the specimen bag and connector carrier assembly 10100 are integrated in the embodiments shown, this may be referred to simply as the "specimen bag assembly". The specimen bag assembly comprises a specimen bag 10101 with a flexible ring 10102 that may be attached to the bag opening. The flexible ring 10102 in the embodiment shown may be made of a metal that is sufficiently thin to be flexible and have spring-like qualities. In the embodiment shown, the flexible ring 10102 comprises two separate spring arms 10107-*a* and 10107-*b* that are coupled with a flexible member 10103 at a distal end and are held securely at a proximal end 10104. It is contemplated that the flexible ring may comprise more or fewer separate components; for example, it may be a single flexible ring, or it may have more separable parts. Though not shown, the specimen bag 10101 may comprise a plurality of segmenting components within or adjacent to its walls.

In an intermediate location between the specimen bag 10101 and a cannula assembly (not shown in FIG. 1), a connector carrier 10105 is shown. The connector carrier 10105 performs several functions which are shown and described in subsequent figures, including holding connectors configured to attach to segmentation equipment, providing a guide to travel along the flexible ring 10102 to close or open the bag opening, providing a channel for a return electrode cable 10108 to extend out away from the bag, to secure the return electrode cable 10108 at the proximal end of the assembly to relieve forces that may be applied by pulling the return electrode cable 10108, and to provide a lock that can be integrated with a cannula or outer tube to provide a mechanical anchor at the distal most position of the outer tube. The return electrode 10108 may be configured to be plugged in to the piece of segmenting equipment in embodiments where the segmenting equipment is powered by RF power. In such embodiments, the return electrode 10108, which may be attached to conductive material within the specimen bag 10101, may complete a circuit created by the segmenting equipment and the segmenting components (e.g., wire loops) within the specimen bag 10101. Embodiments of RF powered segmenting devices are shown and described throughout this disclosure.

Figure 39:
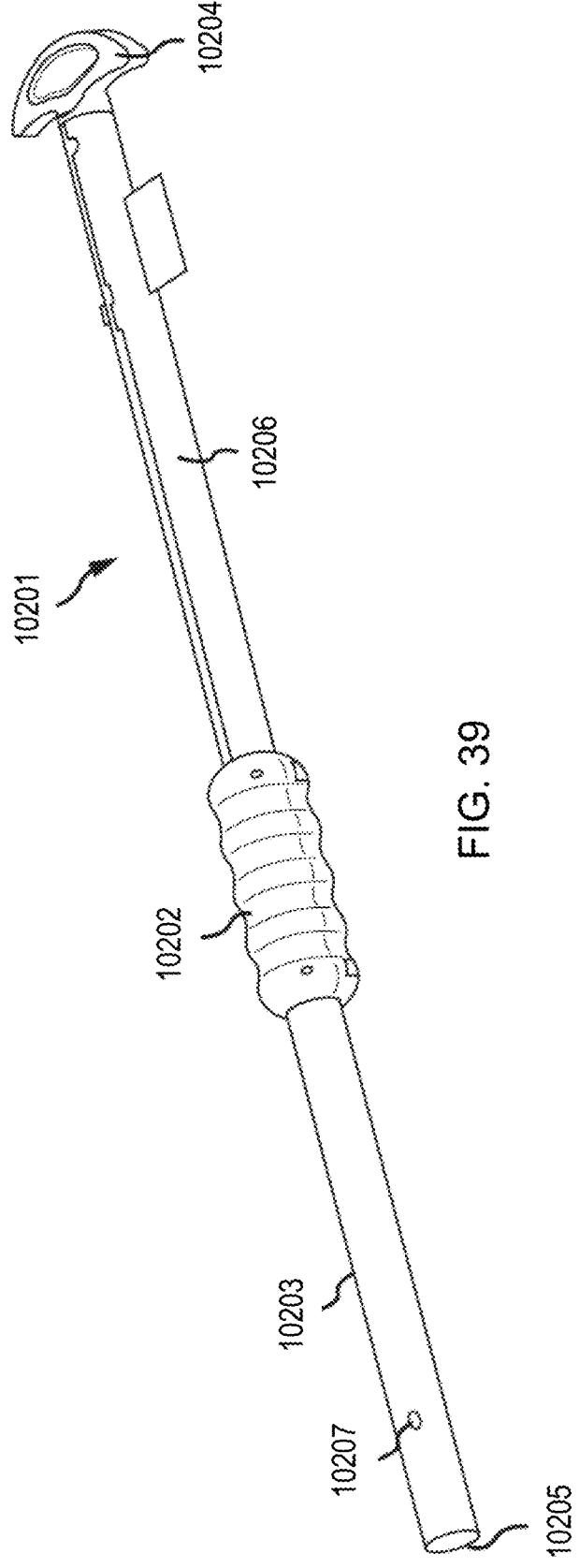
FIG. 39 illustrates an embodiment of an introducer tube of the specimen removal bag system of the present disclosure in a first retracted position, wherein the specimen bag is retained within an outer tube of the introducer tube, in accordance with one or more implementations.

FIG. 39 illustrates an example of an introducer tube 10201 (or cannula assembly 10201) into which the connector carrier 10105 (from FIG. 1, not shown in FIG. 39) may be loaded during manufacturing. In some embodiments, the connector carrier 10105 may be positioned in close proximity to a mechanical anchor (e.g., mechanical anchor 10802 in FIG. 1). In some cases, the introducer tube or cannula assembly 10201 is shaped and sized to receive an inner tube 10206 and an outer tube 10203. In some examples, the outer tube 10203 is shaped and sized to receive the inner tube 10206. Further, the inner tube 10206 may also comprise a proximal end grip 10204. During manufacturing, the specimen bag (e.g., specimen bag 10101, bag 1062, etc.) may be rolled and positioned inside the outer tube 10203. After the introducer tube 10201 is inserted through the incision site, the specimen bag may be advanced into the patient by advancing the inner tube 10206, which pushes the inner tube 10206 into the outer tube 10203. In some cases, a medical grip portion 10202 may be utilized to attach the inner tube 10206 and the outer tube 10203 in such a way that they may be disposed in any position between fully extended and fully enveloped. That is, the inner and outer tubes may be disposed end-to-end, or the inner tube within the outer tube, or any position in between.

When the bag 10101 advances, the spring arm assembly (e.g., spring arms 1021-*a*, 1021-*b*) begin opening the bag as the spring arms extend beyond the distal edge 10205 of the outer tube 10203. As the connector carrier 10105 reaches the distal edge 10205, a mechanical anchor (e.g., mechanical anchor 10802 in FIG. 1) integrated into a top portion of the connector carrier 10105 interfaces with an opening 10207 (also referred to herein as a "securing opening") in the outer tube 10203 to secure it in a position within the introducer tube or cannula assembly 10201. In some embodiments, the mechanical anchor 10802 is implemented as a spring detent mechanism, which remains in a depressed position inside the introducer tube 10201 until it reaches the opening 10207 and pops up, securing the connector carrier 10105 in that position within the outer tube 10203. In some cases, for instance, when the mechanical anchor 10802 of the connector carrier 10105 is secured in the opening 10207, the user can control the opening and closing of the specimen bag by advancing or retracting the inner tube 10206. In some cases, a hitch or another applicable element is configured to attach to the spring arm assembly and movable by the inner tube 10206. The movement of the hitch causes the spring arms to slide around the sides of the connector carrier 10105. As noted above, the spring arms may be coupled to the bag and/or used to hold the bag. Thus, the spring arm assembly described in relation to the figures above may be movable between an unconstrained position, in which case the specimen bag is in an open position, and a retracted position, in which the bag opening is closed or bunched up against the distal edge 10205 of the outer tube 10203.

Figure 40:
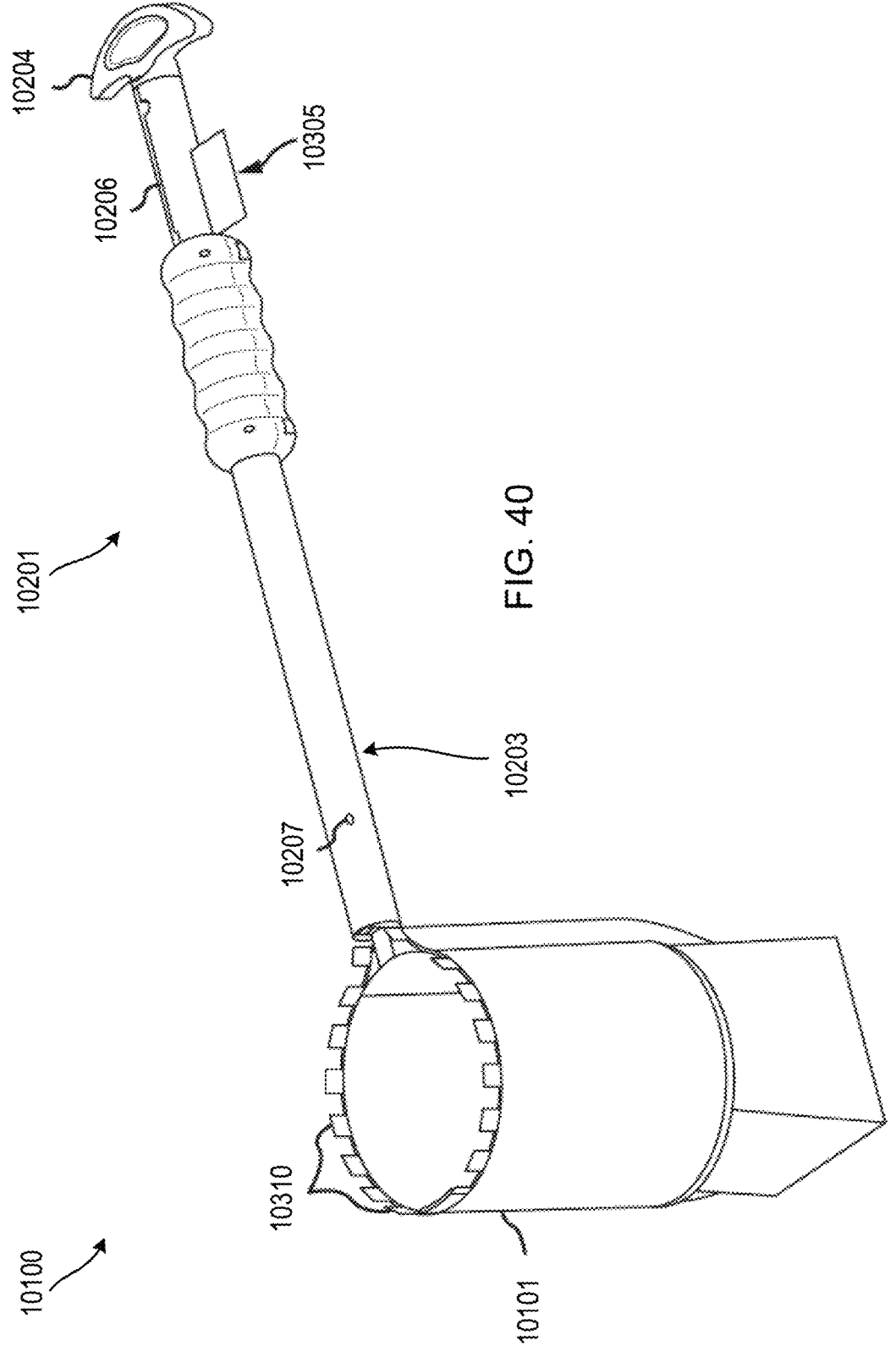
FIG. 40 illustrates an embodiment of the specimen removal bag system with the introducer tube of FIG. 39 in a second advanced position, wherein the specimen bag is deployed into an open position, in accordance with one or more implementations.

FIG. 40 illustrates an embodiment of the connector carrier assembly 10100 with the introducer tube 10201 of FIG. 39 in a second advanced position, wherein the specimen bag 10101 is deployed into an open position, in accordance with one or more implementations. FIG. 40 shows the inner tube 10206 pushed in all the way such that a majority of the inner tube 10206 is positioned within the outer tube 10203. As a result, the specimen bag 10101 and spring arm assembly (not shown here but shown as spring arm assembly in FIGS. 18 and 19) are pushed out of the outer tube 10203. In this example, the spring arm assembly is not depicted to show that the top of the specimen bag 10101 comprises a plurality of optional flexible loops 10310 for attaching the spring arm assembly to the specimen bag 10101. In some cases, the optional flexible loops 10310 may be bunched up together (e.g., when the specimen bag is rolled up and positioned within the outer tube 10203), or they can be spread apart when the flexible ring/spring arm assembly is advanced to hold open the top of the specimen bag 10101.

In some cases, the outer tube 10203 and inner tube 10206 (i.e., the entire introducer tube 10201) may be detached from the specimen bag assembly 10101, for instance, after bag exteriorization. This detachment may be performed by advancing the inner tube 10206 beyond the position where the optional mechanical anchor 10802 locks into the opening 10207 of the outer tube. In some cases, the inner tube 10206 may be advanced by releasing the mechanical anchor 10802 from the opening 10207. In one non-limiting example, the mechanical anchor 10802 comprises a spring detent, where the spring can be manually depressed while advancing the inner tube 10206. Further, the inner tube 10206 may include a mechanical stop 10305 at or near the proximal grip portion 10204, that can be inserted into the inner tube 10206 during manufacturing and shipment, thereby restricting the advancement of the inner tube 10206 to the location that secures the anchor 10802 into the outer tube 10203. In some cases, the user may remove the mechanical stop 10305 to allow the inner tube 10206 to advance and enable the outer tube 10203 to be released from the mechanical anchor 10802.

Figure 2:
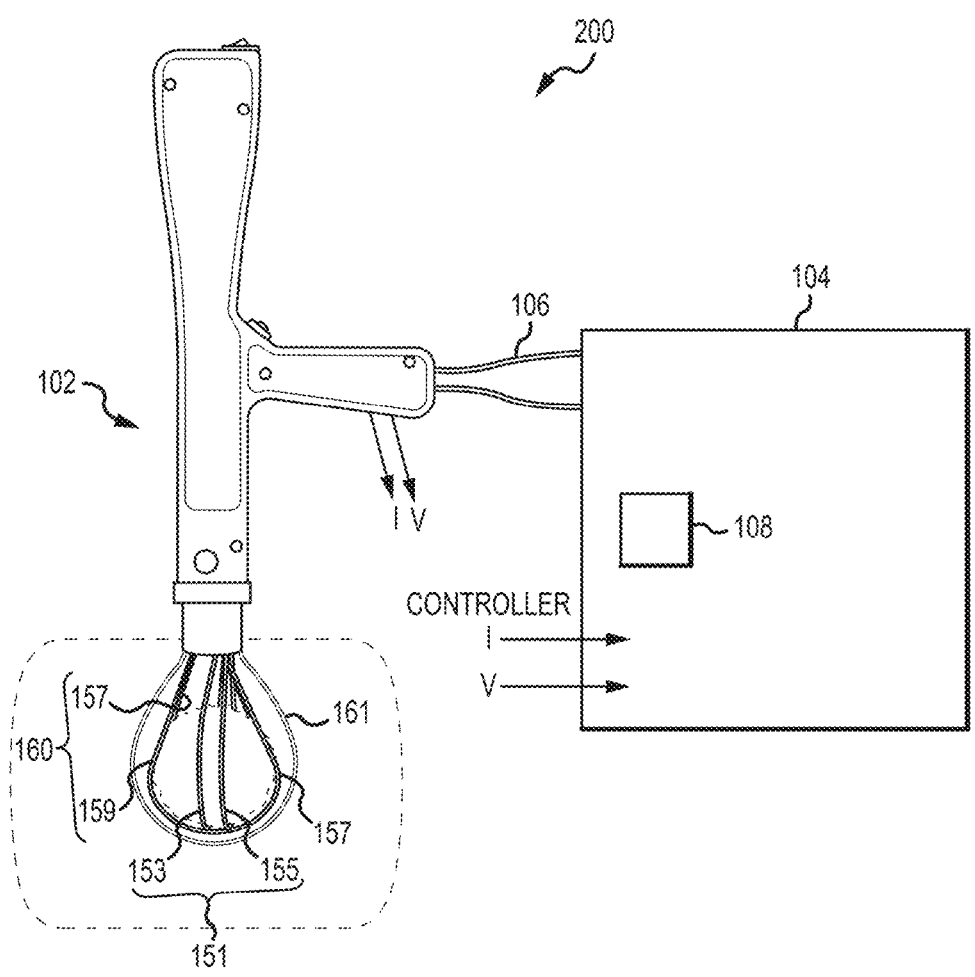
FIG. 2 illustrates a tissue segmentation device according to some embodiments of the present disclosure.

In one exemplary application, and as illustrated in FIG. 2, an advanced electrosurgical system 200 may be provided, according to various aspects of the disclosure. The system 200 may be configured to perform some or all of the functions, such as tissue segmentation and/or removal, described in Applicant's International Application PCT/US15/41407, entitled Large Volume Tissue Reduction and Removal System and Method, filed on Jul. 21, 2015, and having a priority date of Jul. 22, 2014, the entire contents of which are incorporated herein by reference for all purposes, as if fully set forth herein. The system 200 may include an electrosurgical device 102 and a generator 104 (e.g., RF generator) coupled together by a number of leads 106. The system 200 further includes a controller 108, a bag 161, and a plurality of electrode/wire sets 151, 160. In some cases, each electrode/wire set comprises a plurality of electrodes/wires. For instance, the first electrode set 160 comprises electrodes/wires 157, 159, and the second electrode set comprises electrodes/wires 153, 155. In this example, the generator 104 includes the controller 108. In some cases, the bag 161 is similar or substantially similar to the specimen bag(s) disclosed herein, including at least specimen bag 1062.

Except as where otherwise stated herein, the term "segmentation device" shall be understood to include a device for dividing tissue, and may include a mechanical segmentation action, and/or an electrosurgical dissection action, for example a bipolar segmentation action, or a monopolar action.

Figure 3:
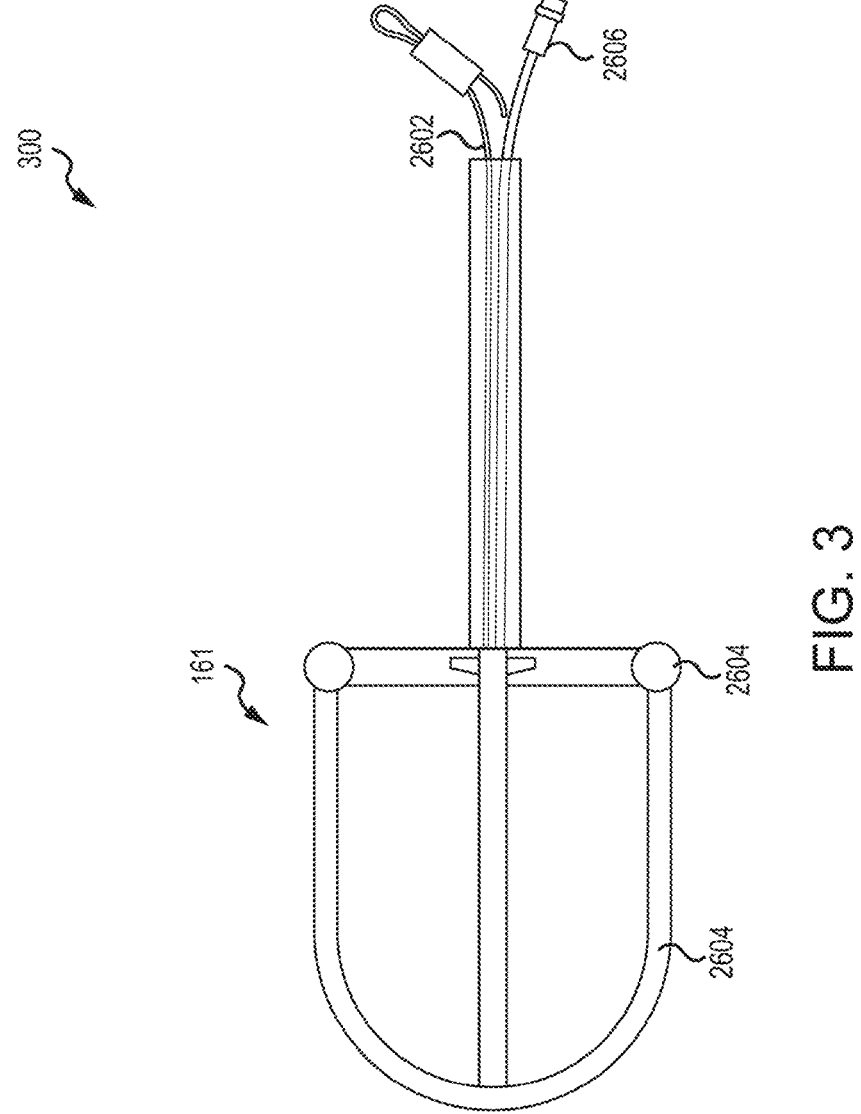
FIG. 3 is a side section view of an inflator, according to various aspects of the present disclosure.

In some embodiments, and as illustrated in FIG. 3, a return cable 2602 integrated with tubing to form a secure tether may be provided to enable a user to exteriorize the bag 161. FIG. 3 illustrates a side section view of an inflator 300, according to various aspects of the disclosure. In some embodiments, the removal bag 161 includes a plurality of inflation areas 2604 within the bag that can be inflated using low pressure air. These inflation areas 2604 are used to provide rigidity to the bag opening and/or the side walls of bag 161 to assist in loading the tissue specimen into the bag 161. The inflation areas 2604 may include or be coupled to a common inflation tube 2606 that, along with the return electrode cable 2602, protrudes out of the patient when the removal bag 161 is inserted to load the tissue specimen.

In some embodiments, the return electrode cable 2602 and inflation tube 2606 are mechanically attached together and mechanically supported where they exit the removal bag 161 such that they can be used as a means to pull the bag 161 toward the incision site after the tissue specimen is loaded. After deflating the bag 161, the bag opening may be pulled through the incision site by pulling the return cable 2602 and inflation tube 2606 assembly until the bag opening or a portion of the bag opening is exteriorized allowing the user to pull the remaining bag opening out of the patient. This integration of the return electrode cable 2602 and tubing 2606 may be a molded assembly, a film applied around both components, layered together as one assembly, tied together along the length of common attachment, or can bonded using adhesive or other means.

Figure 4:
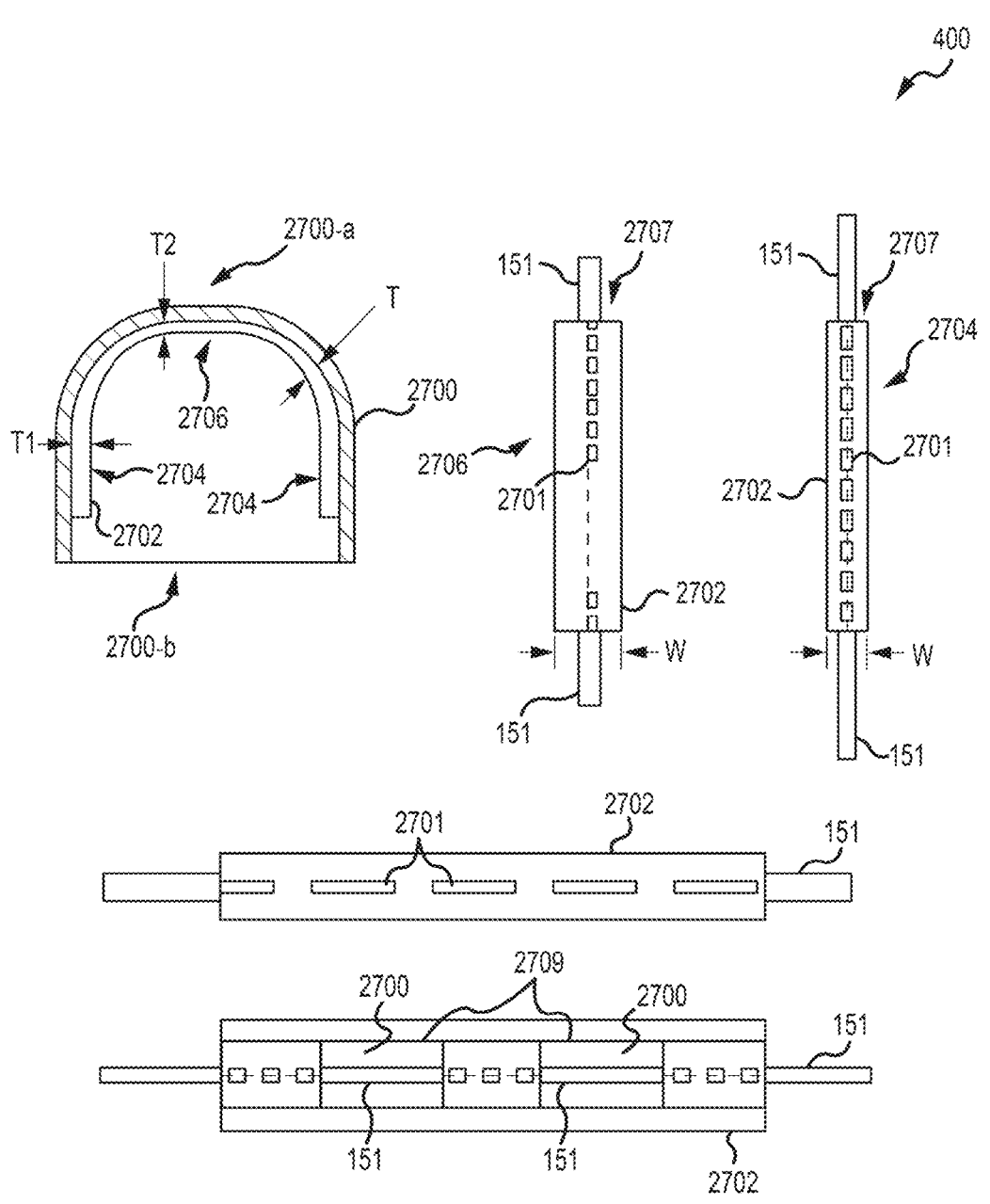
FIG. 4 illustrates several views of tissue removal bag components, according to various aspects of the present disclosure.

Turning now to FIG. 4, a tissue removal bag system 400 may be provided for the system 200, where the tissue removal bag system comprises a bag 2700, in accordance with one or more implementations. The bag 2700 may be similar or substantially similar to one or more of the bag(s) 10101, 161, 1062, and/or 1080 described herein. The bag 2700 may utilize a thin layer of film 2702 that contains perforations 2701 to secure the electrode(s)/wire(s) to the interior surface of the bag 2700. These perforations 2701 may be designed to control the release of the electrode(s)/wire(s) during the pretension step or may be designed to partially release the electrode(s)/wire(s) at select locations and to release the electrode(s)/wire(s) at the remaining locations during the travel of the electrode(s)/wire(s) during cutting. Control of the release of the electrode(s)/wire(s) during pre-tensioning may be achieved by selection of the perforation per length configuration, combined with the thickness, T, and elasticity of the film 2702 containing the perforations 2701, along with the thickness and rigidity of the material in which the perforation layer is attached.

In addition, the width, W, of the dimension in which the film 2702 is not attached to the bag 2700 defines a wire channel 2707. This wire channel 2707 (also shown as wire channel layer 10443 in FIG. 21B) is an important dimension related to the ability of a wire (e.g., electrode/wire set 151 as previously illustrated, or any wire 10428 or electrode described herein) to find the perforation 2701 when the tensioning force is applied so that it creates the separation required to release the electrode(s)/wire(s) 151. This width, W, combined with the elasticity and/or thickness, T, of the material of the film 2702, can be adjusted in addition to the perforation per length values and patterns previously described to provide the optimal wire release performance.

In some embodiments, the width W of the wire channel 2707 for a tissue removal bag 2700 is less than 0.5 centimeters (or less than about 0.200 inches); in some embodiments, the width is less than about 1.63 centimeters (or less than about 0.064 inches). Another means to help increase the probability of the electrode/wire set 151 separating the perforations is to have multiple perforation lines 2701 in parallel to each other in the film 2702 so that as the wires are routed in the channel 2707, the chance of finding the line of perforations 2701 is greater.

Selection of the appropriate combination of these values can provide the release of the electrode(s)/wire(s) in a manner that advances as the electrode(s)/wire(s) advance during cutting and can guide the electrode(s)/wire(s) along a perforation channel 2707, resulting in a more predictable segmentation cut. This may be accomplished with the same perforation per length values across some or all sections having the perforations 2701, can be enhanced by using different perforation per length values in different sections, can be a linear, logarithmic, or other pattern of increasing or decreasing perforation per length values, or can be patterns of perforations 2701 followed by open areas (windows) 2709 to enhance the separation as the electrode(s)/wire(s) travel(s).

Those skilled in the art will appreciate that as multiple wires are used within the bag, intersection points are created where a wire set intended to apply power such as RF energy to the tissue crosses in close proximity to the wire sets that are not intended to have power or RF energy. Some amount of power will tend to couple, either capacitively, inductively or conductively, to the inactive wire sets. This can result in cutting of unintended wire sets which can lower the current density, as the total active electrode surface area is increased, such that the desired cutting performance is not achieve. As such, this coupling must be managed to avoid unintended wire set cutting.

Figure 16:
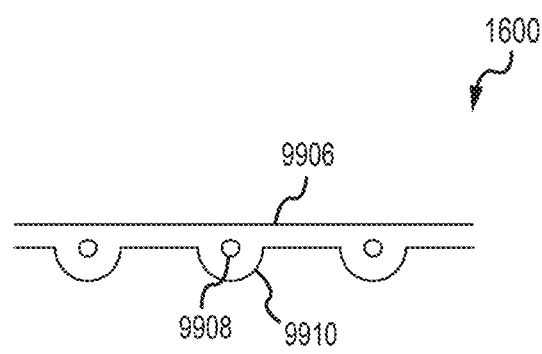
FIG. 16 illustrates some components for wire management, according to various aspects of the present disclosure.

With brief reference to FIG. 16, in some embodiments, one or more electrode wires 9908 may be molded in or contained in a film 9910 or portion of a bag wall 9906. FIG. 16 illustrates a top view 1600 showing how some electrode wires 9908 might be positioned, in accordance with one or more implementations. Furthermore, FIG. 16 implements one or more aspects of FIGS. 21A and/or 21B.

In some embodiments, the coupling can be managed electrically by providing a higher isolation between the intended and unintended wire sets. This can be achieved by aligning the perforation portion of the channels at the intersection points. This provides the greatest benefit for conductive coupling and provides a higher dielectric for capacitive coupling.

In addition to increasing the isolation, the overall amplitude of the electric field can be reduced. This is achieved by controlling the amount of exposure the active wire has with the tissue. As the contact between the wire and tissue is increased, the effective impedance is reduced resulting in a lower electrical field amplitude along the wire. In addition, as the voltage on the wire sets reaches a level where arcing begins, the arc path will preferentially be through the tissue and not to the unintended wire sets.

The coupling can be managed mechanically be providing a higher mechanical load to the wire sets intended to cut verses the unintended wire sets. This can be achieved with separate pre-tension forces, or with different forces applied for the duration of the cutting process. If the coupling is observed between the intended and unintended wire sets, the differential force between the two wire sets will increase the separation between the two as the intended wire set advanced through the tissue. The increased separation will reduce the amplitude of the coupling between the two wire sets, and ultimately to an insignificant level.

With continued reference to FIG. 4, perforations 2701 in the bag material, or alternatively, a hammock assembly, may be used as a temporary method to secure or contain the wires until a force or force aided by temperature rise can allow the release of the wire. For instance, FIG. 21B described above, depicts a film/perforation layer 10441 positioned on top of an active electrode 10442. In some cases, the film/perforation layer 10441 may be selected to have a relatively low melting point (e.g., <50 degrees C., <60 degrees C.). Those skilled in the art will understand that if the material containing the perforations or attaching the wires is a film that has a very low temperature melting point, the wire channels may be configured to release primarily with the temperature created form the power or RF energy activation. In this manner, the mechanical force is a secondary means of releasing the wires from the bag and the active electrode wires activated for cutting will more easily release from the channels upon initiation.

A feature may be combined with the wires to enhance the ability of the wire sets to break away from the bag perforations and/or perforation layer, such as perforation layer 10441 of the hammock assembly 1044 described in relation to FIG. 21B. For example, the wires in electrode/wire set 151 (also shown as active electrode 10442 in FIG. 21B) may have a wedge shape feature that is attached to the wire or Teflon tubing to cut or improve the tearing of the perforations as the wire moves through the tissue.

Some embodiments may be configured to reduce the likelihood of a cut tissue segment that is too large to remove through the incision site. In some embodiments, multiple layers of active electrode wire sets are attached with perforations to layers of the bag.

For example, if an electrosurgical device 102 is designed to have four tensioning mechanisms that apply power to four separate active electrode wire sets, the bag may include an outer layer, a second layer that has the return electrode coupled to the outer layer, and a series of internal layers stacked inside the bag. Each of these internal layers may be an insulated layer with perforations running the length of the layer that has four active electrode wire sets attached with perforations. These layers may conform to the shape of the outer layer so that they can be easily inserted into the outer layer. The layers may also have an opening in the bottom area of each layer so that the return electrode is exposed to the tissue when the internal layers are in place. The user may attach the connectors of the active electrode wire sets from the innermost layer to the electrosurgical device 102.

The tissue segmentation may be performed as described in Applicant's application PCT/US15/41407. When the segmentation is completed and the wires are removed from the layer, the layer may be removed by the surgeon by hand, such as by pulling on the exposed portion of the inner layer and causing the perforations in of the layer to separate, allowing the film to be removed. This removal exposes the next set of active electrode wire set connectors. A second electrosurgical device 102, or a device that can be reloaded to the fully extended position, can now be connected to the tissue removal bag in the same manner as previously described. Those skilled in the art can understand that this increases the number of segmentation cuts and reduces the chance that a large tissue segment will remain after all segmentation steps are completed. The layers of the bag may be constructed such that each internal layer is rotated slightly from all other layers to further reduce the likelihood of leaving a large tissue segment after all segmentation steps are completed.

Continuing with FIG. 4, in some embodiments, the film 2702 is separated into a plurality of different regions, and in some embodiments, two regions. The bottom region 2700-*a* may include an additional region 2706, which may be a hemisphere region as illustrated, although those skilled in the art will understand that a box shape or any other shape may be selected depending on the particular purpose of the bag 2700. The sides of the bag 2700 may have the side region 2704. Due to the forces applied to the tissue specimen by the electrode(s)/wire(s) during pre-tension and cutting, the force in the bottom region 2706 may be less than the forces in the side region 2704, thereby biasing a release of wires from the side before a release from the bottom. To counteract this tendency, those skilled in the art will understand that it may be desirable to provide a film 2702 having a first thickness, T1, at a side portion that is different from, such as thicker than, a second thickness, T2, at a bottom portion. It may be desirable to provide a side section of the film 2702 having a first pattern of perforations 2701 and a bottom section of the film 2702 having a second pattern of perforations 2701 different from the first pattern of perforations 2701.

For example, FIG. 4 illustrates an embodiment in which the bottom region 2706 has a 0.001-inch (25.40 μm) thick film and a 12 tooth per inch (about 4.72 tooth per centimeter) perforation to provide a lower break force to separate the perforations 2701. The side region 2704 may have a film 2702 that is about 0.0022 inches (about 55.88 μm) thick and an 8 tooth per inch (about 3.15 tooth per centimeter) perforation 2701 to ensure that a slightly higher force is required to separate the perforations 2701 in the side region 2704 as compared to the bottom region 2700-*a*. This embodiment takes advantage of the fact that during manipulation and loading of the tissue specimen, higher forces occur on the side regions 2704 than the bottom region 2700-*a*, allowing a lower perforation force to be used in the bottom region 2700-*a* without concern for failure during the loading process. This configuration also takes advantage of the higher side region force so that the electrode(s)/wire(s) do not fully and/or prematurely release with or during a pre-tension step. This allows the electrode(s)/wire(s) to release during cutting such that the perforations 2701 act as a guide to align the travel of the wires through the tissue with the perforations 2701.

Other examples of perforation patterns are illustrated in FIG. 4. In some embodiments, a method of manufacturing a retrieval bag for an electrosurgical device may be provided. The method may include providing a flexible bag 2700 having an interior region at least partially coated with a film 2702, and perforating the film in a pattern, the pattern configured to control a release pattern of at least one electrosurgical electrode or wire. The method may include providing a film 2702 having a first thickness, T1, on a side portion and a second thickness, T2, on a bottom portion, the second thickness, T2, different from the first thickness, T1.

In some embodiments, providing open windows 2709, or omission of the perforation layer at desired intervals or location(s), aides in wire release from the bag, as illustrated in FIG. 4. These windows 2709 do not constrain the wire(s) and enable direct contact between the active electrode wire and the tissue. The area(s) of perforation, or perforation walls, provide a temporary attachment of the wires to maintain alignment.

The ratio of windows 2709 to perforation walls may be adjusted or selected in a manner similar to the perforation per length value, to control the force required to release the wire 151 through the perforations. In addition, because the perforation walls cover the active electrode wire(s) prior to release, the perforation walls may provide an isolation layer and/or the isolation layer may have the perforation walls.

Cut initiation and the early cut performance may be enhanced in embodiments having windows 2709 placed in desired locations around the tissue specimen. For example, due to the mechanical load and electric field distribution of the wire(s), the active electrode wire(s) may preferentially begin cut initiation at a first portion of the bag side walls. Placing a window 2709 at or near the first portion will enhance this initiation. Placing a wall at or near a second portion, in contrast, moves the cut initiation towards the second portion. By contrast, placing a perforation wall at or near the first portion may restrict the cut initiation at the first portion, unless the voltage created on the active electrode wire 151 can create an arc through the perforation wall. The windows and/or perforation walls may thus be configured such that a selected portion of the bag will provide the first portion of the tissue being cut.

That is, the cut may be controlled so as to travel from a first region of the tissue to a second region of the tissue.

Figure 5:
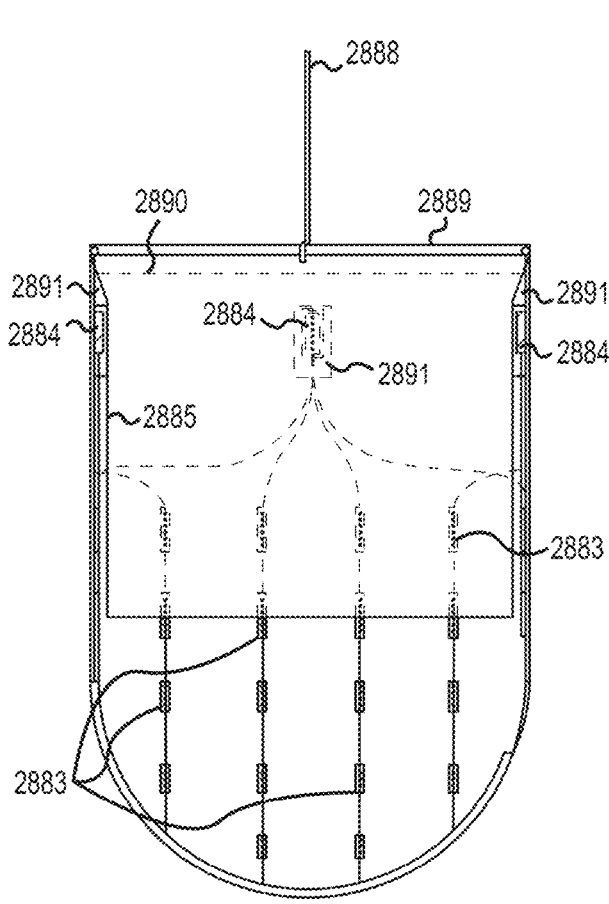
FIG. 5 illustrates a bag having an apron, according to various aspects of the present disclosure.

FIG. 5 illustrates an example of a bag 500 having an apron and perforation walls, according to various aspects of the disclosure. In some cases, the perforation walls 2883 do not extend to the bag opening region, allowing (1) the proximal end of the electrode(s) or wires(s) to be terminated into connectors 2884 during manufacturing, (2) the user to easily guide the wire set connector, or (3) termination of the wire(s) to the corresponding receptacle in the segmentation instrument or other device intended to attach to the wire connectors. Having the portion of the electrode(s) or wire(s) not secured by the perforation walls near the bag opening allows the wires to freely extend away from the interior surface of the bag.

Figure 17:
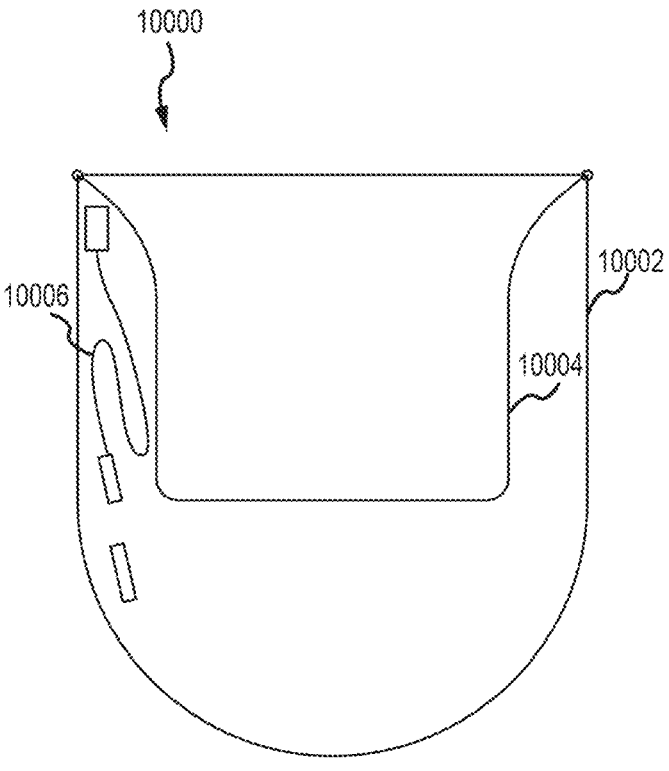
FIG. 17 illustrates a side section view of some components of a wire management system, according to various aspects of the present disclosure.

With brief reference to FIG. 17, a bag 10000 may include an outer bag 10002 and an apron 10004 for managing placement of the wires/electrodes 10006. While not necessary, the apron 10004 (or apron 2885 in FIG. 5) may include one or more openings.

Turning now to FIG. 5, an "apron" or additional layer of film 2885 is provided in the bag to protect the wires from damage during loading. This apron may be attached to the bag opening at the proximal end or near the bag opening. The apron may be of a cylindrical shape that is continuous or a series of segments that extend around the circumference of the inside of the bag. The apron may be positioned so that the wires and/or wire connectors are located between the apron and another feature in the bag. The apron may extend distally along the interior surface of the bag to a point near or beyond the perforations so that any wire not contained by the perforations will remain beneath the apron. With the apron, the tissue will not directly contact the wires or wire connectors and may be easier to load. The apron may also protect the wires during loading, manipulation of the bag and exteriorization.

The apron 2885 may have one or more pouches 2881 to temporary hold proximal portions or connectors of the wire sets.

Those skilled in the art will understand that the apron may have benefit with any feature located on the bag surface that can interfere with loading of the specimen, and/or may be a benefit to protect during the loading, manipulation, exteriorization or other procedural steps. In some embodiments, an apron 2885 may isolate or protect an active electrode, wire or electrode/wire set 151 as previously described, a mechanical member such as a wire, cable or mesh, a protrusion of the bag surface, monitoring electrodes, temperature sensors, pressure sensors, features embedded into the bag, and/or other items that are located in the bag, placed in the bag or used in proximity of the interior surface of the bag.

The apron 2885 may also be used as a containment flap 2986 (see FIG. 6) to help retain the contents of the bag after loading. The containment flap 2986 may be sized to remain in between the loaded tissue specimen and the interior surface of the bag such that the apron does not restrict the tissue from being loaded into the bag. The containment flap may also be sized such that when the tissue is loaded into the bag the tissue falls, or is placed below, the distal most edge of the apron, or the distal most edge of the containment flap may be raised above the tissue after loading is complete. As a result, the apron 2885 may be configured to restrict premature or unintentional removal or displacement of the tissue.

In some embodiments, the electrosurgical device 102 may have a bag with an apron 2885 that is removable. A removable apron may be selectively positioned interior of the bag and one or more cutting electrode wires 151. The removable apron may be movable relative to the bag to expose the wires 151.

Figure 6:
FIG. 6 illustrates a bag having a drawstring, according to various aspects of the present disclosure.
Figure 6:
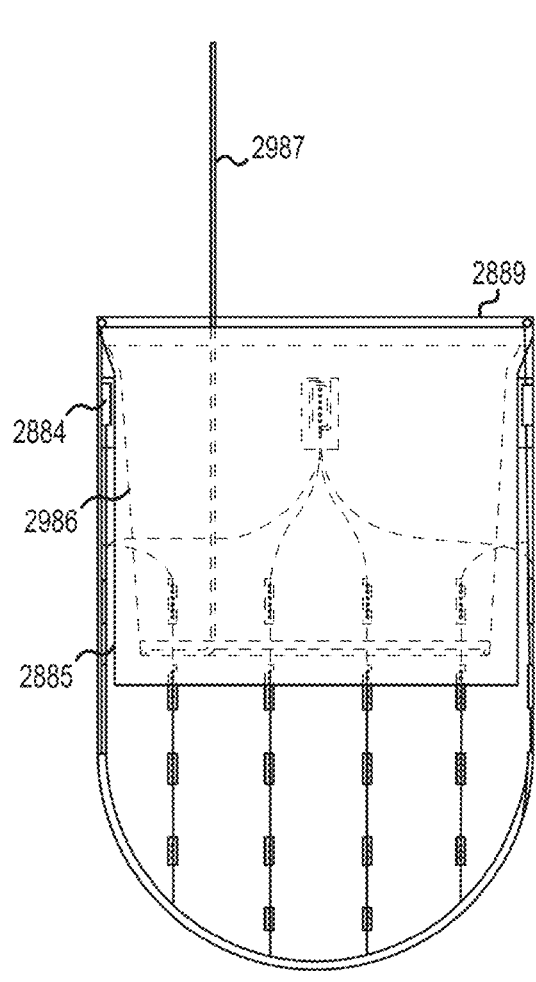

FIG. 6 illustrates a bag 600 having a drawstring 2987, according to various aspects of the present disclosure. In some embodiments, a drawstring 2987 is provided, and may be positioned or located at a bottom or distal edge of the containment flap 2986 to enable a user to close the containment flap and therefore capture the tissue specimen as well as contain fluids. This feature may be beneficial where the contents of the bag are desired to be contained during manipulation and exteriorization of the bag, such as where the tissue specimen is believed or suspected to contain cancerous cells. The containment flap and drawstring may also protect the bag features during loading of the tissue.

In some embodiments (see FIG. 6), two apron layers may be provided, a first apron layer 2885 to protect the bag features as previously described, and a second containment flap layer 2986 that can be used to contain the tissue specimen in a manner substantially as previously described herein.

After tissue specimen loading, the containment flap 2986 may be used to assist in exteriorizing the bag opening. Using a drawstring 2987 that is coupled to the distal edge of the containment flap along the circumference, pulling the drawstring through the incision site will raise the distal edge of the containment flap around the tissue specimen and draw the opening toward the incision. The drawstring may close or substantially close the containment flap and guide it through the incision. The bag opening may follow as it is pulled through the incision opening. When the bag has reached it intended exteriorized position, the bag can be secured with a semi-rigid member 2889 around the opening, can be inflated to secure or can be held with other mechanical means including being held in place by an attending surgeon. The drawstring can be loosened, and the containment flap can be spread and/or cut to provide access to the bag features on the interior surface, such as electrode(s) and or wire(s) or wire connectors.

In some embodiments, a separate means of exteriorizing the bag can be used so that the apron 2885 can remain in place until after exteriorization. The bag can be exteriorized by coupling a lead or suture 2888 (see FIG. 5) to the semi-rigid member 2889 which will help guide the bag opening toward and through the incision site. After exteriorization, the apron can be accessed and raised around the tissue specimen and out of the incision site where it can be cut or have a perforation feature 2890 that will allow the user to tear it away, providing access to the bag features on the interior surface, such as electrode(s) and/or wires(s) or wire connectors 2884. This embodiment has the additional benefit of reducing the chance of contact of the peritoneum or incision site with portions of the apron layer that have come in contact with the tissue specimen during loading and manipulation. The apron may collapse somewhat within the interior bag volume. This "curtaining" effect can cause the apron to not remain in close proximity to the interior surface of the bag. A feature can be added to the apron and corresponding location on the interior surface of the bag to help hold the distal most portion of the apron in place.

One advantage of the apron is that it keeps the wires and connectors out of the way during loading. Multiple and different aprons might be used to cover different wire sets where one apron can be removed first to expose one or more connectors for connection to the instrument before a second apron is removed to expose one or more other connectors. In another embodiment, one apron may have openings for the wire connector(s) to allow connection to the instrument while keeping the wires out of the way and avoid inadvertent wire tangling. In this embodiment one or more first aprons with the connector openings may cover the wires while still allowing access to the connectors, while one or more second aprons could be used for the primary purpose of protecting the connectors prior to connection with the instrument.

In some embodiments, the bag (e.g., bag 1062) comprises two or more film layers, where the two or more film layers are attached together by RF sealing, welding, and/or any other means to form a lumen where containment is desired. In some embodiments, perforations are provided to allow the wires to be released from the guide by the user. The films can also be designed with a thin inside film layer such that the user can "tear" the wires through the film prior to applying the pre-tension, thereby allowing unrestricted travel of the pre-tension introducer tube into the incision site in preparation for the cutting procedure.

In some embodiments, an extended wire channel is located underneath an apron, with the proximal termination near the connector temporarily attached to the inner surface of the bag. This attachment may be with a heat sealed connection that is designed with a perforation for the user to tear away when making the wire connection, may be a thin film such that the user can "tear" the extended wire channels away from the inner surface of the bag, may be attached with a slot in the side of the bag in which the extended wire channel is seated during manufacturing, and/or other methods of attaching this channel to the inner surface of the bag. In some embodiments, the attachment may be made with the wire connector by the use of a pouch or region of the bag near the opening in which the connector is placed during manufacturing in which the user can remove during wire connection.

The shape of the extended wire channels can be designed or configured to reduce the chance of twisting the wires when released from inside the bag. In some embodiments, a relatively wider extended channel may be provided. In some embodiments, a plurality of wire channels are provided and aligned in parallel on the same extended wire channel. The width of this extended wire channel resists the twisting of the wires as the user makes the connections. In some embodiments, Mylar strips or other material is attached to the wire channel film to enhance this anti-twist feature. In some embodiments, Mylar strips or other material is placed between the outer layer and a third layer of film so that the extended wire channel naturally stays aligned in the proper position.

Some embodiments provide separate channels within the segmentation instrument. For example, a tray that also aligns the tensioning mechanism during cutting may provide separate channels. Keeping the different wire sets separate within the instrument eliminates potential tangling or interfering with each of the different wire sets as they are tensioned and as the cut progresses.

In some embodiments, the return electrode cable extends from the distal portion, or bottom, of the specimen bag along the inner side wall of the bag and out of the bag opening. A means to ensure that the return electrode cable does not interfere with the wire sets is important to ensure unabated cutting. This return electrode cable can be separated from the wire sets by routing the cable in a location between wire sets under a return electrode cable "wire channel" composed of a polyurethane film in a similar manner as the wire channels that contain the wire set channels by bonding the cable to the inner side wall, or can be routed between layers of the polyurethane film or can be created by depositing conductive material on the bag surface with an insulation layer added to ensure electrical isolation.

Figure 7:
FIG. 7 illustrates several views of inflation mechanisms for a tissue removal bag, according to various aspects of the present disclosure.
Figure 7:
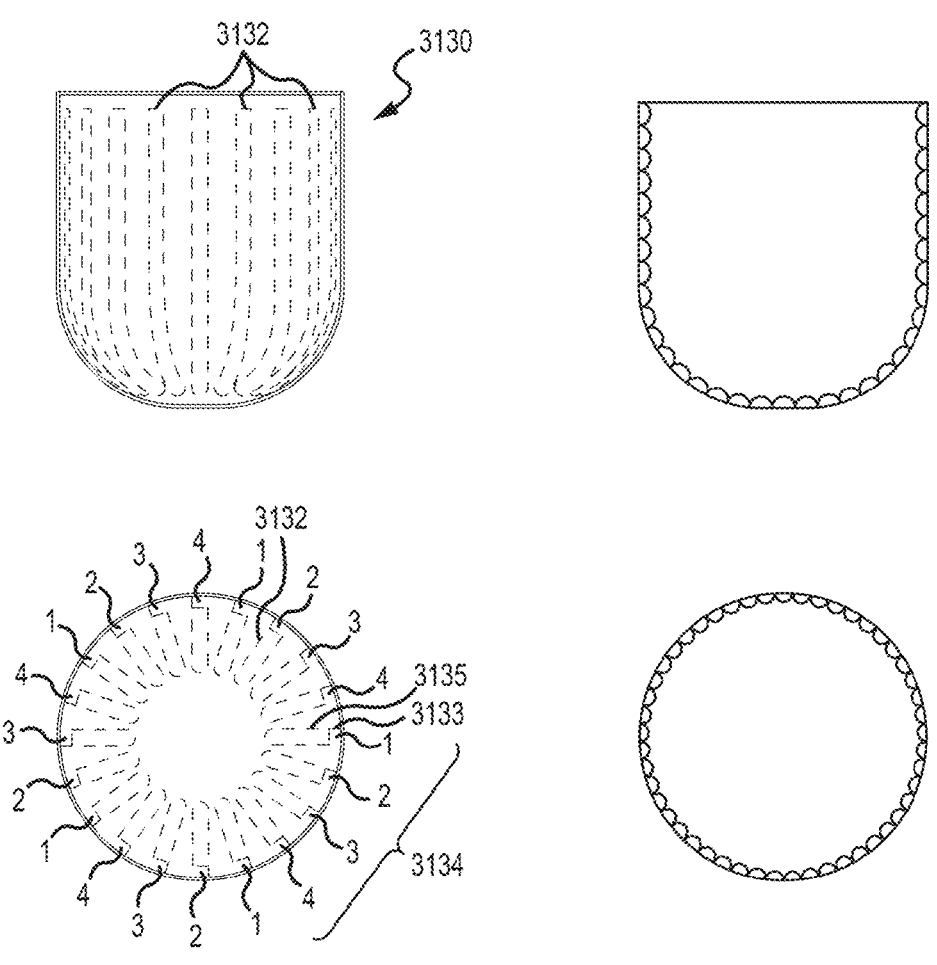

Turning now to FIG. 7, which illustrates several views of inflation mechanisms 700 for a tissue removal bag, according to various aspects of the present disclosure. In this example, a retrieval bag 3130 may be provided for the system 200, and the bag 3130 may include an inflatable feature. In some cases, the bag 3130 implements one or more aspects of the bag 1062 and inflatable channels 11121 described in relation to FIG. 28. Inflation of the bag 3130 may be achieved using a honeycomb pattern of inflated or inflatable cells 3132. A plurality of inflatable cells 3132 may provide a thermal barrier between the patient and the electrode(s)/wire(s) inside the bag 3130. If the inner layer is punctured or thermally fails, the cell(s) 3132 would collapse leaving the remaining cells 3132 intact, to continue to provide thermal protection. In some embodiments, the cells 3132 may include a plurality of inflation channels 3132 (also shown as inflatable channels 11121 in FIG. 28), some or all with a separate means to hold the pressure such as a separate syringe or stopcock. In some embodiments, the bag 3130 may include small independent areas that have static air captured under pressure.

The inflated cells 3132 provide an additional thermal insulation barrier between the tissue specimen or electrode and the adjacent structures outside of the exterior surface of the removal bag. In contrast, if the entire bag is inflated as a single cell, failure of one of the layers would cause the inflation and thermal insulation to be lost. By providing multiple independent inflation areas 3132 in the bag 3130, if one of the layers in an individual region fails, the thermal insulation of that layer may be lost or reduced; however, the remaining inflation cells 3132 will continue to provide thermal insulation, and minimize any thermal damage caused to the patient.

With continued reference to FIG. 7, a removal bag 3130 with multiple inflation areas 3134 (labeled 1, 2, 3, 4), each with a separate source of pressure or with a separate means to hold the pressure, may be provided. Those skilled in the art will understand that any number of inflation areas 3134 may be provided, and that the same or fewer means to inflate may be provided. For example, a first inflation area 3133 may be fluidly coupled to a second inflation area 3135 such that a single pressurizing source (e.g., fluid source 11124 in FIG. 28) may pressurize both areas 3133, 3135.

In some embodiments, inflation features, or functions are integrated within the wire channels. For example, a third layer may be provided at the channels. The first layer is the perforation layer, the second is a boundary layer and third is a bottom layer. The boundary layer and bottom layer are sealed so that when low pressure air or fluid in applied, the channel will inflate providing structure directly beneath the wire channels. This has a benefit in providing thermal insulation directly beneath the wire as well as helps provide structure which aides in release of the wire from the channels.

Figure 8:
FIG. 8 illustrates a side section view of some components of an electrosurgical device, according to various aspects of the present disclosure.
Figure 8:
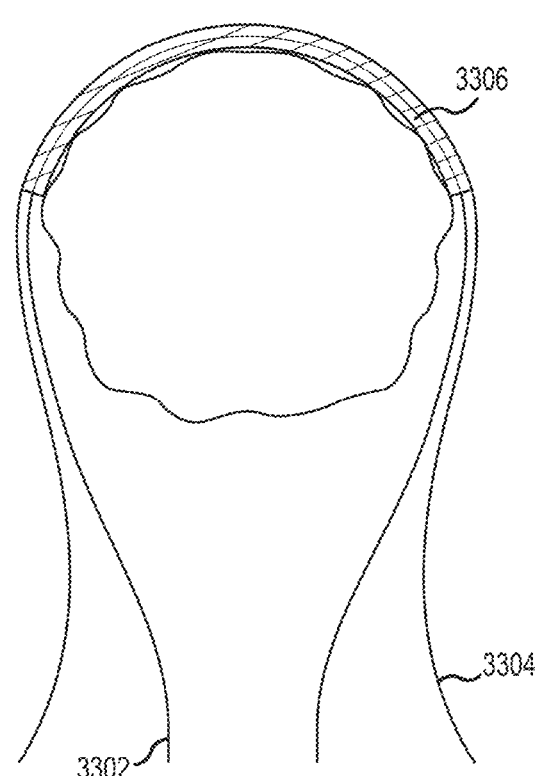

Turning now to FIG. 8, which illustrates a side section view 800 of some components of an electrosurgical device (such as electrosurgical device 102), according to various aspects of the disclosure. As seen in FIG. 8, an electrosurgical device 102 (see e.g., FIG. 2) may be provided, having one or more wire electrodes 3302 and a tissue removal bag 3304 (also shown as bag 1062). The wire electrodes 3302 may be coupled to the tissue removal bag 3304 by embedding the wire electrodes 3302 into a film 3306 on an interior of the removal bag 3304, as also described in relation to FIGS. 20-21B. A tissue cutting effect may be initialized by applying power to the wire electrode 3302, causing the film 3306 to break down, whereby the wire electrode 3302 is released from the bag and a spark between the tissue and the wire electrode 3302 is initiated to achieve the tissue cutting effect.

Those skilled in the art will understand generally that initiation of the wire to begin the cutting effect results from a separation between the wire electrode 3302 and the tissue when power such as RF energy is applied, and that coating on the wire electrode or a film material in the bag 3304 or any other component may be suitable for achieving this effect.

In some embodiments, a separate means to pre-tension the tissue sample and an insulative layer between the wire electrode 3302 and the tissue are provided for this purpose. This layer may be a pressurized air layer, a non-conductive fluid layer, an insulating film or layer applied between the wire and tissue, which may serve the alternative function of applying the tension of the tissue sample or could be achieved with the design of the bag, the wire attachment, and the pre-tension mechanism such that a gap results in the tissue wire/bag interface during operation. The desired wire set to be activated may have power such as RF energy applied and after sufficient power having a voltage is applied, the wire set may either be pulled to the surface of the tissue or may mechanically, electrically or with temperature break through the separation layer and begin the cutting effect. Generally stated, any easily electrically removable (or degradable) adhesive or retaining volume to hold the wire electrode in place may be provided, as illustrated in FIG. 8. Upon electrical input, the bare wire electrode 3302 will cut through the retaining medium (adhesive/retaining volume) or film 3306. This easy to degrade medium or film 3306 may also provide a pseudo air-gap, to promote initiation of the tissue cutting effect.

Figure 9:
FIG. 9 illustrates a partial transparent perspective view and a partial transparent side view of a removal bag, according to various aspects of the present disclosure.
Figure 9:
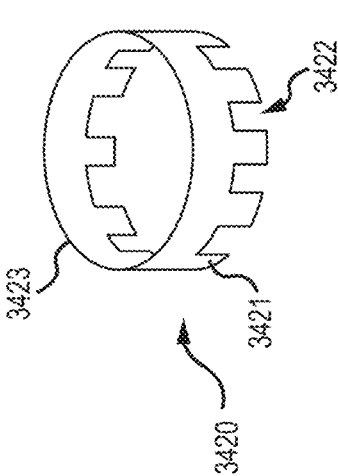
Figure 9:
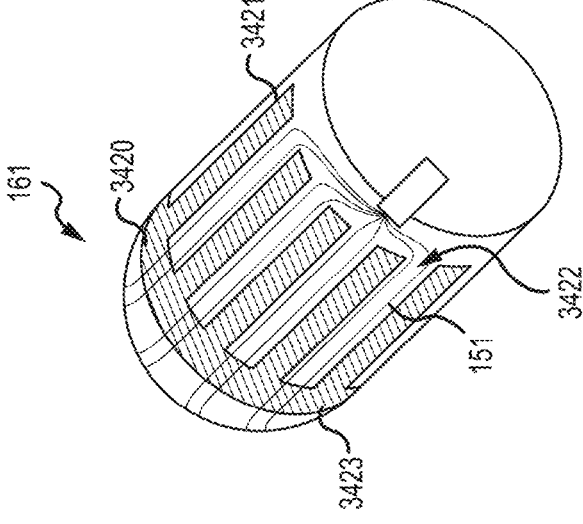

Turning now to FIG. 9, which illustrates a partial transparent perspective view and a partial transparent side view of a removal bag system 900, according to various aspects of the present disclosure. Here, the removal bag system comprises a bag 161, where a return electrode 3420 is attached to the bag and contains extensions 3421 longitudinally down the bag side walls. These extensions 3421 are located in-between the active electrode channels 3422 and are electrically connected using a ring 3423 at the distal portion of the bag side walls. In the illustrated configuration, the wires 151 only cross over the return electrode 3420 at the ring 3423; those skilled in the art will therefore recognize that the return electrode 3420 should be isolated from the wires 151 at the ring 3423, such as by a channel layer 10443 as previously described in relation to FIG. 21B. The isolation required to insulate the active electrode/wires 151 from the return electrode 3420 is reduced in the illustrated embodiment by the use of the extensions 3421. That is, in some embodiments, the electrosurgical device 102 may include a plurality of electrically conductive elongated portions or extensions 3421 coupled to a base or ring portion 3423. In addition, this configuration provided the lowest observed impedance occurring at the beginning of the cut (e.g., near the bottom of the bag or ring 3423). As the wire 151 travels into the tissue, the impedance will slightly increase providing more energy to sustain the cut as the wire travels away from the return electrode 3420.

One additional advantage of the return electrode 3420 is that the bag assembly will more easily compress to a small diameter to aide in insertion through the incision site.

Returning briefly to FIG. 2, in some embodiments, a removal bag 161 that contains multiple sets of active electrode wires 153, 155, 157, 159 may be provided. The bag 161 and active electrode wires 153, 155, 157, 159 may be designed to have a specific sequence of activations of the wires 153, 155, 157, 159 to avoid interference between a first wire set and a second wire set. To prevent a user from performing the power or RF energy activations in an incorrect sequence, connectors may be color coded or shaped to correspond with the tensioning mechanism connections. Relatedly, the tensioning mechanisms may have a predefined sequence of operation that the user or controller selects.

In some embodiments, inflation may be provided at specific areas (e.g., in an internal volume of the bag, in an area or volume surrounding the bag) to hold the tissue in place.

Figure 10:
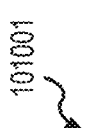
FIG. 10 illustrates top and side views of a tissue removal bag, according to various aspects of the present disclosure.
Figure 10:
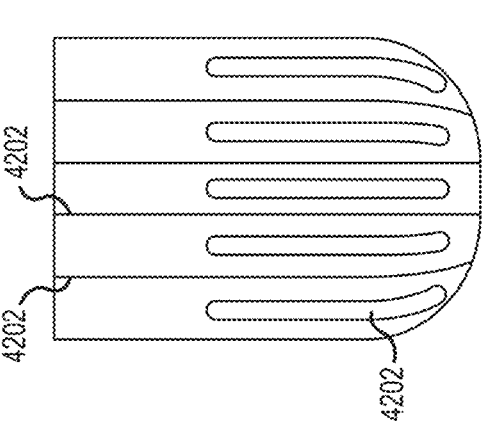

FIG. 10 illustrates a top view and a side view of a tissue removal system 101001 comprising a removal bag 4200 having four separate active electrode wire sets 4202, according to various aspects of the disclosure. The bag 4200 also includes inflatable channels 4204 that run parallel to the wire sets and are located on the bag surface in-between the wires. These inflatable channels 4204 are deflated when the tissue specimen is loaded and inflated after the bag 4200 is exteriorized and connected to the electrosurgical device 102. The inflation causes the inflation channels 4204 on the bag 4200 to extend to contact a surface of the tissue specimen and provide support around the circumference of the bag 4200. The tensioning mechanisms are then pre-tensioned to start the segmentation process. The location of the inflation channels 4204 may be selected to allow the active wire electrodes to contact the tissue and perform the cut without interfering with the channels 4204. The location of the inflation channels 4204 may also support the tissue during the entire cut, thereby reducing tissue "flow". After the cut is completed, the inflation channels 4204 may be deflated to allow specimen removal. This inflation and deflation can be performed with a syringe (e.g., shown as fluid source 11124 in FIG. 28). In some embodiments, the controller 108 or a second device may be configured to regulate the pressure automatically. Feedback on successful pressure application may be provided by observing an acceptable range of volume applied for inflation with a syringe and the resistance of increasing the pressure manually with an automated syringe application, or with pressure sensors in an automated pressure delivery device.

In some cases, active and return electrodes may be incorporated into a specimen bag construction, where the active electrode wires may be incorporated into the specimen bag by providing a multilayer construction. In one non-limiting example, the outer layer may include a nylon or elastomer, a first layer adjacent the outer layer may include a foil return, a second layer adjacent the first layer may include an insulating layer, a third layer adjacent the second layer may include the active electrode wire(s), and the fourth or innermost layer may include a perforated bag material.

Figure 11:
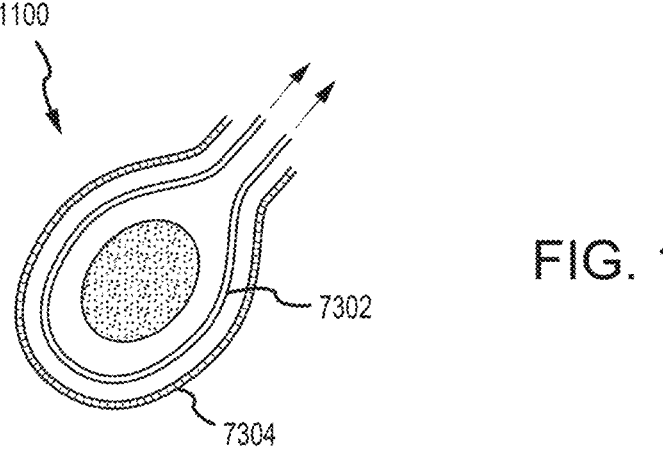
FIG. 11 illustrates a dual bag construction with an inner bag configured to constrict tissue, according to various aspects of the present disclosure.

As illustrated in FIG. 11, some embodiments include a dual bag construction 7300 for pre-tensioning the specimen. The dual bag construction 7300 may include an interior bag 7302, which may constrict the specimen by collapsing against the device, while the outer bag 7304 may contain or enclose the wire(s)/electrode(s) (not illustrated) used for cutting the specimen. The return electrode (not illustrated) may also be housed in the outer bag 7304.

Figure 12:
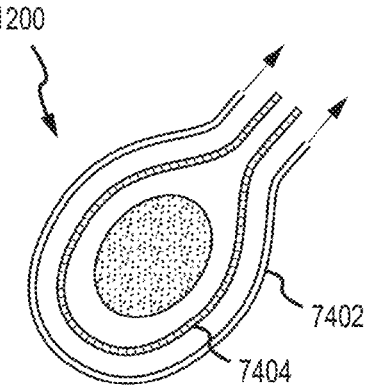
FIG. 12 illustrates a dual bag construction with an outer bag configured to constrict tissue, according to various aspects of the present disclosure.

As illustrated in FIG. 12, some embodiments provide a dual bag construction with return electrodes (not illustrated) in the outermost bag 7402. A dual layer bag construction 7400 may be used such that the outer bag 7402 constricts the specimen and contains the return electrode. The inner bag 7404 may contain the active electrode(s) (not illustrated) for cutting.

In some cases, the temporary holding of wires to the bag as described herein may be performed in several manners. As noted above, bags may include multiple layers, or single layers with additional features attached to temporarily hold the wires in place. The bags may include several film pieces welded or adhered together, as described in relation to FIGS. 20-24 above. Alternatively, the bags may be molded by reshaping a film or blown in a mold similar to a balloon. Regardless of the approach, the means by which the wires are held in place must be releasable and release in order to complete the segmentation of the tissue.

Another important feature of using wires to segment a specimen, either with or without radiofrequency energy, is to ensure that the wires are held to the side wall of the bag, as illustrated. By keeping the wire(s) temporarily attached to the side wall of the bag, the specimen may be loaded without inadvertently shifting the wire(s) or catching on the wires so the specimen can't be fully loaded. For this purpose, the wires may be held in place using loops, perforations or similar bag features that release with tension applied to the wires. In addition, the holding features may release in response to an application of energy to the wires that melt or soften the holding features. An additional approach is to have a mechanical pull or feature that the user can pull that releases the wires from the holding features. The mechanical pull or feature may be separate strings attached to the holding features that the user can access near the opening of the bag when exteriorized. Inflatable features within the bag itself may also be used to rupture the holding features.

One potential risk of temporarily attaching wires to the bag is that the bag ruptures during detachment of the wires. The use of multiple bag layers will help to ensure that the bag remains intact upon release of the holding features. The holding features are attached to the most inner layer of the bag, with one or more additional layers on the outside of the bag to ensure the bag remains intact and impermeable to fluids.

Additional features may be added that provide feedback to the user regarding bag integrity. The bag may be inflated or have inflatable channels, as described in relation to at least FIGS. 28-36. With inflation, the measured inflation pressure that the bag or inflatable channels holds is an indication of any possible holes in the bag. Use of a pressure valve with a sensor can be used to detect any drop in pressure. The pressure valve and/or means to inflate the bag or inflatable channels may be integrated into the bag or alternatively be integrated into the segmentation instrument itself. Other potential approaches include use of a camera and a light source to allow the user to view the outside of the bag during the procedure, use of a color changing indicator within the outer two layers of a three-layer bag that changes color upon contact with bodily fluids, or use of clear outer bag layers or films where the user can visually determine if any fluids have penetrated between the two layers. Another method could be to have a conductive deposition on the inside of the outer bag layer and a center layer that is separated to the outer layer by the inflation. The capacitance between the two conductive layers can be monitored such that a drop in pressure will change the capacitance reading, similar to a capacitive touchscreen press. The capacitance can be measured at regular intervals, on command or continuously or a threshold can be predetermined such that if the pressure is lost, the system can identify the condition and issue an alert. The two conductive layers can also be used in a similar manner as a resistive touchscreen in that the change in resistance between the two layers can be used to indicate a loss of pressure condition. Lastly the outer two layers of the bag may contain a sterile fluid by which the user can be confident of bag integrity if the fluid level has not fallen during the course of the procedure.

If the user visually determines a void in the bag, an adhesive patch may be applied in situ to reduce the risk of bodily fluid or tissue loss from the bag contents. The user may also decide to wash (rinse and suction) the patient's body cavity.

As previously described herein, rupture of the bag (e.g., bag 161, bag 1062, etc.) is a potential failure that should be monitored, prevented, and/or mitigated, whether with a tissue segmentation device or simply with a removal device that does not segment tissue.

With reference now to FIG. 13, a removal bag assembly 1300 may be provided that includes an outer bag layer 9102, an inner bag layer 9104, and a space 9106 therebetween. The removal bag assembly 1300 implements one or more aspects of the specimen bag systems described herein, including at least specimen bag system 11101 in FIG. 28. The layers 9102, 9104 may be coupled to or fused to one another using any means known in the art, such as at a joint 9108. Either vacuum or pressure between the bag layers 9102, 9104 may be used as part of a breach detection or mitigation strategy.

In some embodiments, pressure in the space 9106 between the layers 9102, 9104 may be used to inflate the outer bag layer 9102. If a breach occurs in the outer bag layer 9102, the loss of pressure can be detected visually by looking for a decrease in inflated bag size or pressure.

In some embodiments, a vacuum may be applied to the space 9106 between bag layers 9102, 9104. The vacuum may serve two purposes: first, a vacuum may provide a visual indication of a breach if the outer bag layer 9104 no longer appears to be pulled towards the inner layer 9104. Second, if a breach occurs in the outer bag layer 9104, the vacuum will draw air into the space between the bag layers 9102, 9104 thereby minimizing the potential for other materials or fluids to escape the hole (in particular if the hole is small). That is, a vacuum in the space 9106 between layers 9102, 9104 may tend to bias an inward flow of fluid, whereas a pressure in the space 9106 would tend to, in the event of a breach, release fluid out and potentially into the patient.

Figure 14:
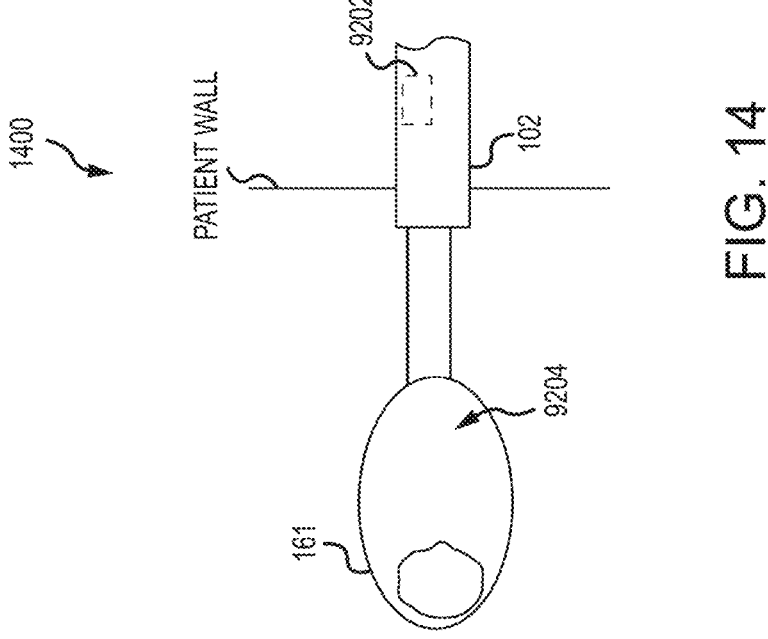
FIG. 14 is a side partial section view of some components of a bag assembly with leak detection, according to various aspects of the present disclosure.

In some embodiments, and as is illustrated in FIG. 14, the device 102 may include a $CO_2$ and/or $N_2O$ sensor, positioned, for example in the introducer tube, to detect the presence of the gas being used for insufflation. FIG. 14 illustrates a side partial section view 1400 of some components of a bag assembly with leak detection, according to various aspects of the present disclosure. The bag assembly in FIG. 14 implements one or more aspects of the other specimen bag assemblies described herein, including at least removal bag assembly 1300, bag 161, and/or bag 1062. In some circumstances, if the bag 161 is introduced into the patient cavity in a vacuum state or with atmospheric air therein, the gas used for insufflation, such as carbon dioxide or nitrous oxide, will tend to enter the interior space 9204 of the bag 161, and the sensor 9202 may be provided and configured to detect the change in the gas signature and/or to detect that the gas in the interior space 9204 has insufflation gas therein. Those skilled in the art will recognize that the sensor 9202 does not necessarily need to be inside the device 102 but merely needs to be exposed to the interior space 9204 for sampling, using any suitable means known or as-yet developed in the art. Additionally, or alternatively, the introducer tube may also comprise an optional light source for illuminating the interior of the bag. In one non-limiting example, the sensor 9202 may be replaced by a light source, or the light source may be positioned at or near the sensor 9202.

In some embodiments, a tube (not illustrated), lumen, or channel may be provided to expose the sensor 9202 to the intermediate space 9106 between the outer and inner layer bag layers 9102, 9104. The sensor 9202 may be positioned remotely from the bag assembly 1300 and coupled to the channel such that the sensor 9202 may sample the contents of the air in this intermediate space 9106. In some embodiments, the lumen or channel may be positioned at or near the joint 9108 described above in relation to FIG. 13.

In some embodiments, a slight vacuum may be applied to the space 9106 between layers 9102, 9104, or the bag interior space 9204, such that the content of gas being detected at the sensor 9202 is increased, thereby providing a more accurate indication of a leak. This slight vacuum may be created using a pump (not illustrated), evacuated air cylinder or other means to apply a negative pressure, including, but not limited to, an air flow control valve coupled with the sensor 9202 to draw the contents of the space 9106, or the bag interior space 9204 toward the sensor 9202 and ensure that the negative pressure can be maintained throughout the procedure.

As illustrated in FIG. 28, in some embodiments, one or more inflatable channels 11121 may be provided and coupled to the outside layer of the specimen bag 1062. Additionally, or alternatively, the intermediate space (e.g., intermediate space 9106 in FIG. 13) between the outer and inner bag layers 9102, 9104 may also be inflated. In some cases, a first inflatable channel 11121 may be coupled to a fluid source 11124 (or alternatively, a vacuum pump), and used as previously described to provide a positive (or negative pressure) to the intermediate space within the inflatable channel.

In some embodiments, an outer bag layer 9102 may be made of a first translucent color and an inner bag layer 9104 may be made of a second color, and a space 9106 therebetween may be pressurized. Such a design may aid in leak detection. For instance, a method of determining a leak may include visually determining a perceived change in color at one or more points of contact between the bag layers 9102, 9104. Visually determining may include using an endoscopic camera and/or a light source, or viewing the outer layer 9104 during or after the surgical procedure. For example, if the inner bag layer has a blue tint applied, and the outside layer has a yellow tint applied, the area of contact will result in a green tinted shape due to increase in optical coupling of the two-colored layers. In some embodiments, as the surgical procedure proceeds, a change is the size of the combined color area, particularly an increase, may indicate a change in the area of contact between the two layers. If a fixed volume of air is captured between the two layers in this intermediate space or if a slight pressure is applied prior to use, the increase of size of this color combined region can identify a leak of one of the bag layers.

Those skilled in the art will recognize that the procedure described above may also be suitable where a space 9106 between the layers is under vacuum. For example, if the layers 9102, 9104 pull away from each other, a leak is also indicated.

In some embodiments, a method of leak detection may include providing a moisture detection layer, and/or monitoring an electrical pattern indicative of conductive fluid or change in impedance due to fluids.

Figures 15A, 15B, 15C:
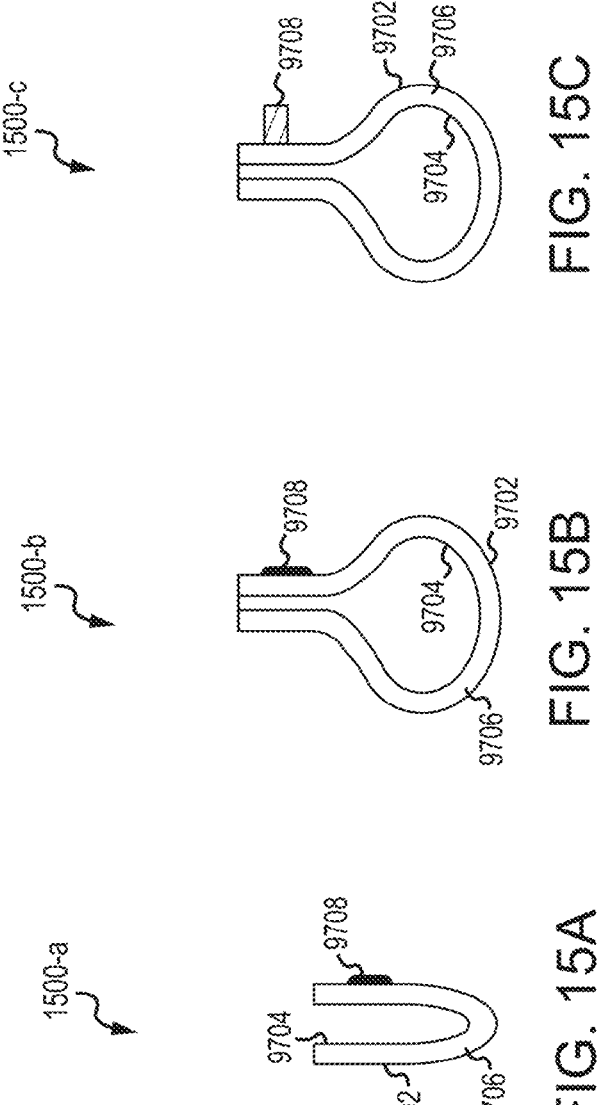
FIGS. 15A-15C illustrates side section views of some components of a bag assembly with leak detection, according to various aspects of the present disclosure.

With reference now to FIGS. 15A-15C, some embodiments (1500-a, 1500-b, 1500-c) of leak detection include providing or using an audible or visual indicator 9708 that expands or "pops" when a vacuum pressure in a space 9706 between two bag layers 9702, 9704 is lost (compare to a canning jar lid that pops when opened). For example, if a breach in either the inner or outer bag 9704, 9702 occurs, the vacuum loss indicator 9708 feature will pop, extend, or change from a first state of tension to a second state, to indicate to the surgeon that a breach in either layer of the bag has caused the void space between the two layers of specimen bag to lose its vacuum.

Some embodiments of leak detection may include providing or using a color changing moisture indicator between bag layers. For example, the specimen bag layers (i.e., inner bag layer 9704, outer bag layer 9702) may be constructed of two welded layers of polyurethane, creating a sealed inner space (e.g., space 9706) between the two layers. A compromise or leak in either of these two layers may be indicated by a color changing chemical agent that would be applied to the inner space during bag construction. When the chemical indicator comes in contact with water based, human fluids a chemical reaction with the fluid would create a color change in the agent that would be observable either from the endoscopic camera in the body cavity or observable directly by the surgeon after bag removal. The agent may be sprayed on to either or both inner walls of the polyurethane during assembly of the bag. The agent may also be inserted in construction as a loose powder or as a film of liquid. Strips of colored paper or fiber may hold the color changing agent.

Some embodiments of leak detection methods or devices include the use of a visual indicator, which may be with or without a camera and/or light source between layers. To provide a visual indication of whether or not a breach occurred in the inner bag, the outer bag layer may be made of a white or similarly contrasting material such that the surgeon can look for blood on inside of outer white layer either during the instrument use, such as with a camera, or after use. Discoloration of the outer bag inner surface may indicate that a breach of the inner bag layer has occurred.

Some embodiments of leak detection devices 1500 and methods may include the use of one or more vacuum loss indicators, such as indicator tubes or geometries, as illustrated in FIGS. 15A, B, and/or C. For example, one or more pockets, tubes or expansion members (i.e., audible or visual indicator 9708) may be positioned at locations around the outer layer 9702 of the bag assembly. One or more expansion members (i.e., audible or visual indicator 9708) may be non-distinct in a normal relaxed state, and, under normal conditions, with a fully contained and pressurized bag assembly, the geometries would remain in the relaxed state. If a leak occurs, however, in the inner bag layer 9704, the expansion member (i.e., audible or visual indicator 9708) on the outer layer 9702 would expand, providing an easily identifiable indication of an inner bag layer leak.

In some embodiments, a chemotherapy agent in the space between the bag layers may be configured to kill cells on contact. The agent may be a specific agent that is chosen or configured to target the intended procedure. In some embodiments, the agent is contained in a hydrogel or gel such that any cells that come into contact with the agent are likely to stick or adhere to the surface of the hydrogel or gel. The chemotherapy agent may be selected based on the procedure and/or patient history. For example, if a uterus is being removed, a chemotherapy agent that would be indicated for a leiomyosarcoma suitable for the patient may be used to best address any cancer cells that may migrate into the interior space of the bag or the space between bag layers. For colon removal an agent that is indicated for an adenocarcinoma may be selected and placed in the bag. In some embodiments, the surgeon and/or oncologist selects the chemotherapy agent and adds the agent to the space between the outer and inner layers just prior to use. In some embodiments, the surgeon and/or oncologist may select from a range of pre-administered chemotherapy agents that are placed in the bag or between bag layers during manufacturing. The agent may be applied in the form of a liquid with a safe quantity applied or may be applied as a film to either the outside layer of the inner bag or the inside layer of the outer bag.

In some embodiments of leak mitigation, an antiseptic or disinfectant solution of layer may be provided in a manner substantially similar to that described with respect to the chemotherapy agent previously described herein.

Some embodiments of leak mitigation include placing or using a layer of absorbent material in between the inner and outer bag layers such that if a leak occurs in the inner layer, the absorbent material will contain an amount of fluids or other material that breach the inner layer. This also provides some protection to resist both layers of the bag being damaged by instruments or other mechanical edges. The absorbent material may be a fabric, a foam, gel or other material that has highly absorbent properties to water.

Some embodiments of leak mitigation include providing or using an absorbent material that changes hardness or phases when in contact with a fluid. The material may be placed between the bag layers. It may be a dry substance that turns to a gel in some embodiments. In some embodiments, the substance may turn harder or softer, may be a powder or film that turns to a gel, or may change colors as a result of a chemically activated change. The material may change phases so as to be detected either visually, through physical palpation of the bag, etc.

Some embodiments of leak mitigation may include the use of or placement of a layer of viscous gel material between the inner and outer bag layers such that, if a leak occurs, the gel is configured to minimize the impact of a leak. The gel may, in some embodiments, close the leak; in some embodiments, the leak may increase the thickness of the bag such that a leak would have a lower probability of penetrating both the inner and outer bag layers and the gel layer. In some embodiments, the gel may be made of or include a biocompatible material. In some embodiments, the gel may include a hydrogel, such as that placed on return electrodes. In some embodiments, the gel includes a hydrophilic polymeric material, a biodegradable hydrophilic material, and/or an organic hydrophilic material. The gel may be added to the space between layers at manufacturing; or the gel may be added through a lumen in-situ.

The gel may be selected and configured to thermally insulate the outer layer from the inner layer, thereby reducing the likelihood of a breach of both layers.

Some embodiments of leak mitigation include the use of a multi-cell intermediate layer. A multi-cell layer between the outer bag layer and the inner bag layer may include a number of interior spaces that serve to reduce the volume of fluid that may potentially leak in the event the inner layer is compromised. For example, a number of walls coupling the inner layer and the outer layer may form a number of smaller fixed volumes of air, fluid, gel, or other leak mitigation or leak management means described herein within the space between the inner and outer layers of the bag.

In some embodiments, the smaller fixed volumes of air fluid, gel, or other leak mitigation or leak management means described herein may be provided by a third bag layer positioned between the inner layer and the outer layer. The third layer may include an inner wall, an outer wall, and a number of connecting walls coupling the inner wall and the outer wall, creating the fixed volumes therebetween.

In some embodiments, a multi-cell layer may include a plurality of sealed pockets of a fluid, or a leak mitigation means. The multi-cell layer may be positioned between the inner layer and the outer layer. The multi-cell layer may limit travel of contaminated material and reduce the probability of contaminated material such as portions of a cancerous segmented tissue sample breaching the bag assembly. The multi-cell layer may be positioned exterior of both bag layers in some embodiments.

In some embodiments, a material that is reactive with carbon dioxide and/or nitrous oxide may be used or placed in the space between the outer and inner layers. The reactive material may be selected or configured to form a foam or gel, or to solidify, thereby mitigating the effects of any breach of the inner bag layer.

Bag Folding and Rolling

Folding and rolling a containment bag for inserting into an outer tube presents many challenges as the bag size and number of bag layers increases. Currently used techniques for folding and rolling containment bags into outer tubes or lumens are lacking in several regards. In some circumstances, a focus on bag rolling method may be critical to ensure a consistent rolled containment bag diameter. For a containment bag that incorporates active electrode wires and return electrode(s)—a full bag unrolling may facilitate in optimizing tissue sample division using these electrode wires. Numerous techniques for bag folding and rolling prior to insertion into an outer tube are described. As noted above, in some cases, the outer tube is shaped and sized to receive an inner tube, where the inner tube is coupled to or in communication with the rolled-up containment bag and utilized to unfurl the rolled-up containment bag from the distal end of the outer tube. In some cases, the containment bag may be unfurled by pushing the inner tube, distally, which serves to push the containment bag in a distal direction and out of the outer tube.

In one non-limiting example, an angled rolling method may be utilized. In this example, the containment bag may first be flattened along a plane comprising the rolling axes, which may serve to minimize the bulk/volume of the rolled containment bag. Next, the flattened containment bag may be folded at or near the middle region of the bag depth prior to rolling. In some cases, starting the rolling process near the middle region may serve to reduce the bag bottom bulk and/or number of rolls required to completely roll up the containment bag. In some cases, the subsequent insertion of tissue specimen may encourage a bag that has been folded near the middle region to completely unfurl as the tissue is loaded and the bag opening exteriorized, for instance, due to the weight of the tissue specimen. In some examples of the angled rolling method, the specimen/containment bag may be folded and rolled, for instance, beginning with the proximal end, prior to insertion into the outer tube. In some instances, a slight angle on the folded bag between the top bag opening region and the folded over lower region may be provided, which may ease insertion into the outer tube. For instance, in some cases, the folded lower region may be angled away from the proximal side of the bag prior to bag loading, which may serve to reduce the proximal bag side bulk after rolling, thereby making rolled containment bag insertion into the outer tube easier.

In another non-limiting example for folding and rolling a containment bag, two sticks arranged parallel (or substantially parallel) to each other may be utilized. In this case, a first stick may be placed at the central region of the flattened bag where the bag fold will occur. Additionally, a second stick may be placed parallel to the first stick but on an opposing side of the flattened bag. In some embodiments, these sticks may be squeezed together and rolled with tension on the folded bag while the top of the containment bag assembly is held in place. In some circumstances, rolling the sticks at a slight angle to the bag may help reduce the bag roll bulk at the proximal side of the rolled bag.

In some embodiments, the rolled bag can be inserted into the outer tube with or without the rolling sticks removed. In some cases, for instance, if stick removal is needed, the sticks can be untwisted in a direction opposite the original bag roll in order to give space for the tensioned sticks to be removed from the center of the rolled bag. For containment bag film integrity, a method of using a film over each of the sticks may be employed. Similar to the case above, the sticks can be untwisted in a direction opposite the original bag roll in order to give space for the tensioned sticks to be removed from the center of the rolled bag. In this example, each of the two sticks may first be removed, following which the respective stick films may be removed. In one non-limiting example, a highly lubricious film, such as a PTFE heat shrink, may be utilized as the stick film. Other types of materials may be used to form the stick film in different embodiments, and the example listed above is not intended to be limiting.

In some other cases, a "W" fold is incorporated in the flat bottom containment bag prior to folding and rolling. The use of the "W" fold prior to folding and rolling may serve to encourage complete unfurling of the containment bag's flat bottom during use. In another example, the bottom floor of the bag is folded over (i.e., prior to folding and rolling) so that it sits flat and parallel with the flattened main bag body.

Each of the various elements disclosed herein may be achieved in a variety of manners. This disclosure should be understood to encompass each such variation, be it a variation of an embodiment of any apparatus embodiment, a method or process embodiment, or even merely a variation of any element of these. Particularly, it should be understood that the words for each element may be expressed by equivalent apparatus terms or method terms—even if only the function or result is the same. Such equivalent, broader, or even more generic terms should be considered to be encompassed in the description of each element or action.

Such terms can be substituted where desired to make explicit the implicitly broad coverage to which this invention is entitled.

As but one example, it should be understood that all action may be expressed as a means for taking that action or as an element which causes that action. Similarly, each physical element disclosed should be understood to encompass a disclosure of the action which that physical element facilitates. Regarding this last aspect, the disclosure of a "cutting mechanism" should be understood to encompass disclosure of the act of "cutting"—whether explicitly discussed or not and, conversely, were there only disclosure of the act of "cutting", such a disclosure should be understood to encompass disclosure of a "cutting mechanism". Such changes and alternative terms are to be understood to be explicitly included in the description.

The previous description of the disclosed embodiments is provided to enable any person skilled in the art to make or use the present invention defined by the claims. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A containment bag assembly for extracting a tissue specimen from a patient, the containment bag assembly comprising:
a containment bag comprising one or more segmenting wires; an outer tube comprising a distal end and a proximal end, the outer tube further comprising a trocar;
a flexible ring, the flexible ring configured to form a top opening of the containment bag, wherein the flexible ring comprises:
two ring subassemblies, each ring subassembly comprising a proximal end and a distal end; and
a flexible member positioned between and coupled to the distal ends of the two ring subassemblies, wherein the flexible member is movable between a collapsed position and an expanded position, the flexible member further having a lead-in feature, the lead-in feature having a blunt tip, wherein the blunt tip is configured to protrude past the distal end of the outer tube when a distal tip pressure is at or above a threshold and retract back into the lead-in feature of the flexible member when the distal tip pressure is below the threshold;
wherein, when the flexible member is in the collapsed position, the two ring subassemblies are in a collapsed position and the containment bag is configured to be contained within the outer tube, and
when the flexible member is in the expanded position, the two ring subassemblies and the flexible member bias the top opening of the containment bag to an open position to enable placement of the tissue specimen within the containment bag.

2. The containment bag assembly of claim 1, wherein the flexible member comprises a hinge, the hinge having a leading angle that is less than 90 degrees from a central axis of the outer tube.

3. The containment bag assembly of claim 1, wherein each of the two ring subassemblies comprises a spring arm, and wherein the two ring subassemblies are parallel or substantially parallel to each other when in the collapsed position.

4. The containment bag assembly of claim 3, wherein the two ring subassemblies and the flexible member are configured to be disposed in the collapsed position with the containment bag within the outer tube in a first retracted position.

5. The containment bag assembly of claim 4, wherein the two ring subassemblies and the flexible member are configured to be pushed into a second advanced position outside the outer tube, and wherein the flexible ring retains the top opening of the containment bag in the open position.

6. The containment bag assembly of claim 1, wherein the flexible ring is configured to slide out of the distal end of the outer tube, push the containment bag out of the distal end, move the flexible member to the expanded position, and retain the top opening of the containment bag in the open position.

7. The containment bag assembly of claim 1, wherein the flexible member comprises a spring bias.

8. The containment bag assembly of claim 1, wherein the containment bag comprises a plurality of layers, including at least one electrically insulative layer for providing an electrosurgical effect between the one or more segmenting wires and a return electrode located in an interior of the containment bag.

9. The containment bag assembly of claim 8, wherein each of the at least one electrically insulative layer is composed of a high dielectric constant material selected from a polymer film, polyethylene, Polytetrafluoroethylene (PTFE), Ethylene tetrafluoroethylene (ETFE), Polyethylene terephthalate (PET), polyamide, and polyester.

10. The containment bag assembly of claim 8, wherein each of the at least one electrically insulative layer comprises a flexible polymer film having a high dielectric constant coating, the high dielectric constant coating comprising one of a polymer film, polyethylene, Polytetrafluoroethylene (PTFE), Ethylene tetrafluoroethylene (ETFE), Polyethylene terephthalate (PET), polyamide, and polyester.

11. The containment bag assembly of claim 1, wherein, the containment bag comprises a plurality of layers separated by one or more fluid gaps to provide insulation between an interior of the containment bag and an exterior of the containment bag, and each of the one or more fluid gaps is filled with air, deionized water, or silicone.

12. The containment bag assembly of claim 11, wherein the one or more fluid gaps of the containment bag are configured to be filled after the containment bag is positioned in an interior cavity of the patient.

13. The containment bag assembly of claim 1, wherein the containment bag comprises a plurality of layers that are welded together.

14. The containment bag assembly of claim 13, wherein the plurality of layers comprises layers of different refractive indices arranged to reduce or minimize light refraction between an interior of the containment bag and an exterior of the containment bag, and wherein the plurality of layers are arranged in one of an ascending order of refractive index or a descending order of refractive index from the interior to the exterior of the containment bag.

* * * * *